US006475763B1

(12) United States Patent
Ayal-Hershkovitz et al.

(10) Patent No.: US 6,475,763 B1
(45) Date of Patent: Nov. 5, 2002

(54) GENETICALLY MODIFIED CELLS AND METHODS FOR EXPRESSING RECOMBINANT HEPARANASE AND METHODS OF PURIFYING SAME

(75) Inventors: Maty Ayal-Hershkovitz, Herzliya; Haim Moskowitz, Ness-Ziona; Daphna Miron, Rehovot; Ayelet Gilboa, Bat-Yam; Madlene Mimon, Ashdod; Hanna Ben-Artzi, Rishon Lezion; Oron Yacoby-Zeevi, Meitar; Iris Pecker, Rishon Lezion; Yoav Peleg; Yinon Shlomi, both of Rehovot, all of (IL)

(73) Assignee: Insight Strategy & Marketing Ltd., Rehovot (IL)

( * ) Notice: Subject to any disclaimer, the term of this patent is extended or adjusted under 35 U.S.C. 154(b) by 0 days.

(21) Appl. No.: 09/487,716

(22) Filed: Jan. 19, 2000

Related U.S. Application Data

(63) Continuation of application No. 09/260,038, filed on Mar. 2, 1999, now Pat. No. 6,348,344, which is a continuation-in-part of application No. 09/071,618, filed on May 1, 1998, now abandoned, which is a continuation-in-part of application No. 09/071,739, filed on May 1, 1998, now Pat. No. 6,177,545, which is a continuation-in-part of application No. 08/922,170, filed on Sep. 2, 1997, now Pat. No. 5,968,822.

(51) Int. Cl.[7] ............................. C12Q 1/00; C12Q 1/37; G01N 33/53; C12N 9/00; C12N 9/24
(52) U.S. Cl. ......................... 435/200; 435/4; 435/7.91; 435/183; 435/23
(58) Field of Search ........................... 435/4, 23, 7–91, 435/183, 200

(56) References Cited

PUBLICATIONS

Benezra et al. Thrombin enhances the degradation of heparan sulfate in the extracellular matrix by tumor cell heparanase. Exptl. Cell. Res. (1992) vol. 201:208–215.*
Burgess et al, "The Heparin–Binding (Fibroblast) Growth Factor Family of Proteins", *Annu Rev Biochem*, 58:575–606, 1989.
Campbell et al, "Heparan Sulfate–Degrading Enzymes Induce Modulation of Smooth Muscle Phenotype", *Experimental Cell Research*, 20:156–167, 1992.
Gordon–Cardo et al, "Expression of Basic Fibroblast Growth Factor in Normal Human Tissues", *Laboratory Investigation*, 63:832–840, 1990.
Eisenberg et al, "Lipoprotein Lipase Enhances Binding of Lipoproteins to Heparan Sulfate on Cell Surface and Extracellular Matrix", *J. Clin. Invest.*, 90:2013–2021, 1992.
Folkman et al, "A Heprin–Binding Angiogenic Protein–Basic Fibroblast Growth Factor–Is Stored Within Basement Membrane", *Am. J. Path.*, 130(2):393–400, 1988.
Folkman et al, "Angiogenic Factors", *Science*, 235:442–447, 1987.

Gitay–Goren et al, "The Binding of Vascular Endothelial Growth Factor to its Receptors is Dependent on Cell Surface–Associated Heparin–Like Molecules", *J. Biol. Chem.*, 267(8):6093–6098, 1992.
Ishai–Michaeli et al, "Importance of Size and Sulfation of Heparin in Release of Basic Fibroblast Grwoth Factor from the Vascular Endothelium and Extracellular Matrix", *Biochemistry*, 31:2080–2088, 1992.
Jackson et al, "Glycosaminoglycans: Molecular Properties, Protein Interactions, and Role in Phsiological Processes", *Physiological Rev*, 71(2):481–539, 1991.
Kjellen et al, "Proteoglycans: Structures and Interactions", *Annu Rev Biochem*, 60:443–475, 1991.
Liotta et al, "Tumor Invasion and the Extracellular Matrix", *Laboratory Investigation*, 49(6):636–647, 1983.
Matzner et al, "Degradation of Heparan Sulfate in the Subendothelial Extracellular Matrix by a Readily Released Heparanase from Human Neutrophils", *J. Clin Invest*, 76:1306–1313, 1985.
Mollinedo et al, "Major Co–Localization of the Extracellular–Matrix Degradative Enzymes Heparanase and Gelatinase in Tertiary Granules of Human Neutrophils", *Biochem J.*, 327:917–923, 1997.
Narindrasorasak et al, "High Affinity Interactions between the Alzeimer's β–Amyloid Precursor Proteins and the Basement Membrane Form of Heparan Sulfate Proteoglycan", *J. Biolog Chem*, 266(20):12878–12883, 1991.
Nakajima et al, "Heparanases and Tumor Metastasis", *J. Cellular Biochem*, 36:157–167, 1988.
Ornitz et al, "FGF Binding and FGF Receptor Activation by Synthetic Heparan–Derived Di– and Trisaccharides", *Science*, 268:432–436, 1995.
Rapraeger et al, "Requirement of Heparan Sulfate for bFGF–Mediated Fibroblast Growth and Myoblast Differentiation", *Science*, 252:1705–1709, 1991.
Vlodasky et al, "Lymphoma Cell Mediated Degradation of Sulfated Proteoglycans in the Subendothelial Extracelluiar Matrix: Relationship to Tumor Cell Metastasis", *Cancer Res.*, 43: 2704–2711, 1983.
Vlodavsky et al, "Involvement of Heparanase in Tumor Metastasis and Angiogenesis", *Israel J. Med Sci*, 24:464–470, 1988.
Zhong–Sheng et al, "Role of Heparan Sulfate Proteoglycans in the Binding and Uptake of Apolipoprotein E–Enriched Remnant Lipoproteins by Cultured Cells", *J Biolog Chem*, 268(4):10160–10167, 1993.
Vlodavsky et al, "Extracellular Matrix–Bound Growth Factors, Enzymes, and Plasma Proteins", *Molecular and Cellular Aspects of Basement Membranes*, Academic Press, Inc. 1993, pp. 327–342.
Wight, TN, "Cell Biology of Arterial Proteoglycans", *Arteriosclerosis*, 9:1–20, 1989.

* cited by examiner

Primary Examiner—Rebecca E. Prouty
Assistant Examiner—Manjunath N. Rao
(74) *Attorney, Agent, or Firm*—G. E. Ehrlich Ltd.

(57) ABSTRACT

Bacterial, yeast and animal cells and methods for overexpressing recombinant heparanase in cellular systems, methods of purifying recombinant heparanase therefrom and modified heparanase species which serve as precursors for generating highly active heparanase by proteolysis.

8 Claims, 30 Drawing Sheets

1. PCR reaction 1: insertion of ClaI site and protease site by PCR

2. Digestion of PCR product with ClaI and AflII

3. PCR reaction 2: insertion of ClaI site by PCR

4. Digestion of PCR product with ClaI and AatII

5. Ligate ClaI and AflII fragment of PCR1 with ClaI and AatII fragment of PCR2 into pFast*hpa* digested with AflII and AatII

GENETICALLY MODIFIED CELLS AND METHODS FOR EXPRESSING RECOMBINANT HEPARANASE AND METHODS OF PURIFYING SAME

This is a continuation of U.S. patent application Ser. No. 09/260,038, filed Mar. 2, 1999, now U.S. Pat. No. 6,348,344, Feb. 19, 2002, which is a continuation-in-part of U.S. patent application Ser. No. 09/071,618, filed May 1, 1998, (abandoned) which is a continuation-in-part of U.S. Pat. application Ser. No. 09/071,739, filed May 1, 1998, now U.S. Pat. No. 6,177,545, Jan. 23, 2001 which is a continuation-in-part of U.S. Pat. application Ser. No. 08/922,170, filed Sep. 2, 1997 now U.S. Pat. No. 5,968,822, Oct. 19, 1999.

FIELD AND BACKGROUND OF THE INVENTION

The present invention relates to genetically modified cells overexpressing recombinant heparanase, to methods of overexpressing recombinant heparanase in cellular systems and to methods of purifying recombinant heparanase. The invention further relates to nucleic acid constructs for directing the expression of modified heparanase species to which a protease recognition and cleavage sequence has been introduced, to the modified heparanase species expressed therefrom and to their proteolytic products. The invention further relates to in vivo methods of inhibiting heparanase activity.

The extracellular matrix (ECM) acts both as a structural scaffold and as an informational medium. Its dynamic status is determined by cells that secrete both its constituent molecules and enzymes that catalyze the degradation of these molecules. A stasis between ECM degrading enzymes and their inhibitors maintains the integrity of the matrix. While controlled ECM remodeling is fundamental to normal processes, uncontrolled disruption underlies diverse pathological conditions.

Among the integral constituents of basement membrane and ECM are cell adhesion molecules such as laminin and fibronectin, structural components like collagen and ellastin, and proteoglycans including sydecan, serglican, proteoglycan I and II versican (1–2).

Brief Overview on Recombinant Gene Expression

For biochemical characterization of a protein and pharmaceutical applications, it is often necessary to overproduce and purify large quantities of the protein. A major consideration when setting up a production scheme for a recombinant protein is whether the product should be expressed intracellularly or if a secretion system can be used to direct the protein to the growth medium. The inherent properties of the protein and the intended applications dictate the expression system of choice. Another consideration when attempting the production of recombinant eukaryotic proteins are the folding and post translational modification processes associated with their natural expression.

Preferably, production is carried out in a cellular system that supports appropriate transcription, translation, and post-translation modification of the protein of interest. Thus, cultured mammalian cells are widely used in applied biotechnology as well as in different disciplines of basic sciences of cellular and molecular biology for producing recombinant proteins of mammalian origin.

One of the most widely used cells for recombinant protein expression, particularly for biotechnological applications, is the Chinese hamster ovary cell line (CHO). Alternatively, baby hamster kidney cells (BHK21), Namalwa cells, Dauidi cells, Raji cells, Human 293 cells, Hela cells, Ehrlich's ascites cells, Sk-Hep1 cells, $MDCK_1$ cells, $MDBK_1$ cells, Vero cells, Cos cells, CV-1 cells, NIH3T3 cells, L929 cells and BLG cells (mouse melanoma) have also been shown to consecutively express large quantities of recombinant proteins.

These cells are easily transfected with foreign DNA, that can integrate into the host genome to create stable cell lines, with new acquired characteristics (i.e. expression of recombinant proteins). These new cell lines originate from a single cell that has undergone foreign DNA incorporation and are therefore referred to as "cellular clones".

Since integration of foreign DNA in host cell genome is relatively inefficient, the isolation of cellular clones requires a selection system that discriminates between the stably transformed and the primary cells.

Dihydrofolate reductase deficiency in CHO cells (CHO dhfr- cell line) offers a particularly convenient selection system for cellular clones. Transfection of the dhfr gene along with the gene of interest, results in the survival of clones in a growth medium containing methotrexate (MTX). The higher the number of foreign dhfr gene copies in the cellular clone, the higher the MTX concentration the cells can survive. It has been demonstrated that integration events of foreign DNA into host cell genome often maintain all the components of the transfected DNA. e.g., the selection marker as well as the gene of interest (67).

In contrast to mammalian expression systems, that inherently express limited quantities of recombinant proteins, other expression systems, such as bacteria, yeast, and virus infected insect cells are widely used.

Using such cellular gene expression systems, large amounts of either active or non-active protein can be obtained and used for biochemical analysis of protein properties, structure function relationship, kinetic studies, identification of, screening for, or production of specific inhibitors, production of poly- and monoclonal antibodies recognizing the protein, pharmaceutical applications and the like.

Bacteria are the most powerful tool for the production of recombinant proteins. A recombinant protein that is overproduced in a bacterial system might constitute up to 30% of the total protein content of the cells. The recombinant protein accumulates in inclusion bodies where it is relatively pure (comprises up to 50% of the protein content of the bodies) and protected from protease degradation.

Inclusion bodies enable the accumulation of up to 0.2 grams of protein per liter fermentation culture.

Using specific expression vectors, bacteria can also be directed to produce and secrete proteins into the periplasm and therefrom into the growth medium. Although the reported production quantities are not as high as in inclusion bodies, purification of the expressed protein may be simpler (68).

These advantages and the relative simple growth conditions required for bacteria to thrive, made bacteria a powerful and widely used cellular expression system for the production of recombinant proteins of interest (e.g., human α-interferon, human β-interferon, GM-CSF, G-CSF, human LNF-γ, IL-2, IL-3, IL-6, TNF, human insulin, human growth hormone, etc.).

Furthermore, non-active bacterialy produced recombinant proteins due to inappropriate folding and disulfide bonding may be reduced and/or denatured and thereafter deoxidized and/or refolded to acquire the catalytically active conformation.

However, when glycosylation of the protein is essential for its activity or uses, eukaryotic expression systems are required.

Yeasts are eukaryotic microorganisms which are widely used for commercial production of recombinant proteins. Examples include the production of insulin, human GM-CSF and hepatitis B antigens (for vaccination) by the yeast *Saccharomyces cerevisiae*. The relatively simple growth conditions and the fact that yeasts are eukaryotes make the yeast gene expression system highly suitable for the production of recombinant proteins, primarily those with pharmaceutical relevance.

In recent years methylotrophic yeasts (e.g., *Pichia pastoris, Hansenula polymorpha*) became widely used, thus replacing in many cases the more traditionally used yeast *Saccharomyces cerevisiae*.

Methylotrophic yeasts can grow to a high cellular density, and express and if appropriately, secrete, high levels of recombinant proteins. Quantities of the secreted, correctly-folded recombinant protein can accumulate up to several grams per liter culture. These advantages make *Pichia pastoris* suitable for an efficient production of recombinant proteins (69).

One aspect of the present invention thus concerns the expression of recombinant heparanase in cellular systems.

Heparan Sulfate Proteoglycans (HSPGs)

HSPGs are ubiquitous macromolecules associated with the cell surface and extracellular matrix (ECM) of a wide range of cells of vertebrate and invertebrate tissues (3–7). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (3–7). Studies on the involvement of ECM molecules in cell attachment, growth and differentiation revealed a central role of HSPGs in embryonic morphogenesis, angiogenesis, metastasis, neurite outgrowth and tissue repair (3–7). The heparan sulfate (HS) chains, which are unique in their ability to bind a multitude of proteins, ensure that a wide variety of effector molecules cling to the cell surface (6–8). HSPGs are also prominent components of blood vessels (5). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of normal and malignant blood-borne cells (9–11). HS catabolism is observed in inflammation, wound repair, diabetes, and cancer metastasis, suggesting that enzymes which degrade HS play important roles in pathologic processes.

Heparanase

Heparanase is a glycosylated enzyme that is involved in the catabolism of certain glycosaminoglycans. It is an endo-β-glucuronidase that cleaves heparan sulfate at specific intrachain sites (12–15). Interaction of T and B lymphocytes, platelets, granulocytes, macrophages and mast cells with the subendothelial extracellular matrix (ECM) is associated with degradation of heparan sulfate by heparanase activity (16). Connective tissue activating peptide III (CTAP), an α-chemokine, was found to have heparanase-like activity. Placenta heparanase acts as an adhesion molecule or as a degradative enzyme depending on the pH of the microenvironvent (17).

Heparanase is released from intracellular compartments (e.g., lysosomes, specific granules) in response to various activation signals (e.g., thrombin, calcium ionophores, immune complexes, antigens and mitogens), suggesting its regulated involvement in inflammation and cellular immunity responses (16).

It was also demonstrated that heparanase can be readily released from human neutrophils by 60 minutes incubation at 4° C. in the absence of added stimuli (18).

Gelatinase, another ECM degrading enzyme which is found in tertiary granules of human neutrophils with heparanase, is secreted from the neutrophils in response to phorbol 12-myristate 13-acetate (PMA) treatment (19–20).

In contrast, various tumor cells appear to express and secrete heparanase in a constitutive manner in correlation with their metastatic potential (21).

Degradation of heparan sulfate by heparanase results in the release of heparin-binding growth factors, enzymes and plasma proteins that are sequestered by heparan sulfate in basement membranes, extracellular matrices and cell surfaces (22–23).

Purification of Natural Heparanase

Heparanase activity has been described in a number of cell types including cultured skin fibroblasts, human neutrophils, activated rat T-lymphocytes, normal and neoplastic murine B-lymphocytes, human monocytes and human umbilical vein endothelial cells, SK hepatoma cells, human placenta and human platelets.

A procedure for purification of natural heparanase was reported for SK hepatoma cells and human placenta (U.S. Pat. No. 5,362,641) and for human platelets derived enzymes (62). Purification was performed by a combination of ion exchange and various affinity columns including Con-A Sepharose, Blue A-agarose, $Zn^{++}$-chelating agarose and Heparin-Sepharose. Evidently, the amounts of active heparanase recovered by these methods is low.

Cloning and Expression of the Heparanase Gene

A purified fraction of heparanase isolated from human hepatoma cells was subjected to tryptic digestion. Peptides were separated by high pressure liquid chromatography (HPLC) and micro sequenced. The sequence of one of the peptides was used to screen data bases for homology to the corresponding back translated DNA sequence. This procedure led to the identification of a clone containing an insert of 1020 base pairs (bp) which included an open reading frame of 963 bp followed by 27 bp of 3' untranslated region and a poly A tail. The new gene was designated hpa. Cloning of the missing 5' end of hpa was performed by PCR amplification of DNA from placenta cDNA composite. The joined hpa cDNA (also referred to as phpa) fragment contained an open reading frame which encodes a polypeptide of 543 amino acids with a calculated molecular weight of 61,192 daltons. Cloning an extended 5' sequence was enabled from the human SK-hep1 cell line by PCR amplification using the Marathon RACE system. The 5' extended sequence of the SK-hep1 hpa cDNA was assembled with the sequence of the hpa cDNA isolated from human placenta. The assembled sequence contained an open reading frame which encodes a polypeptide of 592 amino acids with a calculated molecular weight of 66,407 daltons. The cloning procedures are described in length in U.S. patent application Ser. Nos. 08/922,170, 09/109,386, and 09/xxx,xxx, entitled POLYNUCLEOTIDE ENCODING A POLYPEPTIDE HAVING HEPARANASE ACTIVITY AND EXPRESSION OF SAME IN GENETICALLY MODIFIED CELLS, which is a continuation-in-part of PCT/US98/17954, filed Aug. 31, 1998, all of which are incorporated herein by reference.

The ability of the hpa gene product to catalyze degradation of heparan sulfate (HS) in vitro was examined by expressing the entire open reading frame of hpa in High five and Sf21 insect cells, and the mammalian human 293 embryonic kidney cell line expression systems. Extracts of infected cells were assayed for heparanase catalytic activity. For this purpose, cell lysates were incubated with sulfate labeled, ECM-derived HSPG (peak I), followed by gel filtration analysis (Sepharose 6B) of the reaction mixture. While the substrate alone consisted of high molecular weight material, incubation of the HSPG substrate with lysates of cells infected with hpa containing virus resulted in a complete conversion of the high molecular weight substrate into low molecular weight labeled heparan sulfate degradation fragments (see, for example, U.S. patent application Ser. No. 09/071,618, which is incorporated herein by reference.

In subsequent experiments, the labeled HSPG substrate was incubated with the culture medium of infected High Five and Sf21 cells. Heparanase catalytic activity, reflected by the conversion of the high molecular weight HSPG substrate into low molecular weight HS degradation fragments, was found in the culture medium of cells infected with the pFhpa virus, but not the control pF1 virus.

Altogether, these results indicate that the heparanase enzyme is expressed in an active form by cells infected with Baculovirus or mammalian expression vectors containing the newly identified human hpa gene.

In other experiments, it was demonstrated that the heparanase enzyme expressed by cells infected with the pFhpa virus is capable of degrading HS complexed to other macromolecular constituents (e.g., fibronectin, laminin, collagen) present in a naturally produced intact ECM (see U.S. patent application Ser. No. 09/109,386, which is incorporated herein by reference), in a manner similar to that reported for highly metastatic tumor cells or activated cells of the immune system (7, 8)

Involvement of Heparanase in Tumor Cell Invasion and Metastasis

Circulating tumor cells arrested in the capillary beds often attach at or near the intercellular junctions between adjacent endothelial cells. Such attachment of the metastatic cells is followed by rupture of the junctions, retraction of the endothelial cell borders and migration through the breach in the endothelium toward the exposed underlying base membrane (BM) (24). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (25). Among these enzymes is heparanase that cleaves HS at specific intrachain sites (16,11). Expression of a HS degrading heparanase was found to correlate with the metastatic potential of mouse lymphoma (26), fibrosarcoma and melanoma (21) cells. Moreover, elevated levels of heparanase were detected in sera from metastatic tumor bearing animals and melanoma patients (21) and in tumor biopsies of cancer patients (12).

The inhibitory effect of various non-anticoagulant species of heparin on heparanase was examined in view of their potential use in preventing extravasation of blood-borne cells. Treatment of experimental animals with heparanase inhibitors markedly reduced (>90%) the incidence of lung metastases induced by B16 melanoma, Lewis lung carcinoma and mammary adenocarcinoma cells (12, 13, 28). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide (12).

Finally, heparanase externally adhered to B16-F1 melanoma cells increased the level of lung metastases in C57BL mice as compared to control mice (see U.S. patent application Ser. No. 09/xxx,xxx, entitled INTRODUCING A BIOLOGICAL MATERIAL INTO A PATIENT, which is a continuation in part of U.S. patent application Ser. No. 09/140,888, and is incorporated herein by reference.

Possible Involvement of Heparanase in Tumor Angiogenesis

Fibroblast growth factors are a family of structurally related polypeptides characterized by high affinity to heparin (29). They are highly mitogenic for vascular endothelial cells and are among the most potent inducers of neovascularization (29–30). Basic fibroblast growth factor (bFGF) has been extracted from a subendothelial ECM produced in vitro (31) and from basement membranes of the cornea (32), suggesting that ECM may serve as a reservoir for bFGF. Immunohistochemical staining revealed the localization of bFGF in basement membranes of diverse tissues and blood vessels (23). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (33, 32, 34). It was demonstrated that heparanase activity expressed by platelets, mast cells, neutrophils, and lymphoma cells is involved in release of active bFGF from ECM and basement membranes (35), suggesting that heparanase activity may not only function in cell migration and invasion, but may also elicit an indirect neovascular response. These results suggest that the ECM HSPG provides a natural storage depot for bFGF and possibly other heparin-binding growth promoting factors (36,37). Displacement of bFGF from its storage within basement membranes and ECM may therefore provide a novel mechanism for induction of neovascularizafion in normal and pathological situations.

Recent studies indicate that heparin and HS are involved in binding of bFGF to high affinity cell surface receptors and in bFGF cell signaling (38, 39). Moreover, the size of HS required for optimal effect was similar to that of HS fragments released by heparanase (40). Similar results were obtained with vascular endothelial cells growth factor (VEGF) (41), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (36,37).

Recombinant Heparanase for Screening Purposes

Put together, the accumulated evidences indicate that a reliable and high throughput (HTS) screening system for heparanase inhibiting compounds may be applied to identify and develop non-toxic drugs for the treatment of cancer and metastasis. Research aimed at identifying and developing inhibitors of heparanase catalytic activity has been handicapped by the lack of a consistent and constant source of a purified and highly active heparanase enzyme and of a reliable screening system. Such a HTS system is described in U.S. patent application Ser. No. 09/113,168, which is incorporated herein by reference. To this end, however, methods are required for obtaining high quantities of highly pure and active heparanase, so as to enable to study the kinetics of heparanase per se and in the presence of potential inhibitors. The recent cloning, expression and purification of the human heparanase-encoding gene offer, for the first time, a most appropriate and reliable source of active recombinant enzyme for screening of anti-heparanase antibodies and compounds which may inhibit the enzyme and hence be applied to identify and develop drugs that may inhibit tumor metastasis, autoimmune and inflammatory diseases.

Screening for Specific Inhibitors using a Combinatorial Library

A new approach aimed at rational drug discovery was recently developed for screening for specific biological activities. According to the new approach, a large library of chemically diverged molecules are screened for the desired biological activity. The new approach has become an effective and hence important tool for the discovery of new drugs. The new approach is based on "combinatorial" synthesis of a diverse set of molecules in which several components predicted to be associated with the desired biological activity are systematically varied. The advantage of a combinatorial library over the alternative use of natural extracts for screening for desired biologically active compounds is that all the components comprising the library are known in advance (60).

In combinatorial screening, the number of hits discovered is proportional to the number of molecules tested. This is true even when knowledge concerning the target is unavailable. The large number of compounds, which may reach thousands of compounds tested per day, can only be screened, provided that a suitable assay involving a high throughput screening technique, in which laboratory automation and robotics may be applied, exists.

Expression of Heparanase by Cells of the Immune System

Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity (10). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions (42).

Treatment of experimental animals with heparanase alternative substrates (e.g., non-anticoagulant species of low molecular weight heparin) markedly reduced the incidence of experimental autoimmune encephalomyelitis (EAE), adjuvant arthritis and graft rejection (10, 43) in experimental animals, indicating that heparanase inhibitors may be applied to inhibit autoimmune and inflammatory diseases (10,43).

The Involvement of Heparanase in Other Physiological Processes and its Potential Therapeutic Applications Apart from its involvement in tumor cell metastasis, inflammation and autoimmunity, mammalian heparanase may be applied to modulate bioavailability of heparin-binding growth factors (45); cellular responses to heparin-binding growth factors (e.g., bFGF, VEGF) and cytokines (IL-8) (44, 41); cell interaction with plasma lipoproteins (49); cellular susceptibility to certain viral and some bacterial and protozoa infections (45–47); and disintegration of amyloid plaques (48).

Viral Infection: The presence of heparan sulfate on cell surfaces have been shown to be the principal requirement for the binding of Herpes Simplex (45) and Dengue (46) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (45). There are some indications that the cell surface heparan sulfate is also involved in HIV infection (47).

Neurodegenerative diseases: Heparan sulfate proteoglycans were identified in the prion protein amyloid plaques of Genstmann-Straussler Syndrome, Creutzfeldt-Jakob disease and Scrape (48). Heparanase may disintegrate these amyloid plaques which are also thought to play a role in the pathogenesis of Alzheimer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (50). Apart from its involvement in SMC proliferation as a low affinity receptor for heparin-binding growth factors, HS is also involved in lipoprotein binding, retention and uptake (51). It was demonstrated that HSPG and lipoprotein lipase participate in a novel catabolic pathway that may allow substantial cellular and interstitial accumulation of cholesterol rich lipoproteins (49). The latter pathway is expected to be highly atherogenic by promoting accumulation of apoB and apoE rich lipoproteins (e.g., LDL, VLDL, chylomicrons), independent of feed back inhibition by the cellular cholesterol content. Removal of SMC HS by heparanase is therefore expected to inhibit both SMC proliferation and lipid accumulation and thus may halt the progression of restenosis and atherosclerosis.

In summary, Heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids. Common use in basic research is expected.

ECM Proteases and their Involvement in Tumor Progression and Metastasis

The cooperation with pericellular proteolysis cascades is required for vascular remodeling during angiogenesis, inflammatory processes, tumor progression and metastasis. In particular, the invasive processes that occur during tumor progression—local invasion, intravasation, extravasation and metastasis formation—involve extracellular matrix (ECM) degradation by proteases.

Four classes of proteases, are known to correlate with malignant phenotype: (i) cysteine proteases including cathepsin B and L; (ii) aspartyl protease cathepsin D; (iii) serine proteases including plasmin, tissue-type plasminogen activator (tPA) and urokinase-type plasminogen activator (uPA), (iv) Matrix metalloproteinases (MMPs) including collagenases, gelatinases A and B (MMP2 and MMP9) and stromelysin (MMP3).

Cathepsins are a family of proteases that are found inside cells in normal physiological conditions. Secretion of cathepsins correlates with various pathological conditions, such as arthritis, Alzheimer's disease and cancer progression (52).

The lysosomal cystein proteases cthepsin B and L have been suggested to play a role in tumor cell invasion and spread, either by directly cleaving extracellular matrix proteins or indirectly by activating other proteases (53).

Cathepsin B was found to have elevated expression levels in cancer cells. Furthermore, the intracellular distribution of the protein differed between invasive and non-invasive cancer cells. In invasive cells, cathepsin B was found in the plasma membrane, whereas in non-invasive cells it was confined to the lysosomes (56). In human tumor cells cathepsin B was secreted from the cells (53) and was shown to degrade extracellular matrix components (54). Cathepsin B and L have been shown to degrade type IV collagen, laminin and fibronectin in vitro at both acid and neutral pH (54). Both enzymes are able to activate the proenzyme form of the urokinase-type plasminogen activator (pro-uPA), which is secreted by tumor cells and can bind to receptors on the tumor cell surface (55). In this cascade mechanism, the lysosomal cysteine proteases may function as effective mediators of tumor associated proteolysis.

MMPs are a family of zinc dependent endopeptidases. They are secreted as inactive proenzymes and are activated by limited proteolysis (57). During human pregnancy, cytotrophoblasts adopt tumor-like properties: they attach the conceptus to the endometrium by invading the uterus and they initiate blood flow to the placenta by breaching maternal vessels. Matrix metalloproteinase MMP-9 (a type IV collagenase/gelatinase) was shown to be upregulated during cytotrophoblast differentiation along the invasive pathway. Furthermore, it was shown that the activity of that protease specified the ability of the cells to degrade ECM components in vitro (58).

Large body of evidence suggests that the matrix metalloproteinases MMP-2 and MMP-9 play an important role in tumor invasion process (59, 58).

There is clearly a widely recognized need for, and it would be highly advantageous to have, genetically modified cells overexpressing recombinant heparanase or modified species thereof, methods of overexpressing recombinant heparanase in cellular systems and methods of purifying recombinant heparanase, so as to enable, a search for heparanase inhibitors using a high throughput assay and a combinatorial approach.

SUMMARY OF THE INVENTION

According to one aspect of the present invention there is provided a recombinant cell comprising a polynucleotide sequence encoding a polypeptide having heparanase catalytic activity, the cell expressing recombinant heparanase.

According to a further aspect of the present invention, there is provided a method of obtaining recombinant heparanase comprising the steps of genetically modifying a cell with an expression vector including a polynucleotide sequence encoding a polypeptide having heparanase catalytic activity, the cell expressing recombinant heparanase.

According to still further features in the described preferred embodiments the polynucleotide sequence is as set forth in SEQ ID NO:1 or a functional part thereof, the part encodes the polypeptide having the heparanase catalytic activity.

According to still further features in the described preferred embodiments the polypeptide includes an amino acid sequence as set forth in SEQ ID NO:2 or a functional part thereof having the heparanase catalytic activity. The functional part may be the result of either genetic engineering natural processing by the transduced cell.

According to still further features in the described preferred embodiments the polynucleotide sequence is selected from the group consisting of double stranded DNA, single stranded DNA and RNA.

According to still further features in the described preferred embodiments the cell is a bacterial cell.

According to still further features in the described preferred embodiments the cell is *E. coli*.

According to still further features in the described preferred embodiments the cell is an animal cell.

According to still further features in the described preferred embodiments the animal cell is an insect cell.

According to still further features in the described preferred embodiments the insect cell is selected from the group consisting of High five and Sf21 cells.

According to still further features in the described preferred embodiments the animal cell is a mammalian cell, selected, for example, from the group consisting of a Chinese hamster ovary cell line (CHO), baby hamster kidney cells (BHK21), Namalwa cells, Dauidi cells, Raji cells, Human 293 cells, Hela cells, Ehrlich's ascites cells, Sk-Hep1 cells, $MDCK_1$ cells, $MDBK_1$ cells, Vero cells, Cos cells, CV-1 cells, NIH3T3 cells, L929 cells and BLG cells (mouse melanoma).

According to still further features in the described preferred embodiments the cell is a yeast cell.

According to still further features in the described preferred embodiments the yeast cell is a methylotrophic yeast.

According to still further features in the described preferred embodiments the yeast cell is selected from the group consisting of *Pichia pastoris, Hansenula polymorpha* and *Saccharomyces cerevisiae*.

According to still further features in the described preferred embodiments the heparanase is human recombinant heparanase.

According to still further features in the described preferred embodiments the polynucleotide sequence is integrated in the cell's genome rendering the cell a stably transduced.

According to still further features in the described preferred embodiments the polynucleotide sequence is external to the cell's genome, rendering the cell transiently transduced.

According to still further features in the described preferred embodiments the polynucleotide sequence forms a part of a viral genome infective to the cell, be it bacterial or animal cell.

According to still further features in the described preferred embodiments the polynucleotide sequence encodes, in addition, a signal peptide for protein secretion.

According to still further features in the described preferred embodiments the method further comprising the step of subjecting the cell to a substance which induces secretion into the growth medium of secretable proteins, thereby inducing secretion of the recombinant heparanase into the growth medium.

According to still further features in the described preferred embodiments the substance is selected from the group consisting of thrombin, calcium ionophores, immune complexes, antigens and mitogens.

According to still further features in the described preferred embodiments the calcium ionophore is calcimycin (A23187).

According to still further features in the described preferred embodiments the substance is phorbol 12-myristate 13-acetate (PMA).

According to still further features in the described preferred embodiments the method further comprising the step of purifying the recombinant heparanase.

According to still further features in the described preferred embodiments the purification is effected in part by an ion exchange (e.g., Source-S) column.

According to still further features in the described preferred embodiments the purification is from the cell.

According to still further features in the described preferred embodiments the purification is from a growth medium in which the cell is grown.

According to still further features in the described preferred embodiments the cell is grown in a large biotechnological scale of at least half a liter growth medium.

According to another aspect of the present invention provided is a method of purifying a recombinant heparanase from overexpressing cells or growth medium comprising the steps of adsorbing the recombinant heparanase on an ion exchange (e.g., Source-S) column under low salt conditions, washing the column with low salt solution thereby eluting other proteins, and eluting the recombinant heparanase from the column by a salt gradient or a higher salt concentration.

According to a further aspect of the present invention there is provided a method of activating a heparanase enzyme comprising the step of digesting the heparanase enzyme by a protease.

According to still further features in the described preferred embodiments the protease is selected from the group consisting of a cysteine protease, an aspartyl protease, a serine protease and a meatlloproteinase.

According to still further features in the described preferred embodiments the step of digesting the heparanase enzyme by a protease is effected at a pH in which the protease is active, preferably most active.

According to a further aspect of the present invention there is provided a method of in vivo inhibition of proteolytic processing of heparanase comprising the step of in vivo administering a protease inhibitor.

According to still further features in the described preferred embodiments the protease inhibitor is selected from the group consisting of a cysteine protease inhibitor, an aspartyl protease inhibitor, a serine protease inhibitor and a meatlloproteinase inhibitor.

According to a further aspect of the present invention there is provided a nucleic acid construct comprising a first nucleic acid segment encoding for an upstream portion of heparanase, a second, in frame, nucleic acid sequence encoding a recognition and cleavage sequence of a protease and a third, in frame, nucleic acid sequence encoding for a downstream portion of heparanase, wherein the second nucleic acid sequence is in between the first nucleic acid sequence and the third nucleic acid sequence.

According to still further features in the described preferred embodiments the protease is selected having no recognition and cleavage sequences in the upstream and the downstream portions of heparanase.

According to still further features in the described preferred embodiments the third nucleic acid sequence encodes for a catalytically active heparanase when correctly folded.

According to a further aspect of the present invention there is provided a precursor heparanase protein comprising an upstream portion of heparanase, a mid portion of a recognition and cleavage sequence of a protease and a downstream portion of heparanase, wherein the protease is selected having no recognition and cleavage sequences in the upstream and the downstream portions of heparanase.

According to a further aspect of the present invention there is provided a heparanase protein resulting by digesting the precursor heparanase protein described herein.

According to a further aspect of the present invention there is provided a method of obtaining a homogeneously processed, active heparanase, the method comprising the steps of (a) expressing the precursor heparanase protein in a cell which secretes the precursor heparanase protein into the growth medium to obtain a conditioned growth medium, the precursor heparanase protein including an upstream portion of heparanase, a mid portion of a recognition and cleavage sequence of a protease and a downstream portion of heparanase, wherein the protease is selected having no recognition and cleavage sequences in the upstream and the downstream portions of heparanase; (b) treating the precursor heparanase protein with the protease; and (c) purifying a proteolytic heparanase product having heparanase catalytic activity.

According to a further aspect of the present invention there is provided an antibody comprising an immunoglobulin elicited against recombinant native heparanase.

According to a further aspect of the present invention there is provided an affinity substrate comprising a solid matrix and an immunoglobulin elicited against recombinant native heparanase being immobilized thereto.

According to a further aspect of the present invention there is provided a method of affinity purifying heparanase comprising the steps of (a) loading a heparanase preparation on an affinity substrate including a solid matrix and an immunoglobulin elicited against recombinant native heparanase being immobilized thereto; (b) washing the affinity substrate; and (c) eluting heparanase molecules being adsorbed on the affinity substrate via the immunoglobulin.

The present invention successfully addresses the shortcomings of the presently known configurations by providing cells and methods for expressing recombinant heparanase, methods for purifying the recombinant heparanase and modified heparanase precursor species which can be processed to yield highly active heparanase. Other features and advantages of the various embodiments of the present invention are further addressed hereinunder.

BRIEF DESCRIPTION OF THE DRAWINGS

The invention herein described, by way of example only, with reference to the accompanying drawings, wherein:

FIG. 6a—CHO stable cellular clones (lanes 1–3) and transiently transfected 293 human cells (lane 4). FIG. 6b—Mock transfected CHO cells (lane 3), CHO cells performing stable or transient expression (lanes 1 and 2, respectively). Molecular size in kDa is shown to the right, as was determined using prestained SDS-PAGE standards, Bio-Rad, California.

FIGS. 8c–g show the relative heparanase activity of p70 and p52 (see FIGS. 8b-c) by comparing the ability of diluted (×2, ×4 or ×8) conditioned media to degrade $^{35}$S-ECM.

Figure 12:
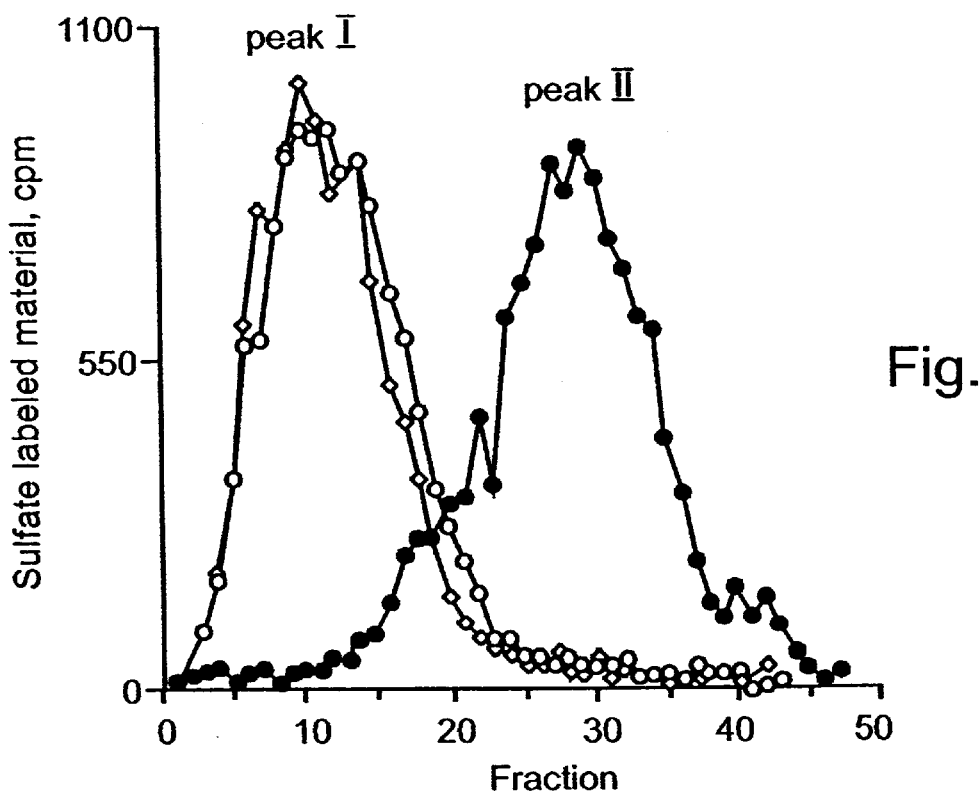

FIG. 12 presents size fractionation of heparanase activity expressed by pFhpa2 infected cells. Growth medium of pFhpa2 infected High five cells was applied onto a 50 kDa cut-off membrane. Heparanase activity (conversion of the peak I substrate, (◇) into peak II HS degradation fragments) was found in the high (>50 kDa) (●), but not low (<50 kDa) (○) molecular weight compartment.

Figure 13A:
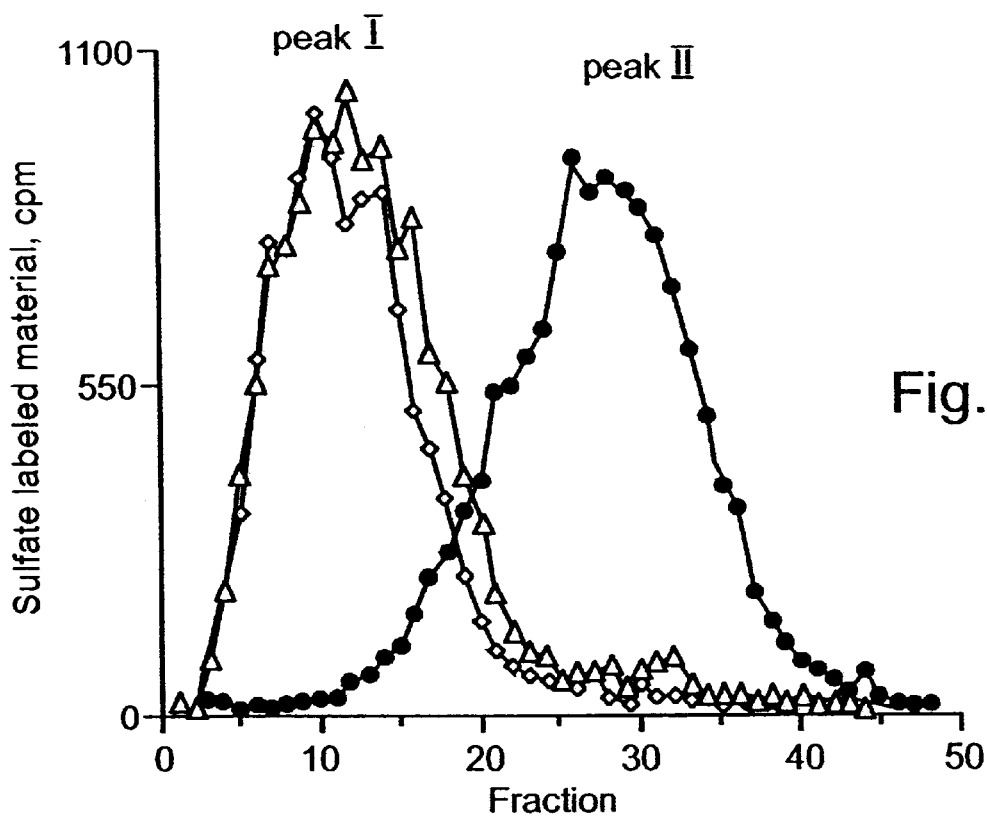
Figure 13B:
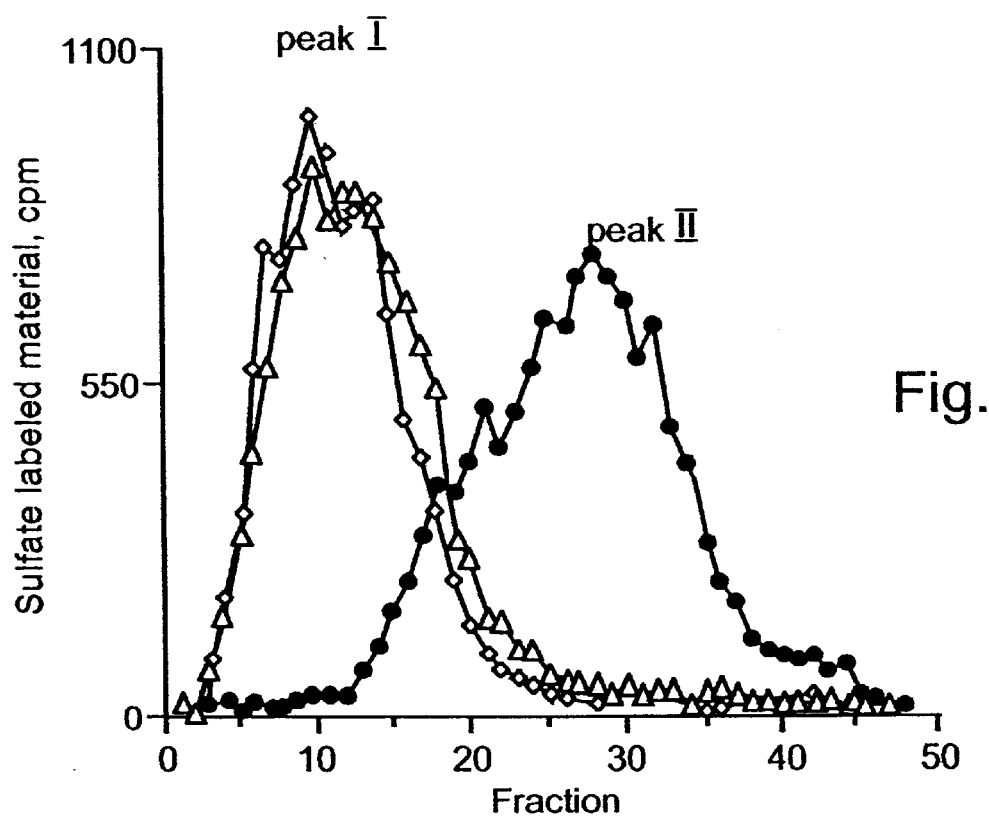

FIGS. 13a–b demonstrate the effect of heparin on heparanase activity expressed by pFhpa2 and pFhpa4 infected High five cells. Culture media of pFhpa2 (13a) and pFhpa4 (13b) infected High five cells were incubated (18 h, 37° C.) with sulfate labeled ECM-derived soluble HSPG (peak I, ◇) in the absence (●) or presence (Δ) of 10 μg/ml heparin. Production of low molecular weight HS degradation fragments was completely abolished in the presence of heparin, a potent competitor for heparanase activity.

Figure 14A:
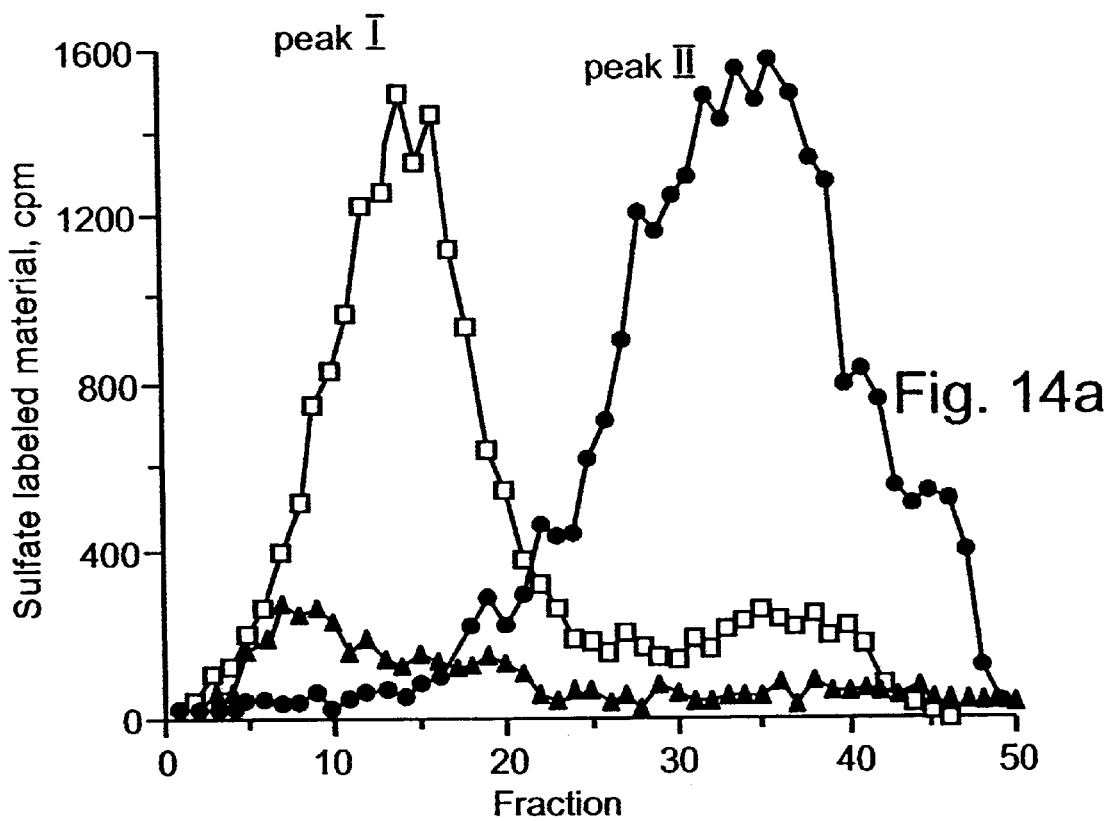
Figure 14B:
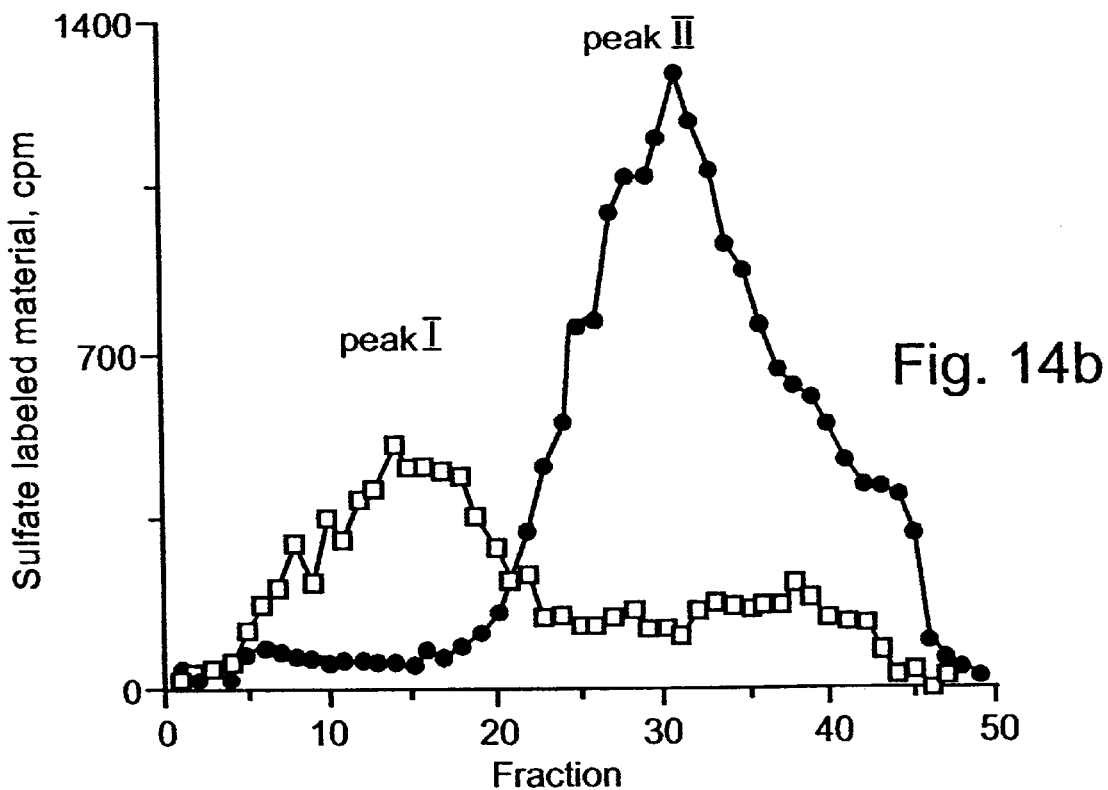

FIGS. 14a–b demonstrate degradation of sulfate labeled intact ECM by virus infected High five and Sf21 cells. High five (14a) and Sf21 (14b) cells were plated on sulfate labeled ECM and infected (48 h, 28° C.) with pFhpa4 (●) or control pF1 (□) viruses. Control non-infected Sf21 cells (R) were plated on the labeled ECM as well. The pH of the cultured medium was adjusted to 6.0–6.2 followed by 24 h incubation at 37° C. Sulfate labeled material released into the incubation medium was analyzed by gel filtration on Sepharose 6B. HS degradation fragments were produced only by cells infected with the hpa containing virus.

Figure 15A:
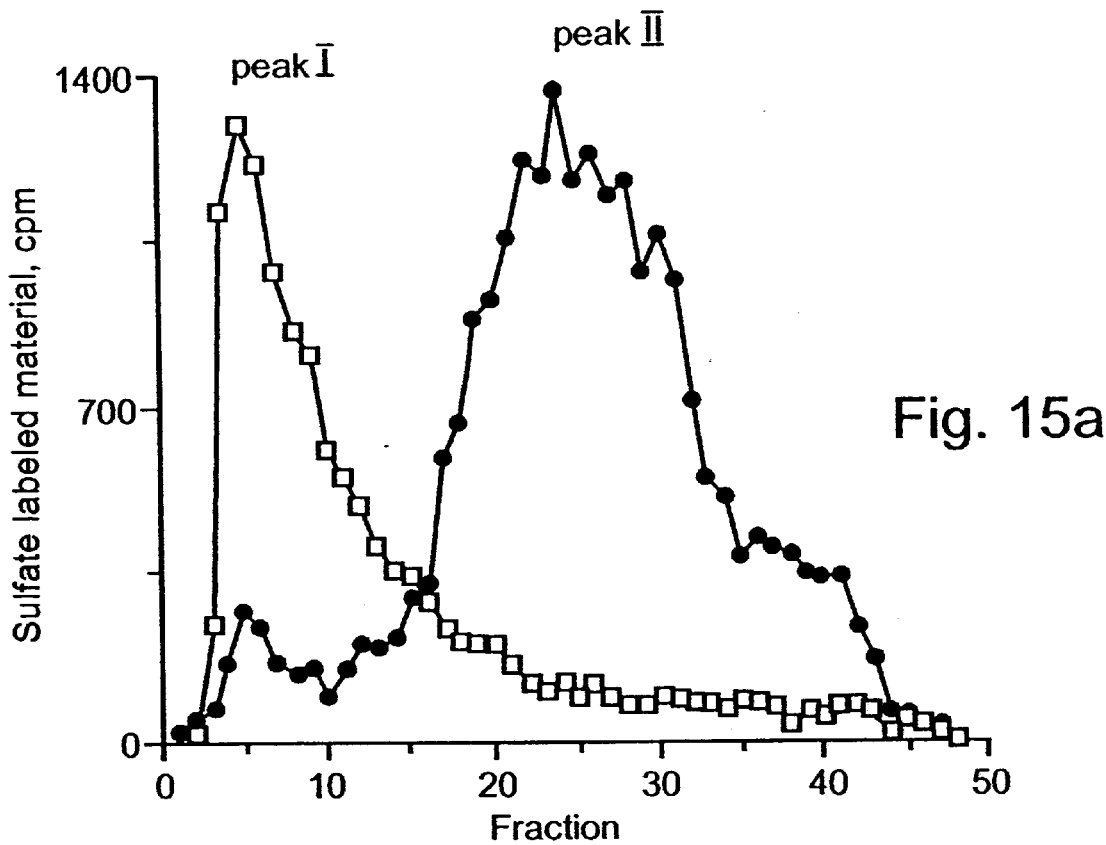
Figure 15B:
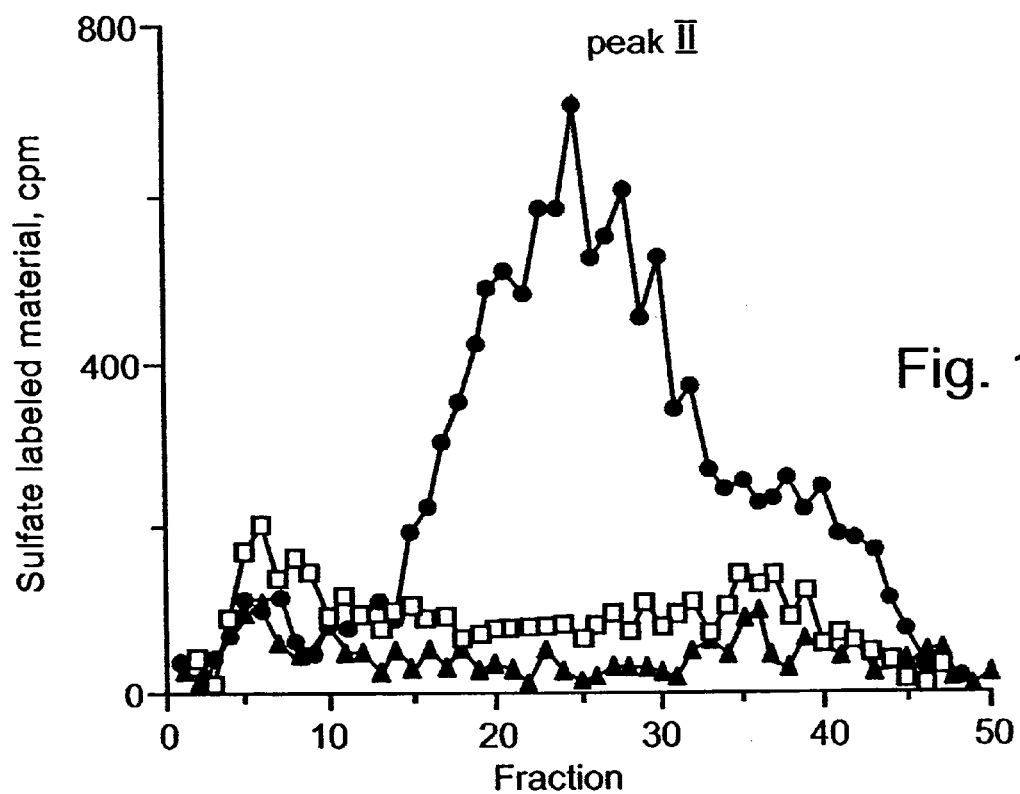

FIGS. 15a–b demonstrate degradation of sulfate labeled intact ECM by virus infected cells. High five (15a) and Sf21 (15b) cells were plated on sulfate labeled ECM and infected (48 h, 28° C.) with pFhpa4 (●) or control pF1 (□) viruses. Control non-infected Sf21 cells (R) were plated on labeled ECM as well. The pH of the cultured medium was adjusted to 6.0–6.2, followed by 48 h incubation at 28° C. Sulfate labeled degradation fragments released into the incubation medium was analyzed by gel lo filtration on Sepharose 6B. HS degradation fragments were produced only by cells infected with the hpa containing virus.

Figure 16A:
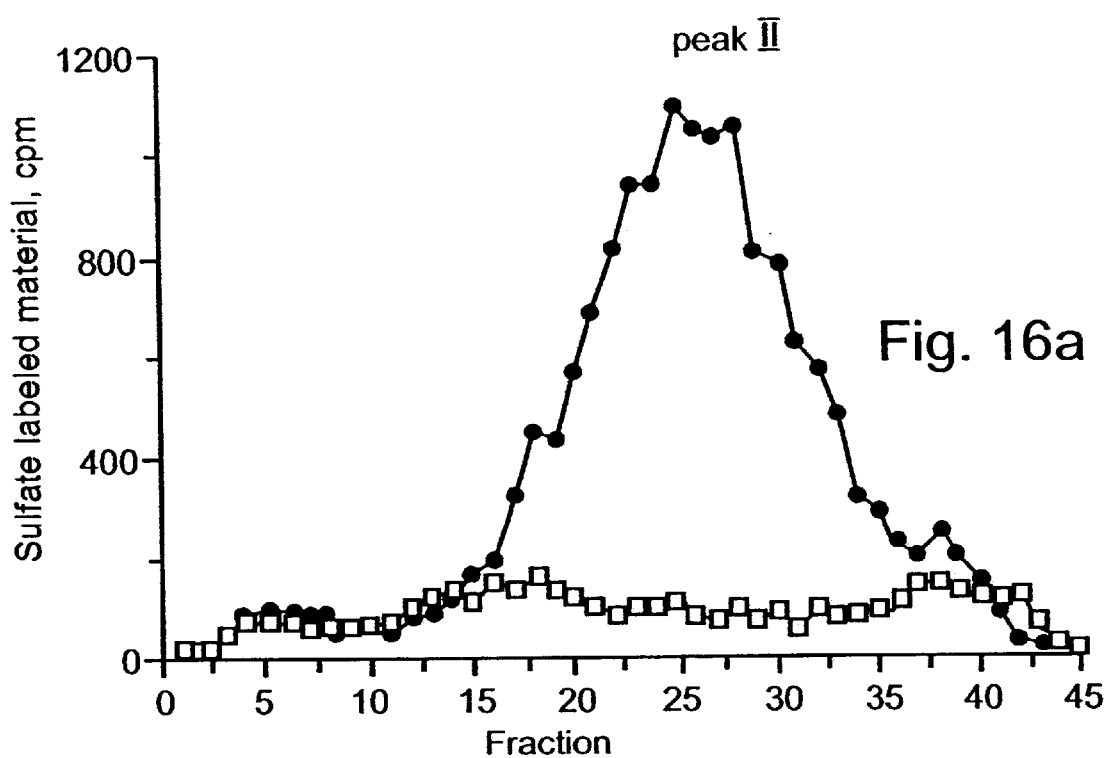
Figure 16B:
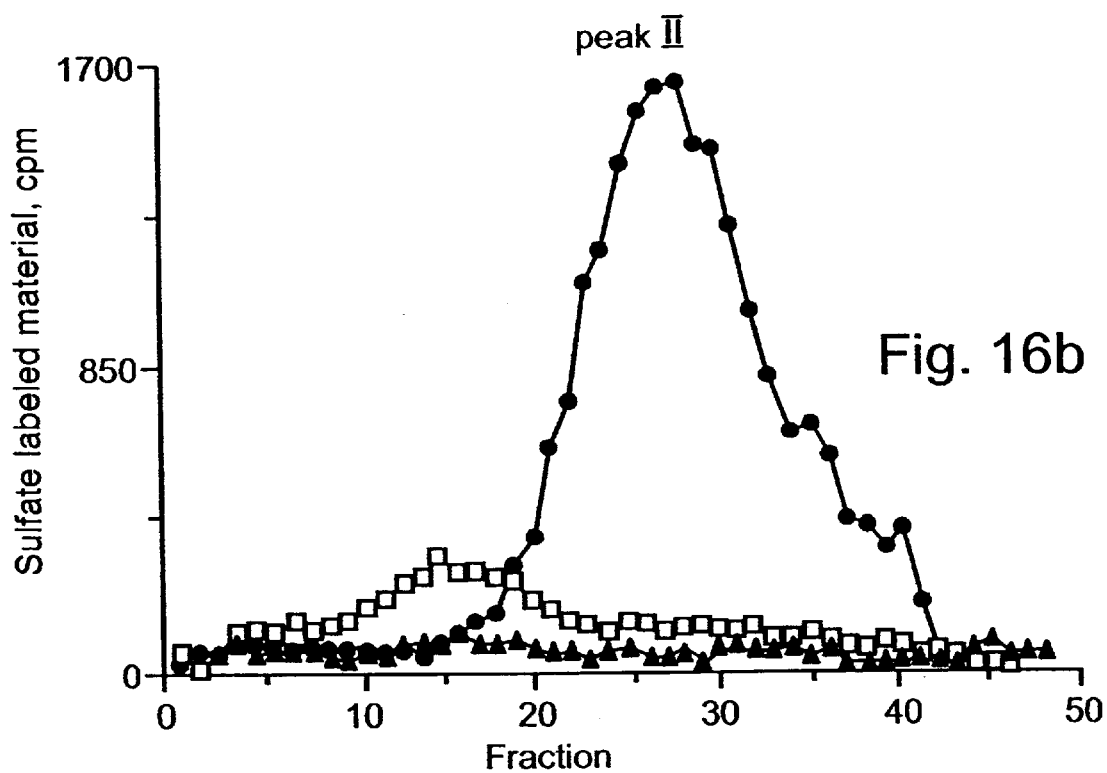

FIGS. 16a–b demonstrate degradation of sulfate labeled intact ECM by the growth medium of pFhpa4 infected cells. Culture media of High five (16a) and Sf21 (16b) cells that were infected with pFhpa4 (●) or control pF1 (□) viruses were incubated (48 h, 37° C., pH 6.0) with intact sulfate labeled ECM. The ECM was also incubated with the growth medium of control non-infected Sf21 cells (R). Sulfate labeled material released into the reaction mixture was subjected to gel filtration analysis. Heparanase activity was detected only in the growth medium of pFhpa4 infected cells.

Figure 17A:
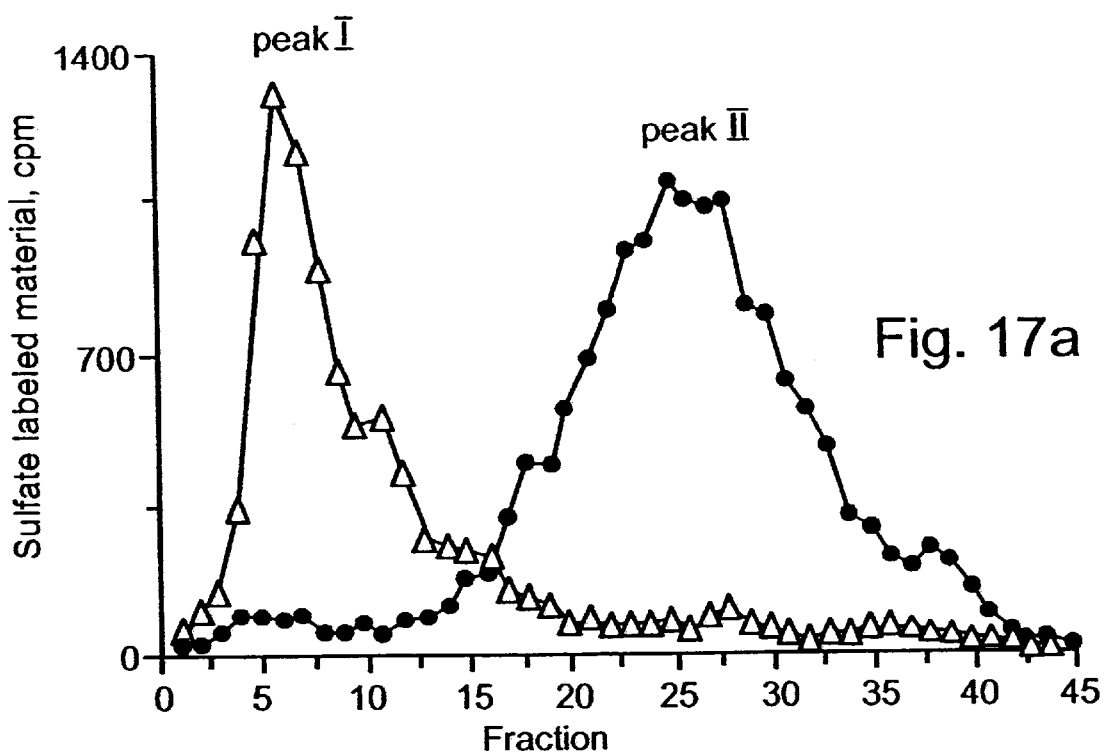
Figure 17B:
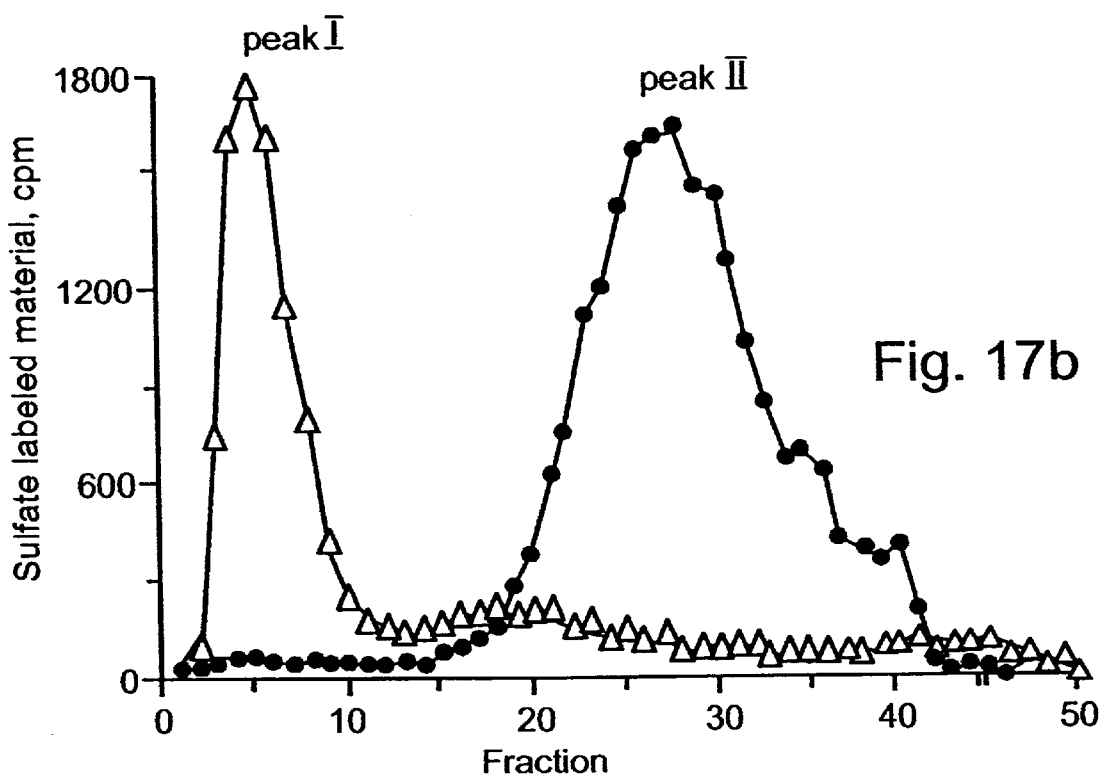

FIGS. 17a–b demonstrate the effect of heparin on heparanase activity in the growth medium of pFhpa4 infected cells. Sulfate labeled ECM was incubated (24 h, 37° C., pH 6.0) with growth medium of pFhpa4 infected High five (17a) and Sf12 (17b) cells in the absence (●) or presence (V) of 10 μg/ml heparin. Sulfate labeled material released into the incubation medium was subjected to gel filtration on Sepharose 6B. Heparanase activity (production of peak II HS degradation fragments) was completely inhibited in the presence of heparin.

Figure 18:
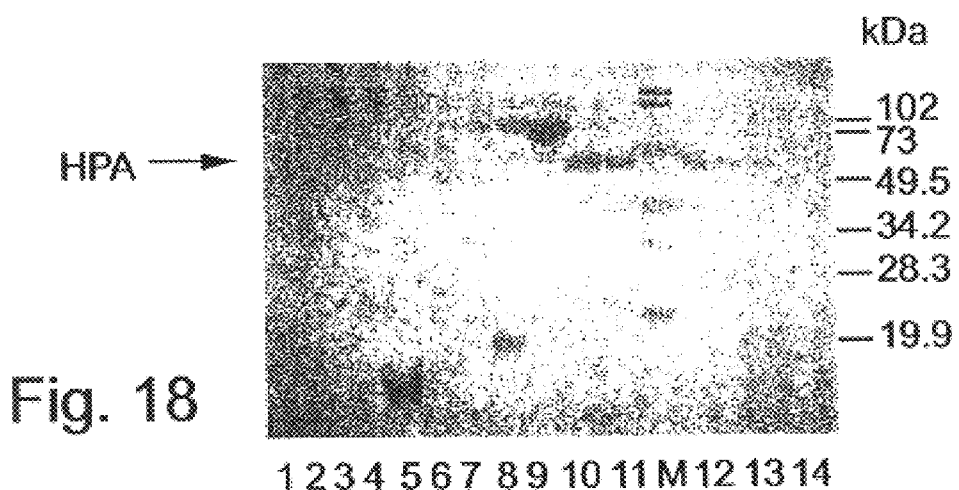

FIG. 18 demonstrate the purification of recombinant heparanase by a Source-S column. Lanes 1–14, 40 ml of fractions 1–14 eluted from a Source-S column. Samples were analyzed on 8–16% gradient SDS-PAGE.

Gel was stained with commassie blue.

Figure 19:
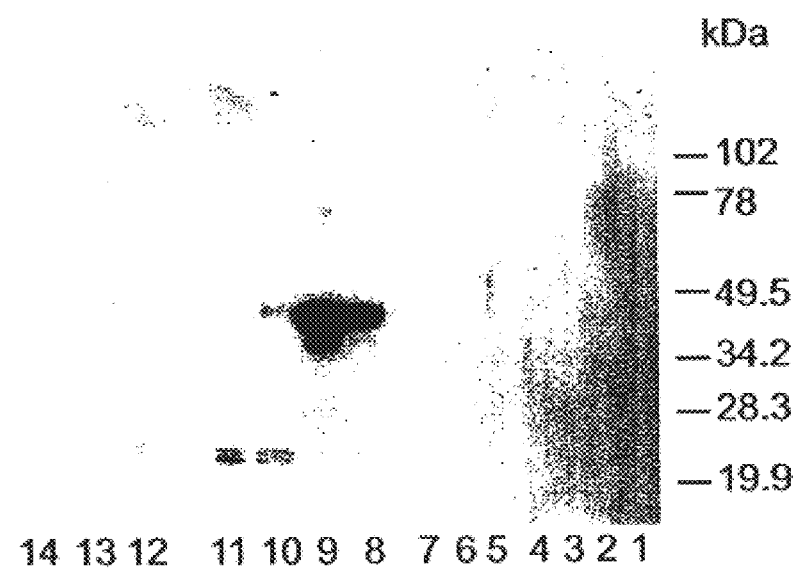

FIG. 19 demonstrate Western blot analysis of fractions 1–14 of FIG. 18. Fractions 1–14 eluted from a Source-S column were analyzed following blotting onto nitrocellulose membrane with a rabbit anti-heparanase polyclonal antibody (disclosed in U.S. patent application Ser. No. 09/071,739) followed by ECL detection (Amersham, UK).

Figure 20:
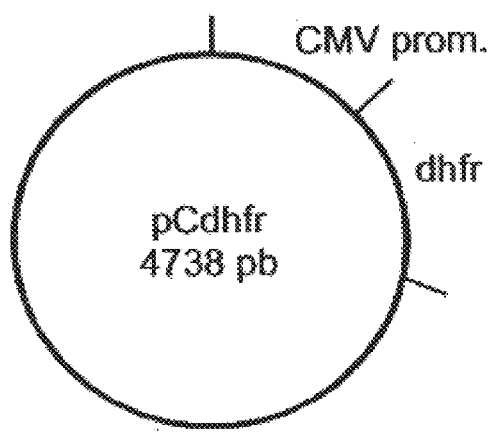

FIG. 20 is a schematic presentation of plasmid pCdhfr that contains the mouse dhfr gene under CMV promoter regulation. This vector does not express heparanase and serves as negative control.

Figure 21A:
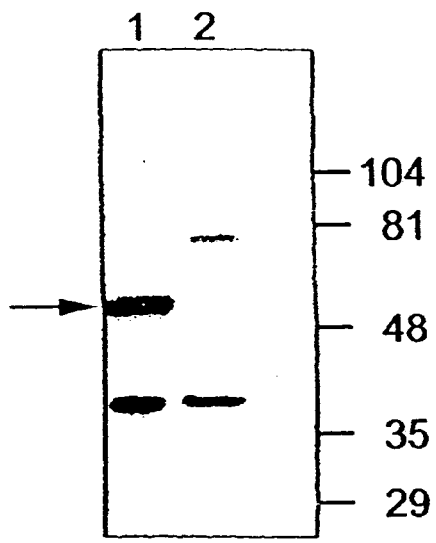

FIG. 21a demonstrates the production of heparanase in pS1hpa transfected BHK21 cells. Cell extracts ($2\times10^5$ BHK21 cells) were separated on 8–16% gradient SDS-PAGE and transferred to PVDF membranes. Detection of hpa gene products was performed with a mouse anti-heparanase monoclonal antibody No. HP-117 (disclosed in U.S. patent application Ser. No. 09/071,739) followed by ECL detection (Amersham, UK). Molecular size in kDa is shown to the right, as was determined using prestained SDS-PAGE PAGE standards, Bio-Rad, California. Lane 1 pS1hpa transfected BHK21 cells. Lane 2 control, pCdhfr transfected, BHK21 cells.

Figure 21B:
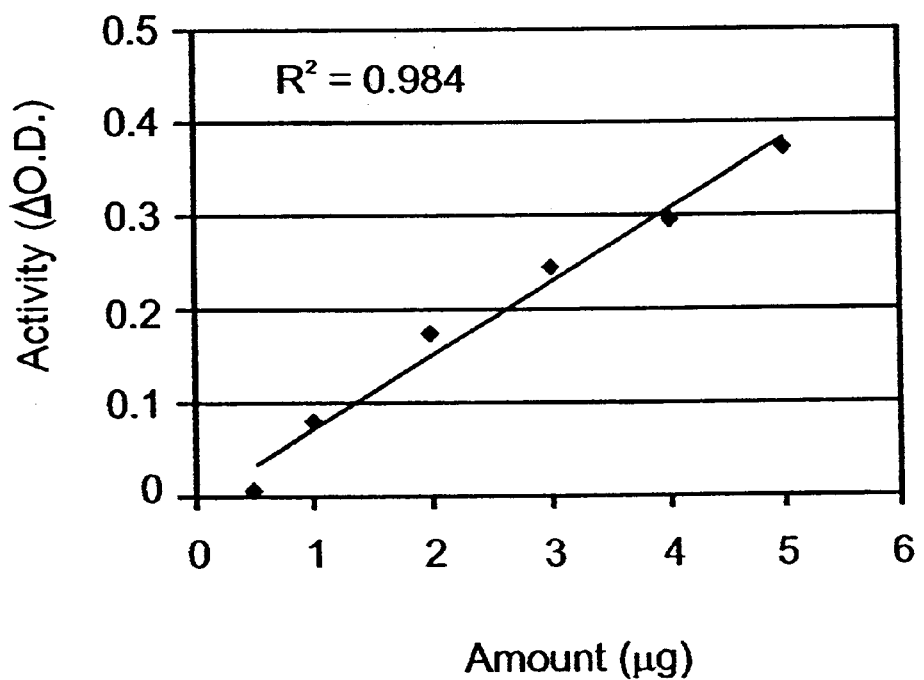

FIG. 21b demonstrates heparanase activity in human 293 cell extract. Cells were collected and concentrated by centrifugation (2750×g for 5 min). The pellets were passed through three cycles of 5 minutes freezing in liquid nitrogen and thawing at 37° C. Cell lysate was centrifuged for 15 minutes at 3000×g, and the supernatant was collected for analysis. Increasing amounts of supernatant, between 0 and 5 μg protein per assay were assayed using the DMB activity assay described herein (see also U.S. patent application Ser. No. 09/113,168).

Figure 22A:
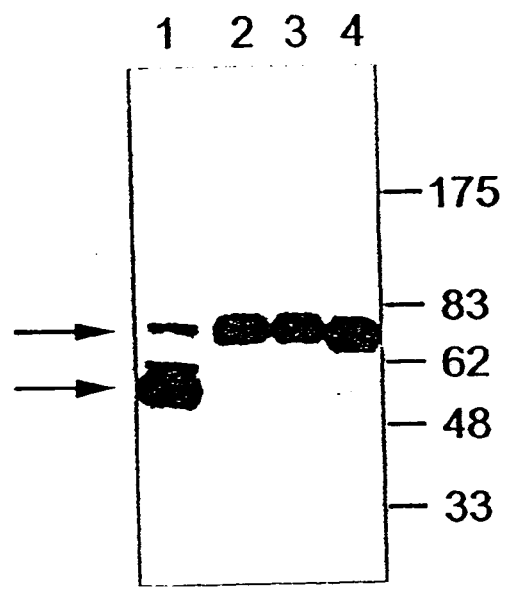

FIG. 22a demonstrates recombinant heparanase constitutive secretion by CHO cells transfected with pS1hpa (clone S1PPT-8). Conditioned media (20 μl) of untreated cells (lane 2), mock treated cells (lane 3) and calcium ionophore treated cells (0.1 μg/ml for 24 hours; lane 4) were electrophoresed next to a cellular extract of $1\times10^5$ cells from clone 2TT1 (CHO cells transfected with pShpaCdhfr, lane 1). Samples were separated on a 4–20% gradient SDS-PAGE, followed by Western blot analysis with a rabbit anti-heparanase polyclonal antibody (disclosed in U.S. patent application Ser. No. 09/071,739) and by ECL detection (Amersham, UK). Molecular size in kDa is shown on the right, as was determined using prestained SDS-PAGE standards, Bio-Rad, California.

Figure 22B:
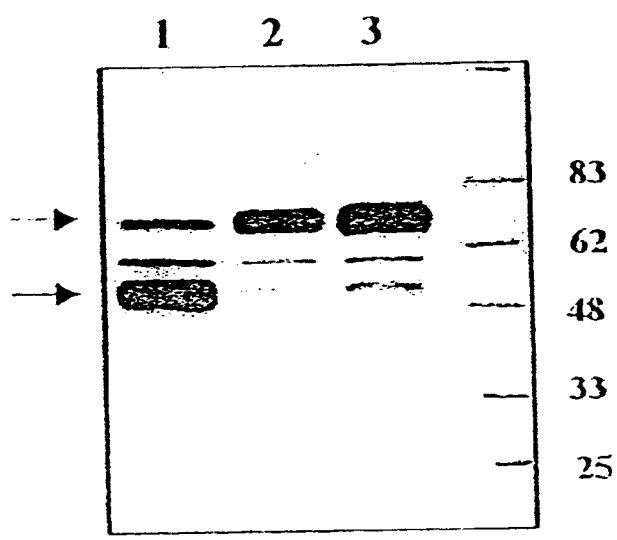

FIG. 22b demonstrates recombinant heparanase constitutive secretion by CHO cells transfected with pShpaCdhfr (2TT1 clones). Conditioned media (150 μl, concentrated by 10 kDa ultrafiltration tube) of 2TT1-2 clone (lane 2) and of clone 2TT1-8 (lane 3) were electrophoresed next to a cellular extract of $1\times10^5$ cells from clone 2TT1 (lane 1). Samples were separated on a 4–20% gradient SDS-PAGE, followed by Western blot analysis with a rabbit anti-heparanase polyclonal antibody (disclosed in U.S. patent application Ser. No. 09/071,739) and by ECL detection (Amersham, UK). Molecular size in kDa is shown on the right, as was determined using prestained SDS-PAGE standards, Bio-Rad, California.

Figure 23A:
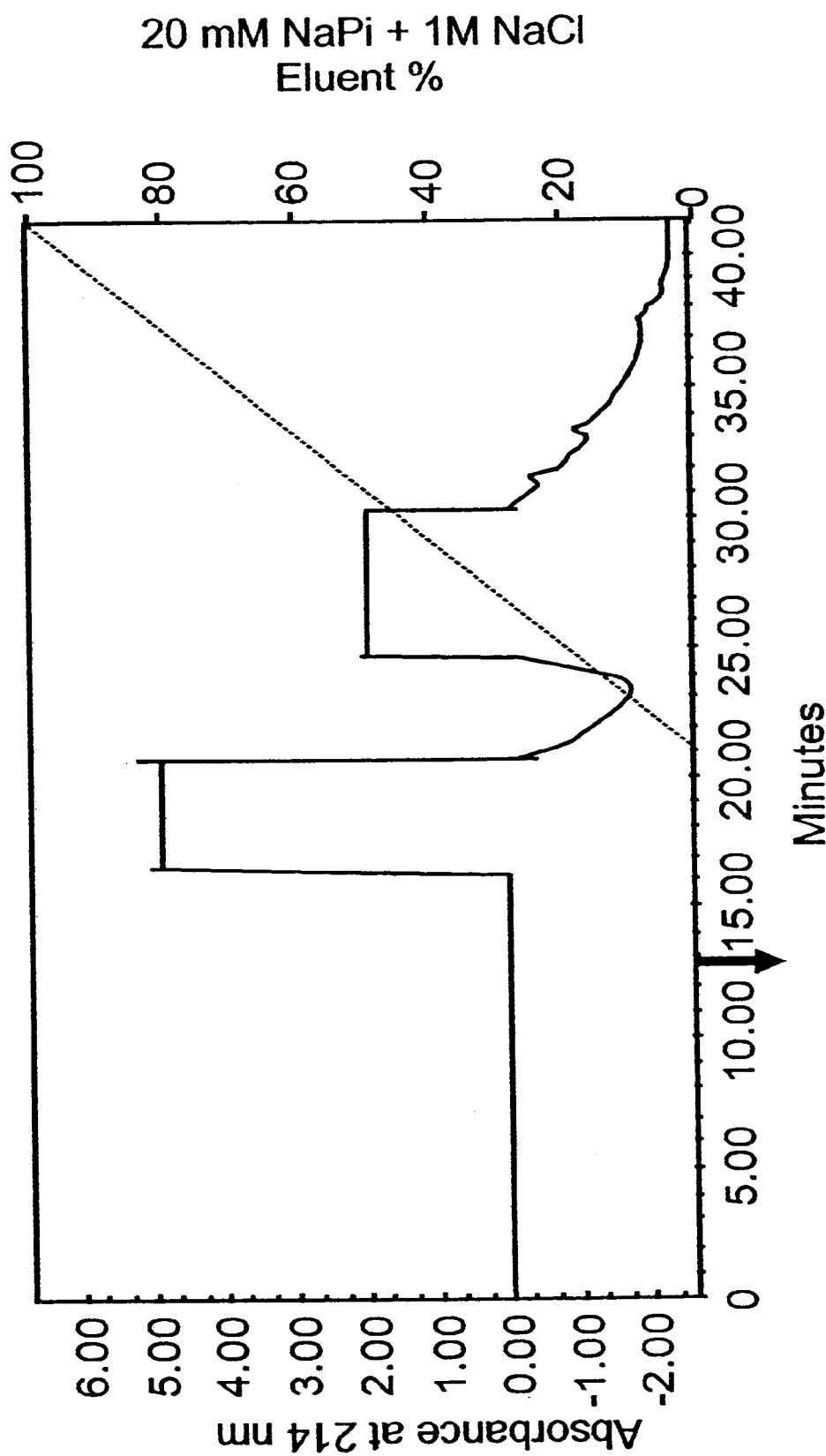

FIG. 23a demonstrates purification of recombinant heparanase from lo a mammalian cellular extract by ion exchange chromatography. 2TT1-8 CHO cells (1×10$^8$) were extracted in 2.5 ml of 10 mM phosphate citrate buffer pH 5.4. The extract was centrifuged at 2750×g for 5 minutes and the supernatant was collected for heparanase enzyme purification using a cation exchange chromatography column. The chromatography column (mono-S HR 5/5, Pharmacia Biotech) was equilibrated with 20 mM sodium phosphate buffer, pH 6.8, and the mixture was loaded atop thereof. Proteins were eluted from the column using a linear gradient of 0 to 1 M sodium chloride in 20 mM sodium phosphate buffer, pH 6.8. The gradient was carried out in 20 column volumes at a flow rate of one ml per minute. The elution of proteins was monitored at 214 nm and fractions of 1 ml each were collected, starting with the first fraction (1) which was eluted after 13 minutes and which is identified by the arrowhead mark.

Figure 23B:
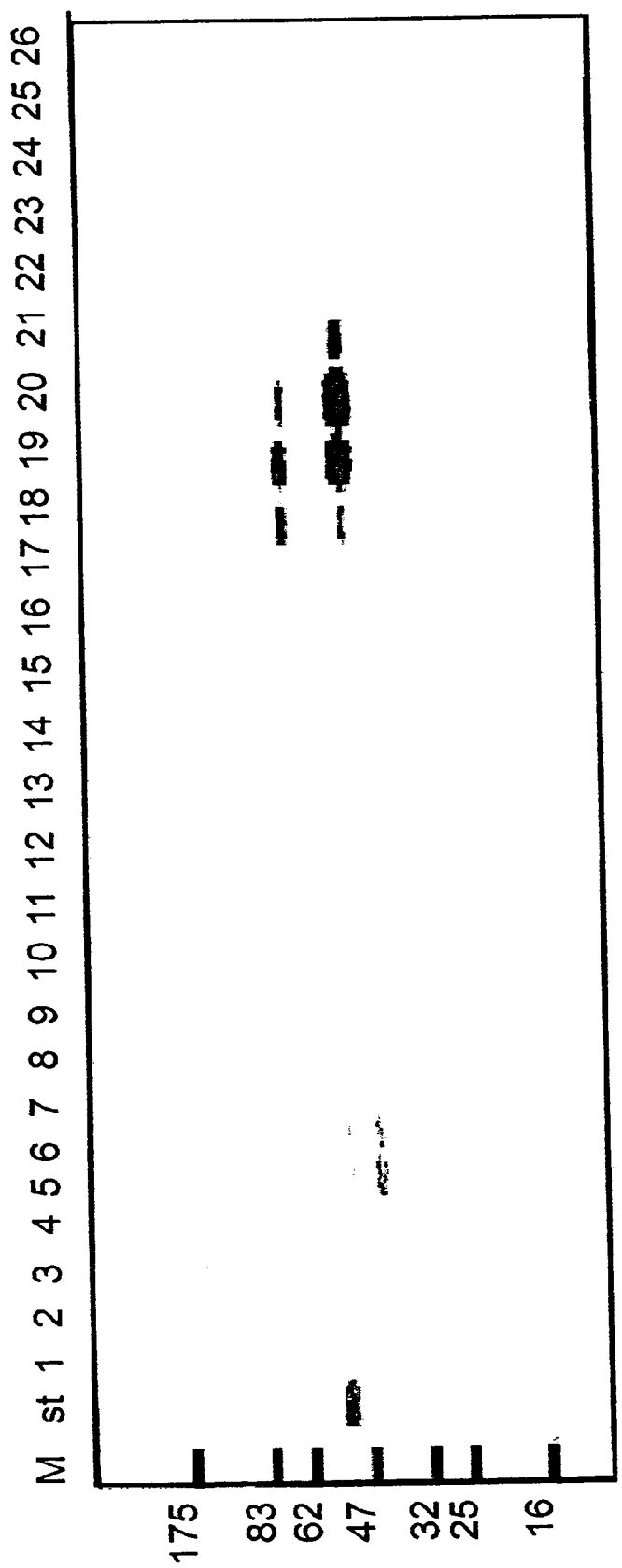

FIG. 23b demonstrates the presence of immunologically active recombinant heparanase in the mammalian cellular extract. An aliquot from each fraction that was collected was analyzed for the presence of the heparanase enzyme by Western blot analysis. 20 μl from each fraction, numbered 1–26, were separated on a 4–20% SDS-PAGE. The proteins were transferred from the gel to a PVDF membrane and were detected with a monoclonal antibody No. HP-117 (disclosed in U.S. patent application Ser. No. 09/071,739) followed by ECL detection (Amersham, UK). Molecular size in kDa is shown to the right, as was determined using SDS-PAGE standards (M). St—a purified recombinant heparanase enzyme from CHO cells.

Figure 23C:
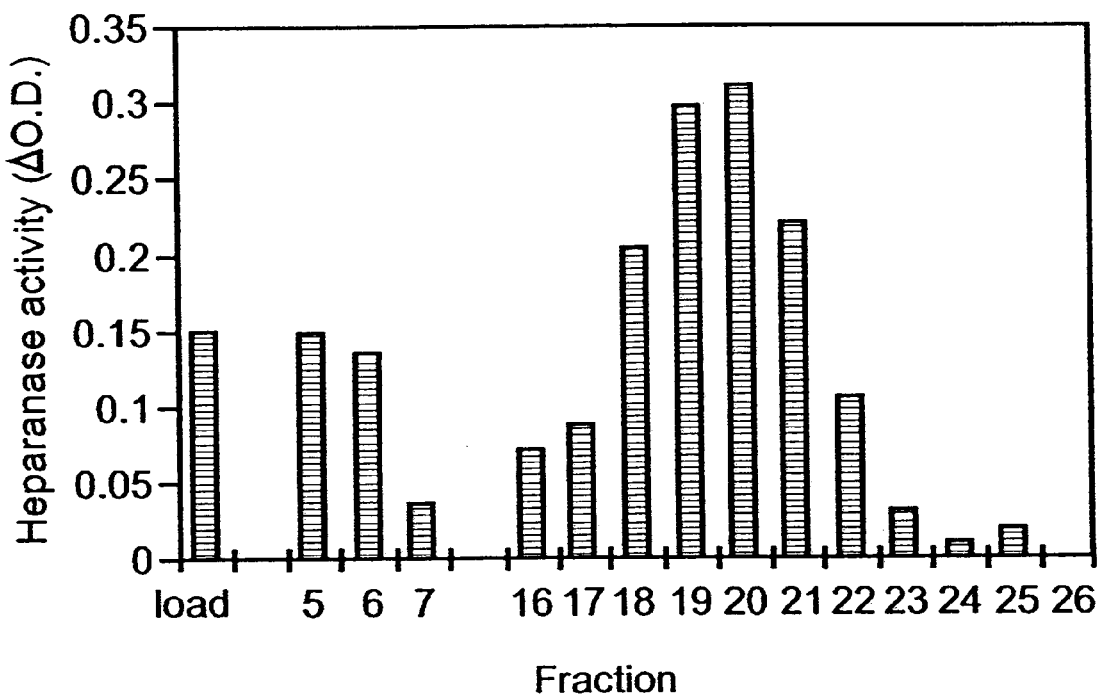

FIG. 23c demonstrates the presence of catalytically active recombinant heparanase in mammalian cellular extract fractions. An aliquot (30 μl) from each fraction that was collected was analyzed for heparanase activity by the DMB assay. Load—extract prior to purification. 5–7 and 16–26 correspond to fraction Nos.

Figure 23D:
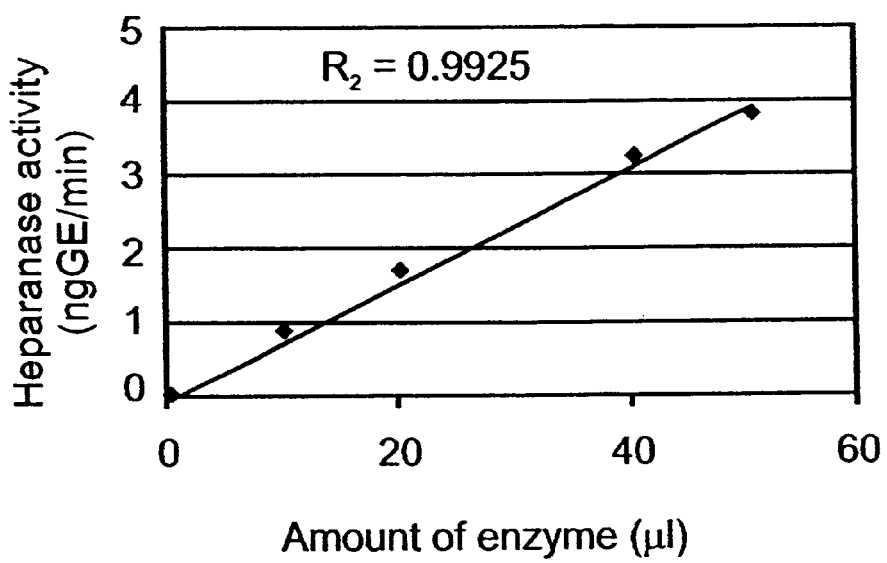

FIG. 23d demonstrates a heparanase dose response. Increasing amounts from fraction No. 20, which exhibited the highest activity using the DMB assay (FIG. 23c), were analyzed for heparanase activity using the tetrazolium assay, as disclosed in U.S. patent application Ser. No. 09/113,168.

Figure 24A:
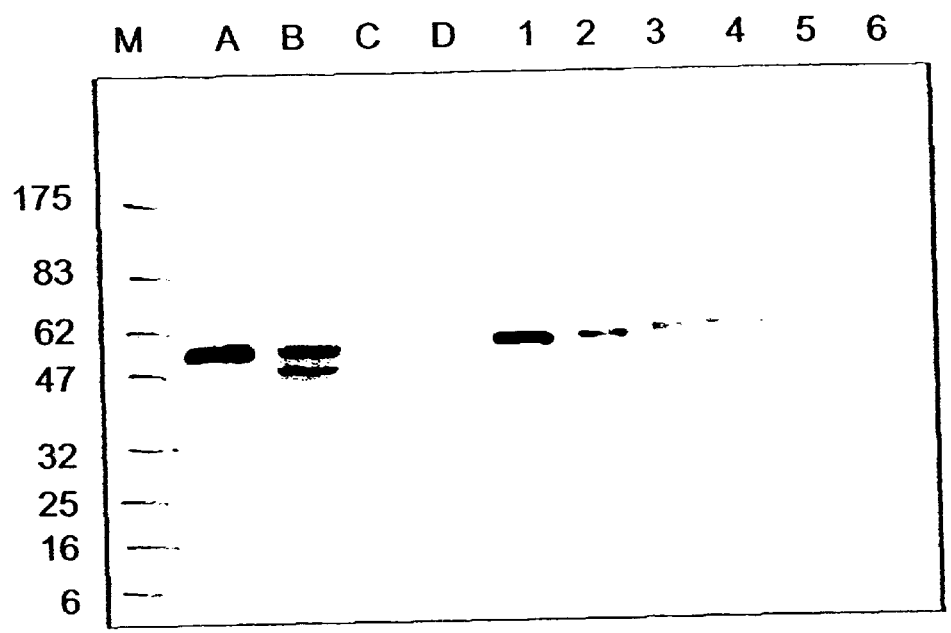

FIG. 24a demonstrates the purification of heparanase from a mammalian cellular extract by an affinity column. A cellular extract from CHO 2TT1-8 cells was loaded on an affinity column containing antibodies elicited against native (non-denatured) recombinant heparanase. Western blot analysis of different fractions (1–6) using a monoclonal antibody No. HP-117 (disclosed in U.S. patent application Ser. No. 09/071,739) followed by ECL detection (Amersham, UK) is shown. Molecular size in kDa is shown to the left, as was determined using SDS-PAGE standards (M). A—recombinant heparanase enzyme purified from CHO 2TT1-8 cells on mono-S column; B—extract of 2TT1-8 cells; C—unbound, flow through proteins; and D—wash fraction proteins.

Figure 24B:
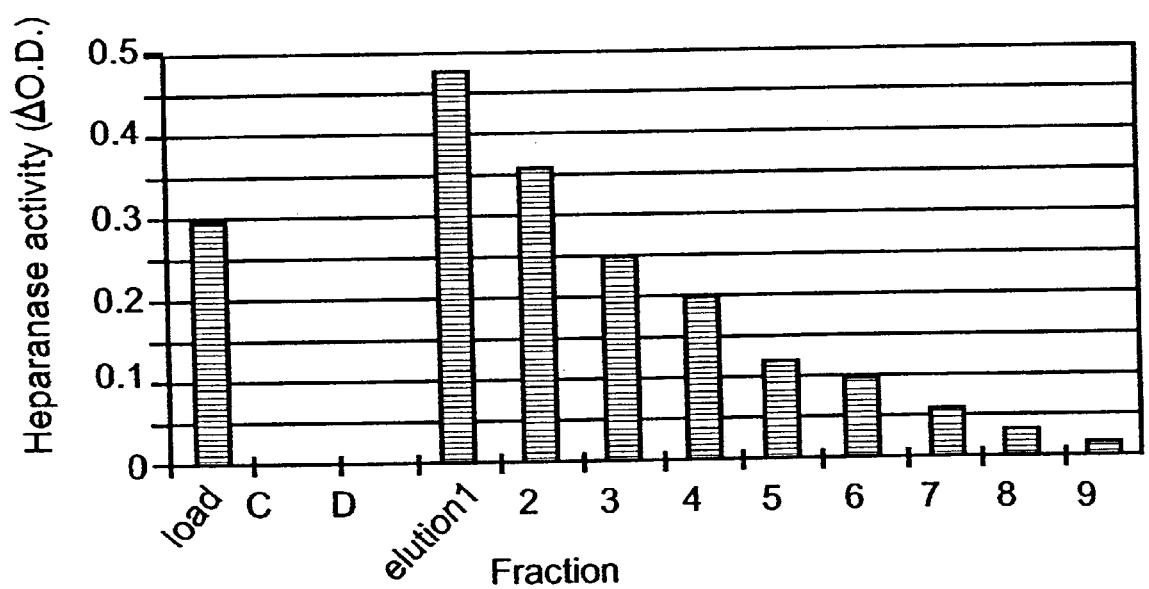

FIG. 24b demonstrates the purification of heparanase from a mammalian cellular extract by an affinity column. A cellular extract from CHO 2TT1-8 cells was loaded on an affinity column containing antibodies elicited against native (non-denatured) recombinant heparanase. Heparanase activity in affinity column fraction Nos. 1–9 was determined using the DMB assay. Load—extract prior to purification; C—unbound, flow through proteins; and D—wash fraction proteins.

Figure 25A:
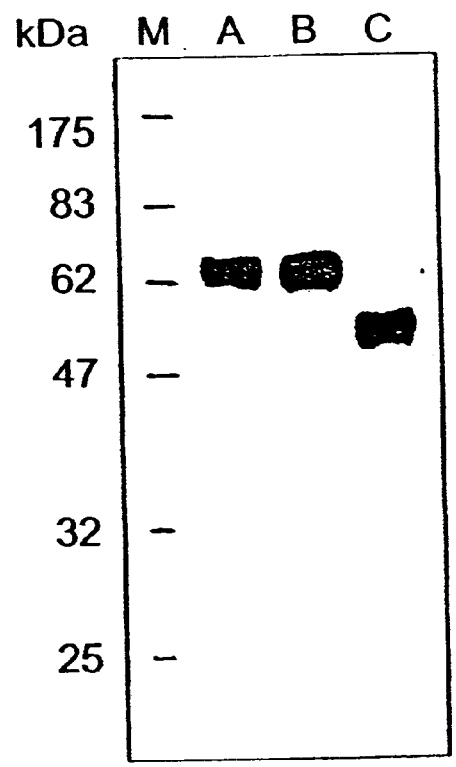
Figure 25B:
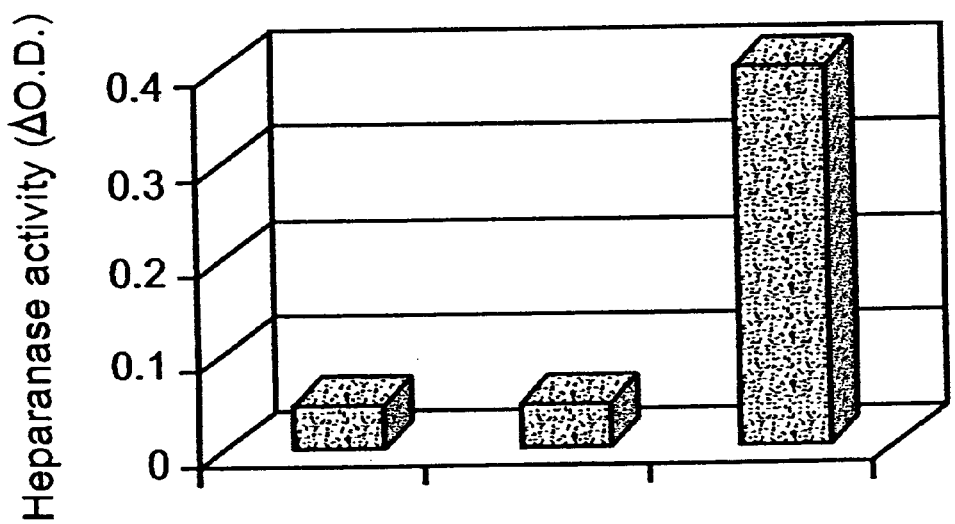

FIGS. 25a–b demonstrates proteolytic processing of heparanase from insect cells conditioned medium by protease impurities. FIG. 25a shows a Western blot analysis of heparanase, following processing of the enzyme expressed in insect cells. Heparanase expressed in insect cells, partially purified on a Source-S column, was incubated for one week at 4° C. in either, 20 mM phosphate citrate buffer pH 7, containing 5% PEG 300 (lane A), 20 mM phosphate citrate buffer pH 4, containing 5% PEG 300 and 1×protease inhibitors cocktail (Boehringer Mannheim, Cat. No. 1836170, lane B), or 20 mM phosphate citrate buffer pH 4, containing 5% PEG 300 (lane C). M—Molecular weight markers (NEB Cat. No. 7708S). FIG. 25b shows the results of DMB heparanase activity assays for the proteins.

Figure 25C:
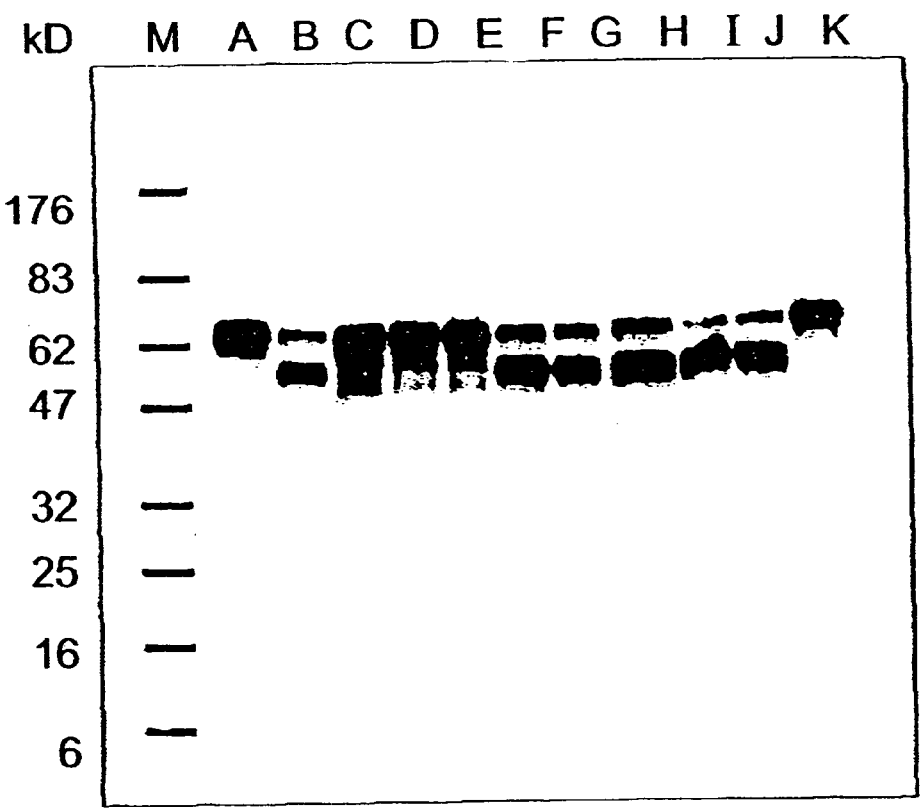
Figure 25D:
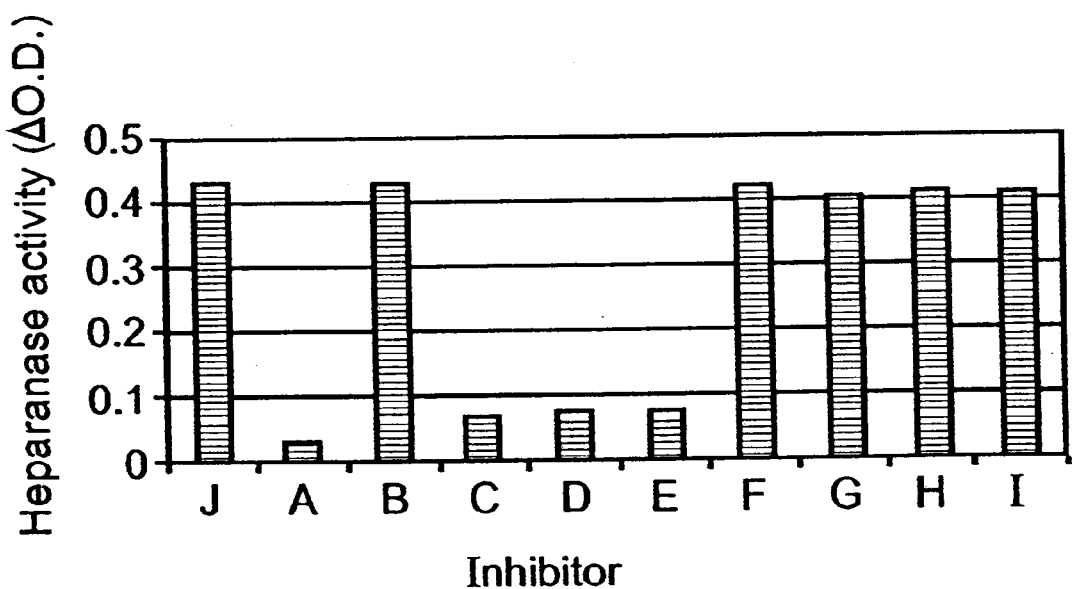

FIGS. 25c–d demonstrate the effect of a panel of protease inhibitors on proteolytic processing and activation of heparanase expressed in insect cells. Heparanase expressed in insect cells, partially purified on a Source-S column, was incubated for one week at 4° C. in 20 mM phosphate citrate buffer, pH 4, containing 5% PEG 300 and one of the different protease inhibitors: A—antipain; B—bestatin; C—chymostatin; D—E-64; E—leupeptin; F—pepstatin; G—phosphoramidon; H—EDTA; I—aprotinin. The treated samples were either subjected to western blot analysis (FIG. 25c) or to heparanase DMB activity assay (FIG. 25d). J—positive control, incubated in the absence of a protease inhibitor at pH 4; K—negative control, heparanase incubated with the same buffer at pH 7. M—Molecular weight marker (NEB Cat. No. 7708S).

Figure 26A:
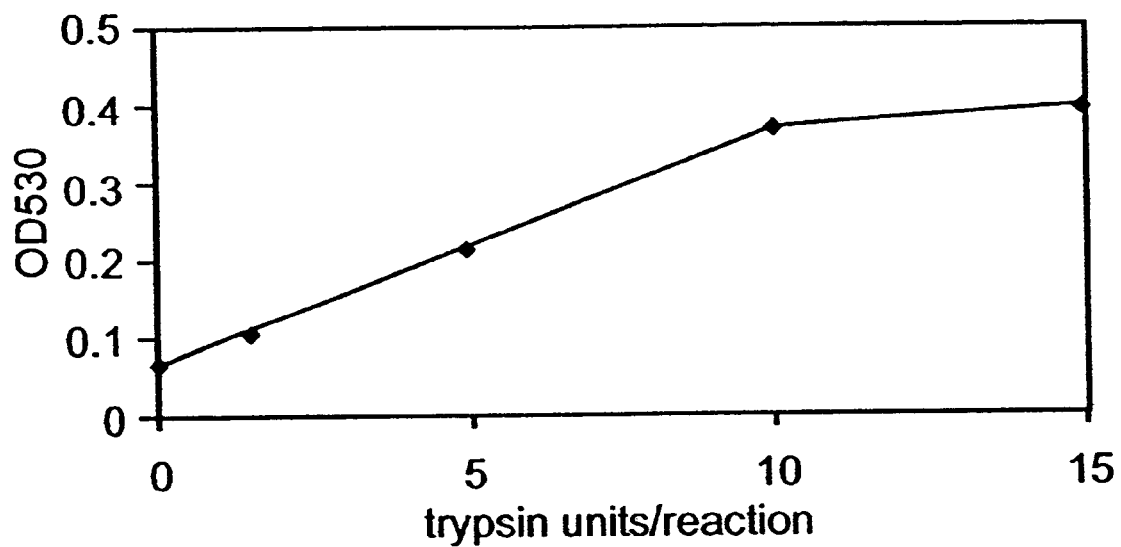

FIG. 26a demonstrates proteolytic processing of heparanase secreted from insect cells by trypsin. 10 μg of heparanase, expressed in insect cells, and partially purified on a Source-S column, was incubated with increasing concentrations of trypsin (0, 1.5, 5, 10, 15 units/test, Cat. No. T-8642, Sigma USA) for 10 minutes at 25° C. Following incubation, reaction tubes were placed on ice and 1.7 μg/ml aprotinin (trypsin inhibitor) was added. Activity was determined using the DMB assay.

Figure 26B:
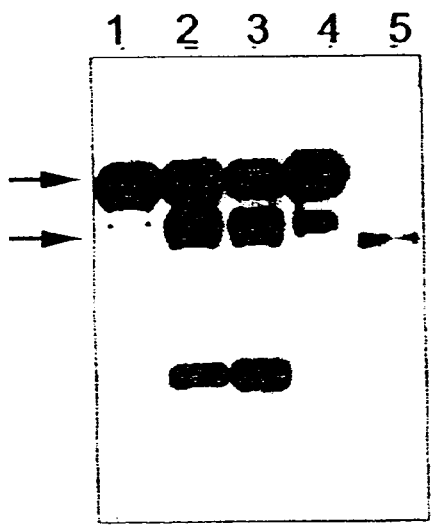

FIG. 26b demonstrates a Western blot analysis of heparanase following trypsin treatment. 10 μg of heparanase, expressed in insect cells, and partially purified on a Source-S column, was incubated without (lane 1) or with 150 or 500 units of trypsin (lanes 2 and 3, respectively). A processed heparanase sample treated as described in FIGS. 25a–b, lanes J (lane 4), and heparanase from a CHO 2TT1 cell extract (lane 5) served as controls.

Figure 27:
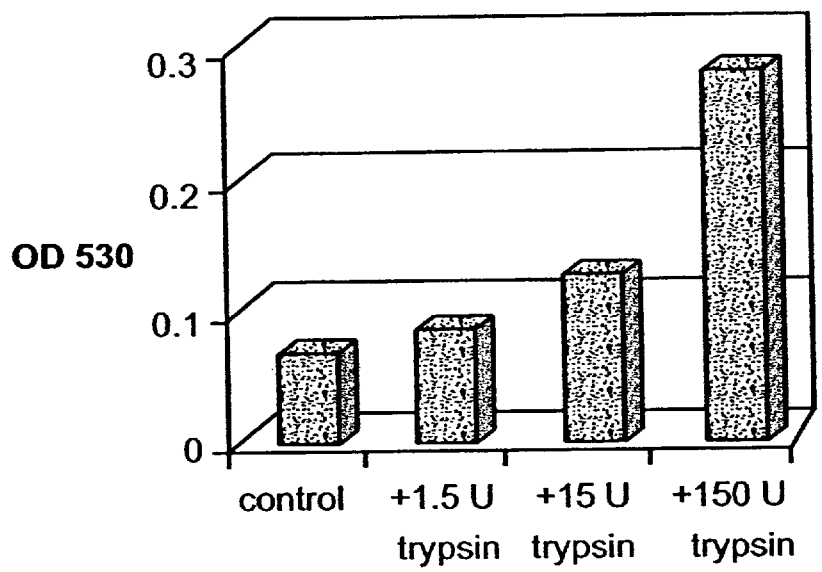

FIG. 27 proteolytic processing of heparanase secreted from CHO cells by trypsin. Conditioned medium of CHO cells transfected with pS1hpa (clone SlPPT-8) that secrete heparanase in a constitutive manner was subjected to proteolysis by trypsin. Unpurified CHO conditioned medium containing heparanase (0.5 μg heparanase per reaction) in 20 mM phosphate buffer, pH 6.8, was incubated with 0, 1.5, 15 or 150 units of trypsin for 10 minutes, at 37° C. Reactions were stopped by transferring the reaction tubes into ice and adding 2 μg/ml aprotinin. Tryptic digest products were assayed for heparanase activity using the DMB assay.

Figure 28A:
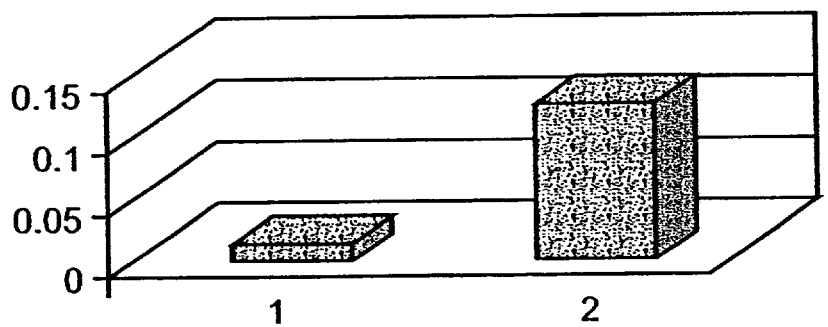
Figure 28B:
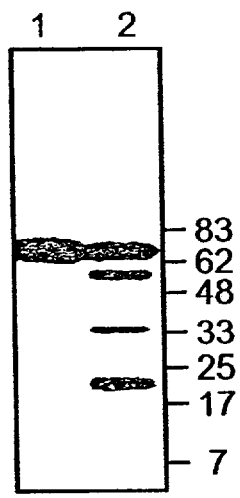

FIGS. 28a–b demonstrates proteolytic processing of p70-bac heparanase by cathepsin L. Partially purified heparanase from insect cells (10 μg) was subjected to proteolysis by 1.6 mU cathepsin L (Cat. No. 219412, Calbiochem) for 3 hours, at 30° C., in 20 mM citrate-phosphate buffer, pH 5.4. Heparanase catalytic activity and immunoreactivity before (1) and after (2) processing with cathepsin L as were determined using the DMB heparanase activity assay and Western blot analysis with monoclonal antibody No. HP-117 (disclosed in U.S. patent application Ser. No. 09/071,739) followed by ECL detection (Amersham, UK), FIGS. 28a–b, respectively.

Figure 29A:
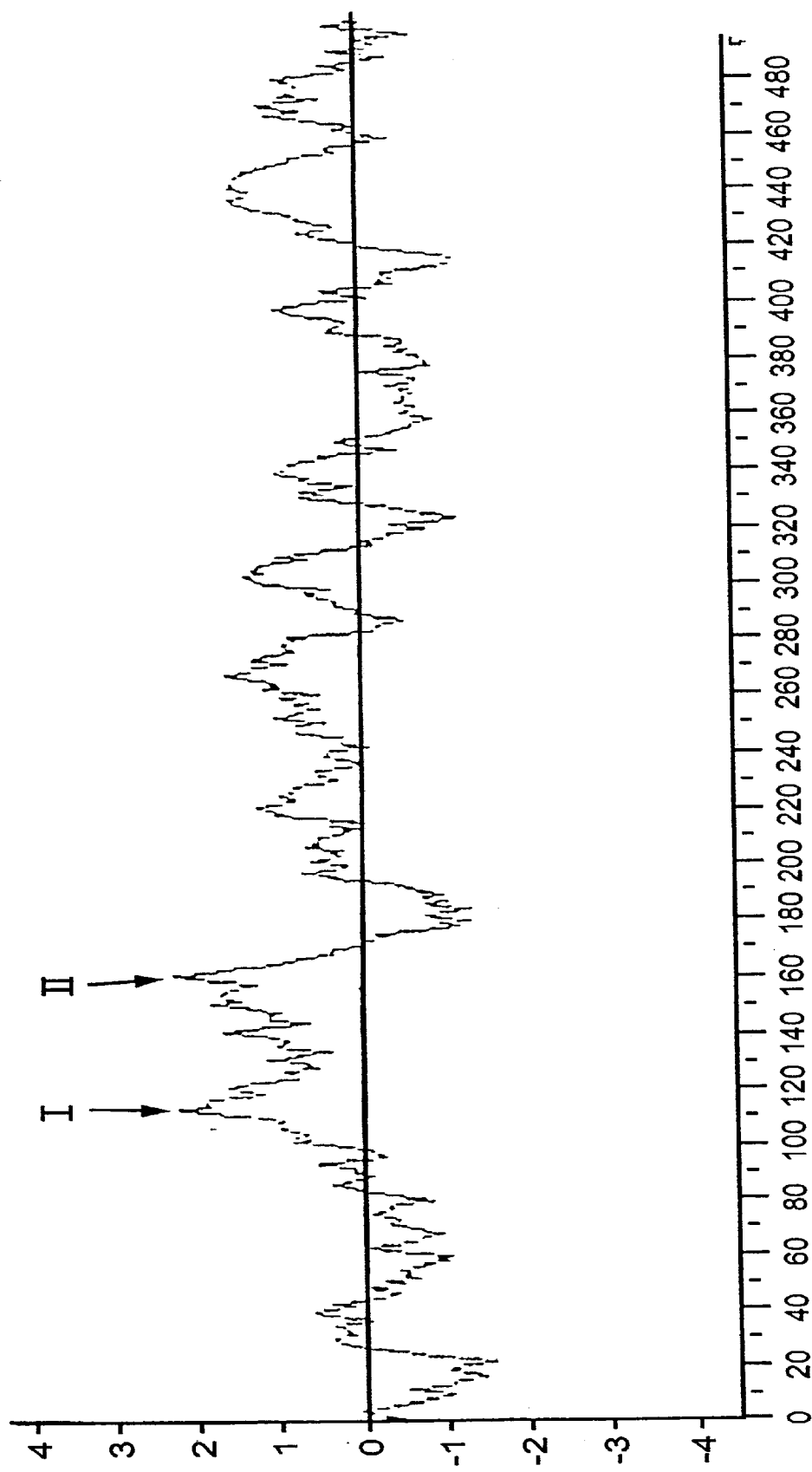

FIG. 29a demonstrates a hydropathy plot of SEQ ID NO:2 predicted for heparanase as calculated by the Kyte-Doolittle method for calculating hydrophilicity, using the Wisconsin University GCG DNA analysis software. I and II point at peaks of most hydrophilic regions of the enzyme.

Figure 29B:
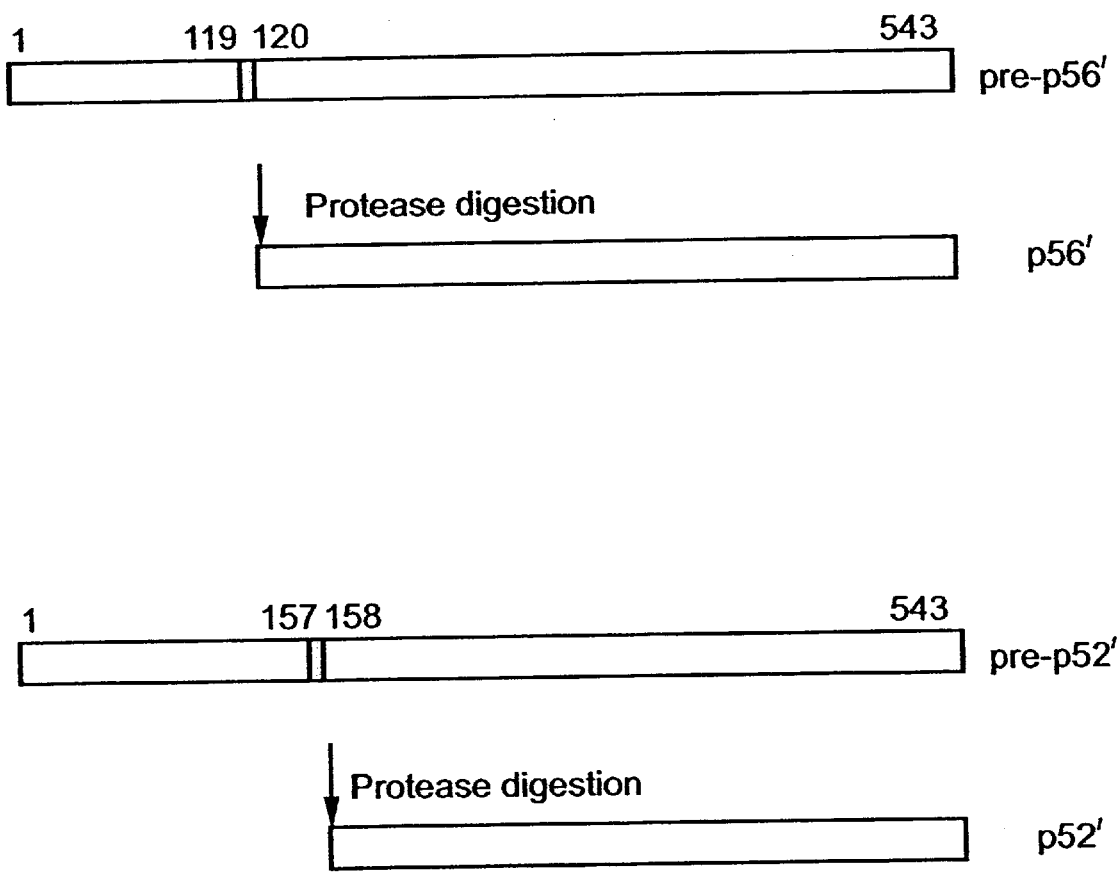

FIG. 29b is a schematic depiction of modified heparanase species (pre-p56' and pre-p52') that contain a unique protease recognition and cleavage sequence of factor Xa—Ile-Glu-Gly-Arg↓ (SEQ ID NO:13)— or of enterokinase—Asp-Asp-Asp-Asp-Lys↓ (SEQ ID NO:14) (shaded regions, located between amino acids 119 and 120 or 157 and 158 of the heparanase enzyme depicted in SEQ ID NO:2, which acids are located within peaks I and II, respectively, of FIG. 29a) which enable proteolytic processing by the respective proteases to obtain homogeneously processed and highly active heparanase species (p56' and p52', respectively).

Figure 29C:
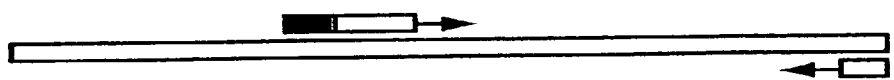
Figure 29C:
Figure 29C:
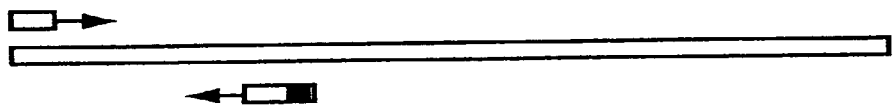
Figure 29C:
Figure 29C:
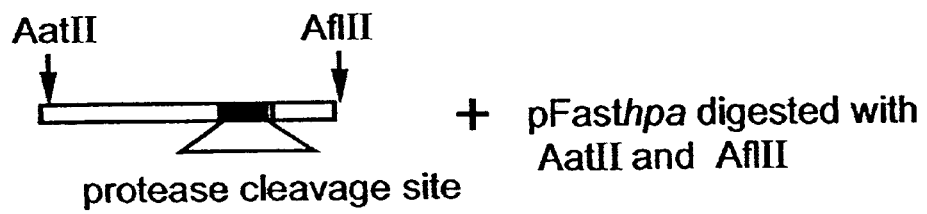

FIG. 29c is a schematic depiction of the steps in constructing nucleic acid constructs harboring a unique protease recognition and cleavage sequence of factor Xa—Ile-Glu-Gly-Arg↓ (SEQ ID NO:13)— or of enterokinase—Asp-Asp-Asp-Asp-Lys↓ (SEQ ID NO:14).

DESCRIPTION OF THE PREFERRED EMBODIMENTS

The present invention is of genetically modified cells overexpressing recombinant heparanase and of methods for overexpressing recombinant heparanase in cellular systems, which can be used to obtain purified recombinant heparanase in large quantities. Specifically, the present invention can be used to provide a scheme for biotechnological large scale recombinant heparanase production. The invention further relates to the activation of heparanase precursors by proteolysis and further to methods of in vivo inhibition of heparanase activity.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In one aspect, the present invention provides a genetically modified cell transduced with a polynucleotide sequence encoding a polypeptide having heparanase catalytic activity, designed to direct expression of recombinant heparanase by the cell.

In another aspect, the present invention provides a method of obtaining recombinant heparanase by genetically modifying a cell with an expression vector including a polynucleotide sequence encoding a polypeptide having heparanase catalytic activity, designed to direct expression of recombinant heparanase by the cell.

As used herein in the specification and in the claims section below, the phrase "genetically modified cell" refers to a cell that includes a recombinant gene. As further detailed below the cell may be a eukaryotic or prokaryotic cell.

As used herein in the specification and in the claims section below, the term "transduced" refers to the result of a process of inserting nucleic acids into cells. The insertion may, for example, be effected by transformation, viral infection, injection, transfection, gene bombardment, electroporation or any other means effective in introducing nucleic acids into cells. Following transduction the nucleic acid is either integrated in all or part, to the cell's genome (DNA), or remains external to the cell's genome, thereby providing stably transduced or transiently transduced cells.

As used herein in the specification and in the claims section below, the phrase "polynucleotide sequence" also means a nucleic acid sequence, typically a DNA sequence.

As used herein in the specification and in the claims section below, the term "polypeptide" also means a protein.

As used herein in the specification and in the claims section below, the phrase "heparanase catalytic activity" refers to an animal endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination.

As used herein in the specification and in the claims section below, the term "expression" refers to the processes executed by cells while producing and/or secreting proteins, including where applicable, but not limited to, for example, transcription, translation, folding and post translational modification and processing.

As used herein in the specification and in the claims section below, the terms "vector" and "construct" are interchangeably used herein and refer to any vehicle suitable for genetically modifying cells, including, but not limited to, viruses (e.g., bacoluvirus), phages, plasmids, phagemids, bacmids, cosmids, artificial chromosomes and the like.

As used herein in the specification and in the claims section below, the phrase "a polynucleotide sequence encoding a polypeptide having heparanase catalytic activity" refers to the potential of the polypeptide to have heparanase catalytic activity when correctly folded. Thus, this phrase refers to any catalytically active or inactive conformant of a polypeptide which may acquire at least one active conformation having heparanase catalytic activity.

According to a preferred embodiment of the present invention, the polynucleotide sequence is as set forth in SEQ ID NO:1 or a functional part thereof. The functional part encodes a polypeptide having heparanase catalytic activity. However, the scope of the present invention is not limited to SEQ ID NO:1 or a functional part thereof, as natural and man made innocuous variations thereof (e.g., mutations, such as point mutations) may also encode a protein having heparanase catalytic activity. Furthermore, it is shown hereinunder that a 52 kDa (formerly referred to as 45–50 kDa) protein, naturally processed from a 70 kDa (formerly referred to as 60 or 60–70 kDa) protein encoded by SEQ ID NO:1, has heparanase catalytic activity. The polynucleotide sequence may be a cDNA, a genomic DNA and a composite DNA (including at least one intron derived from heparanase or any other gene) as further detailed in U.S. patent application Ser. No. 09/435,739, entitled POLYNUCLEOTIDE ENCODING A POLYPEPTIDE HAVING HEPARANASE ACTIVITY AND EXPRESSION OF SAME IN GENETICALLY MODIFIED CELLS, which is incorporated herein by reference. Similarly it can be derived from any animal including mammalians and avians because, as shown in U.S. patent application Ser. No. 09/435,739, that heparanase sequences derived from species other than human beings are readily hybridizeable with the human sequence, allowing for isolation of such sequences by methods known in the art.

The functional part may be either man induced by genetic engineering or post translation artificial processing (e.g., by a protease) or naturally processed, depending on the cellular system employed.

According to another preferred embodiment of the present invention, the polypeptide includes an amino acid sequence as set forth in SEQ ID NO:2 or a functional part thereof having heparanase catalytic activity. However, the scope of the present invention is not limited to SEQ ID NO:2 or a functional part thereof, as natural and man made innocuous variations thereof (e.g., mutations, such single amino acid substitution) may also have heparanase catalytic activity. Polypeptides corresponding to species other than human and having heparanase catalytic activity are also within the scope of the present invention.

As used herein in the specification and in the claims section below, the term "functional part thereof" refers to a part of a nucleic acid sequence which encodes a polypeptide having heparanase catalytic activity or a part of a polypeptide sequence having heparanase catalytic activity.

In this context, it is important to remember that in many cases truncated or naturally processed polypeptides exhibit a catalytic activity similar to that of the natural polypeptide of the preprocessed polypeptide, respectively. Apparently, in many cases, not all of the amino acids of a protein are essential for its catalytic function, some may be responsible for other features, such as secretion, stability, interaction with other macromolecules, etc., whereas other may be replaced without affecting activity to a great extent. In many cases the processed protein exerts higher catalytic activity as compared with its unprocessed counterpart.

According to yet another preferred embodiment of the present invention, the polynucleotide sequence is selected from the group consisting of double stranded DNA, single stranded DNA and RNA.

According to still another preferred embodiment of the present invention, the cell is a bacterial cell, preferably *E. coli*.

According to a preferred embodiment of the present invention, the cell is an animal cell.

The animal cell may be a mammalian cell, such as, but not limited to, Chinese hamster ovary cell line (CHO), baby hamster kidney cells (BHK21), Namalwa cells, Dauidi cells, Raji cells, Human 293 cells, Hela cells, Ehrlich's ascites cells, Sk-Hep1 cells, $MDCK_1$ cells, $MDBK_1$ cells, Vero cells, Cos cells, CV-1 cells, NIH3T3 cells, L929 cells or BLG cells (mouse melanoma).

Alternatively, the animal cell may be a mammalian cell, such as, but not limited to, High five or Sf21.

According to another preferred embodiment of the present invention, the cell is a yeast cell, preferably a methylotrophic yeast, such as, but not limited to, *Pichia pastoris* and *Hansenula polymorpha*. Another preferred yeast is *Saccharomyces cerevisiae*.

The specified bacterial, yeast and animal cells are of specific advantage and interest since they are widely used in large scale biotechnological production of proteins and therefore knowledge has accumulated with respect to their large scale propagation, maintenance and with respect to recombinant protein purification therefrom.

According to another preferred embodiment of the present invention, the recombinant heparanase is human recombinant heparanase.

According to another preferred embodiment of the present invention, the polynucleotide sequence encodes, in addition, a signal peptide for protein secretion. The signal peptide may be the natural signal peptide of heparanase or any other suitable signal peptide, one non-limiting example is given under the Examples section hereinunder. The signal peptide sequence is fused downstream of and in frame with the heparanase sequence.

According to yet another preferred embodiment of the present invention, the method is further effected by purifying the recombinant heparanase. As further detailed hereinunder efficient purification (e.g., 90% purified) of recombinant heparanase may be effected by a single step ion exchange (e.g., Source-S) column.

The purification may be from the cells themselves. To this end the cells are collected, e.g., by centrifugation, homogenated and the recombinant heparanase is purified from the homogenate. If the recombinant heparanase is secreted by the cells to the growth medium, then purification is preferably from the growth medium itself.

According to yet another preferred embodiment of the present invention, the method further includes a step of subjecting the cell to a substance which induces secretion into the growth medium of secretable proteins, thereby inducing secretion of the recombinant heparanase into the growth medium. Preferably, the substance is selected from the group consisting of thrombin, calcium ionophores, immune complexes, antigens and mitogens, all are known to induce secretion of native heparanase from expressing cells. As shown in the Examples section below, the calcium ionophore calcimycin (A23187) and phorbol 12-myristate 13-acetate, are effective in inducing secretion of recombinant heparanase from transduced cells into their media.

According to yet another preferred embodiment of the present invention, the cell is grown to a large biotechnological scale of at least half a liter, preferably at least 5, 7 or 35 liters of growth medium, in a bioreactor, such as but not limited to, Spinner-Basket bioreactor.

Further according to the present invention there is provided a method of purifying a recombinant heparanase from overexpressing cells or growth medium in which they grow by adsorbing the recombinant heparanase on a Source-S column under low salt conditions (e.g., about 50 mM NaCl), washing said column with low salt solution thereby eluting other proteins, and eluting the recombinant heparanase from the column by a salt gradient (e.g., 50 mM to 1 M NaCl) or a higher concentration of salt (e.g., about 0.4 M).

According to a further aspect of the present invention there is provided an antibody comprising an immunoglobulin elicited against recombinant native heparanase. The immunoglobulin therefore recognizes and binds native (i.e., non denatured) natural or recombinant heparanase.

As used herein in the specification and in the claims section below, the term "antibody" include serum immunoglobulins, polyclonal antibodies or fragments thereof or monoclonal antibodies or fragments thereof. The antibodies are preferably elicited against a surface determinant of the particulate. Monoclonal antibodies or purified fragments of the monoclonal antibodies having at least a portion of an antigen binding region, including such as Fv, F(abl)2, Fab fragments (63), single chain antibodies (U.S. Pat. No. 4,946,778), chimeric or humanized antibodies (64–65) and complementarily determining regions (CDR) may be prepared by conventional procedure. Purification of the serum immunoglobulins antibodies or fragments can be accomplished by a variety of methods known to those of skill including, but not limited to, precipitation by ammonium sulfate or sodium sulfate followed by dialysis against saline, ion exchange chromatography, affinity or immunoaffinity chromatography as well as gel filtration, zone electrophoresis, etc. (see 66).

According to a further aspect of the present invention there is provided an affinity substrate comprising a solid matrix and an immunoglobulin elicited against recombinant native heparanase being immobilized thereto. Methods of immobilizing immunoglobulins to solid matrices, such as cellulose, polymeric beads including magnetic beads, are well known in the art. One such method is described in the Examples section that follows. The solid support according to the present invention can be packed into an affinity column.

According to a further aspect of the present invention there is provided a method of affinity purifying heparanase. The method is effected by (a) loading a heparanase preparation on an affinity column including a solid matrix and an immunoglobulin elicited against recombinant native heparanase being immobilized thereto; (b) washing the affinity column, e.g., using low, say 0–500 mM, salt solution; and (c) eluting heparanase molecules being adsorbed on the affinity column via the immunoglobulin, e.g., using a high, say 0.5–1.5 M, salt solution.

According to a further aspect of the present invention there is provided a method of activating a heparanase enzyme comprising the step of digesting the heparanase enzyme by a protease. The heparanase enzyme according to this aspect of the present invention can be natural or recombinant, purified, partially purified or non-purified. The protease can be of any type, including, but not limited to, a cysteine protease, an aspartyl protease, a serine protease and a meatlloproteinase. Examples of specific proteases associated with the above listed protease families are provided in the Background section. The use of other proteases for which heparanase includes a recognition and cleavage sequence is envisaged. According to a preferred embodiment digesting the heparanase enzyme by the protease is effected at a pH in which the protease is active, preferably most active. It is known that some proteases are most active in acidic pH values whereas other proteases are most active in basic pH values. The pH value at which a specific protease is most active can be readily determined by one ordinarily skilled in the art.

According to a further aspect of the present invention there is provided a method of in vivo inhibition of proteolytic processing of heparanase. The method according to this aspect of the present invention is effected by in vivo administering a protease inhibitor. The protease inhibitor can be, for example, a cysteine protease inhibitor, an aspartyl protease inhibitor, a serine protease inhibitor or a meatlloproteinase inhibitor. Examples of suitable inhibitors are provided in the Examples section that follows. Some protease inhibitors are used pharmaceutically for treatment of various conditions. In vivo inhibition of proteolytic processing of heparanase by a protease inhibitor can be used for treatment of cancer, metastatic cancers in particular, in which heparanase activity is involved, because, as further exemplified in the Examples section that follows, the pre-heparanase (non-processed, p70 heparanase) is characterized by lower activity as compared to its processed counterpart (p52 heparanase).

According to a further aspect of the present invention there is provided a nucleic acid construct comprising a first nucleic acid segment encoding for an upstream (N terminal) portion of heparanase, a second, in frame, nucleic acid sequence encoding a recognition and cleavage sequence of a protease and a third, in frame, nucleic acid sequence encoding for a downstream portion (C terminal) of heparanase, wherein the second nucleic acid sequence is in between the first nucleic acid sequence and the third nucleic acid sequence. Examples of such constructs are provided in the Examples section that follows. Preferably, the protease is selected having no recognition and cleavage sequences in the upstream and the downstream portions of heparanase, such that when expressed the modified heparanase is digested only at the introduced recognition and cleavage sequence of the protease. Preferably, the third nucleic acid sequence encodes for a catalytically active heparanase when correctly folded. However, embodiments wherein the second nucleic acid sequence is so positioned such that when expressed the modified heparanase protein is digestible into portions lacking catalytic activity are also envisaged. Such embodiments can be used to provide a heparanase species having a shorter half life, in, for example, physiological conditions, as compared with the non-modified enzyme. One ordinarily skilled in the art would know how to select locations for introduction of the recognition and cleavage sequence such that the sequence will not hamper the catalytic activity of the enzyme prior to cleavage thereof by the protease.

The above construct, when introduced into a cell expression system can be used to provide a precursor heparanase protein comprising an upstream portion of heparanase, a mid portion of a recognition and cleavage sequence of a protease and a downstream portion of heparanase, wherein the protease is selected having no recognition and cleavage sequences in the upstream and the downstream portions of heparanase. The recognition and cleavage sequence of the protease is composed either entirely from amino acids which are not present in natural heparanase, or from amino acids which are not present in natural heparanase in part, and further from adjacent amino acids which are present in natural heparanase. Further according to the present invention there is provided a heparanase protein resulting by digesting the precursor heparanase protein described herein.

According to a further aspect of the present invention there is provided a method of obtaining a homogeneously processed, active heparanase. The method according to this aspect of the present invention is effected by (a) expressing the precursor heparanase protein in a cell which secretes the precursor heparanase protein into the growth medium to obtain a conditioned growth medium, the precursor heparanase protein including an upstream portion of heparanase, a mid portion of a recognition and cleavage sequence of a protease and a downstream portion of heparanase, wherein the protease is selected having no recognition and cleavage sequences in the upstream and the downstream portions of heparanase; (b) treating the precursor heparanase protein with the protease; and (c) purifying a proteolytic heparanase product having heparanase catalytic activity.

It will be appreciated that the various heparanase species described herein, either activated and/or precursors can be used to produce pharmaceutical compositions, including, in addition to heparanase, a pharmaceutically acceptable carrier. Affmity purified and protease treated, modified, recombinant heparanase is of particular interest for pharmaceutical applications due to its homogeneity and purity.

The present invention has advantages because it provides means for expressing, purifying and activating recombinant/natural heparanase. Such heparanase can be used in pharmaceutical compositions (see, for example, U.S. patent application Ser. No. 09/046,465, in which heparanase is used in the treatment of CF), or as a source of enzyme for high throughput heparanase activity assay, which can be used for efficient screening of specific heparanase inhibitors (see, for example, U.S. patent application Ser. No. 09/113,168). By identifying the heparanase proteolytic activation process, novel indirect methods of in vivo heparanase inhibition by administration of protease inhibitors were conceived and tested in vitro. By identfying the heparanase proteolytic activation process, novel constructs encodin novel heparanase species has been constructed and can be used to direct the expression of a heparanase which is homogeneously processed and activated or alternatively neutralized by a dedicated protease.

EXAMPLES

Reference is now made to the following examples, which together with the above descriptions, illustrate the invention in a non-limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. Similarly, standard techniques are used for the proteolysis of heparanase by various proteases. These techniques and various other techniques used while reducing the present invention to practice are generally performed according to Sambrook et al., Molecular Cloning—A Laboratory Manual, Cold Spring Harbor Laboratory, Cold Spring Harbor, N.Y. (1989), which is incorporated herein be reference. Other general references are provided throughout this document. The procedures therein are believed to be well known in the art and are provided for the convenience of the reader. All the information contained therein is incorporated herein by reference.

Example 1

Expression of Recombinant Human Heparanase in Bacteria Experimental Methods Construction of expression vector: A 1.6 kb fragment of hpa cDNA (SEQ ID NO:1) was amplified from pfasthpa (hpa cDNA cloned in pFastBac, see U.S. patent application Ser. No. 08/922,170) by PCR using specific sense primer: Hpu-550Nde—5'-CGCATATGCAGGACGTCGTGG ACCTG-3' (SEQ ID NO:4) and a vector specific antisense primer: 3'pFast 5'-TATGATCCTCTAGTACTTCTCGAC-3' (SEQ ID NO:5). PCR conditions were: denaturation—94° C., 40 seconds, first cycle 3 minutes; annealing—58° C., 60 seconds; and elongation—72° C., 2.5 minutes, total of 5 cycles, and then denaturation—94° C., 40 seconds; annealing—68° C., 60 seconds; and elongation—72° C., 2.5 minutes, for additional 25 cycles.

The Hpu-550Nde primer introduced an NdeI site and an in frame ATG codon preceding nucleotide 168 of hpa. The PCR product was digested by NdeI and BamHI and its sequence was confirmed with vector specific and gene specific primers, using an automated DNA sequencer (Applied Biosystems, model 373A).

A 1.3 kb BamHI-KpnI fragment was cut out of pFasthpa. The two fragments were ligated with the pRSET bacterial expression vector (Invitrogen, California).

The resulting plasmid, designated pRSEThpaS1, encoded an open reading frame of 508 amino acids (36–543, SEQ ID NO:2) of the heparanase protein, lacking the N-terminal 35 amino acids which are predicted to be a signal peptide.

Transformation: Transformation of E. coli BL21(DE3) pLysS cells (Stratagene) was performed following Stratagene's protocol. Briefly, using β-mercaptoethanol in the transformation buffer cells were transformed by five seconds of heat shock at 42° C.

Expression of recombinant heparanase: E. coli BL21 (DE3)pLysS cells transformed with the recombinant plasmid were grown at 37° C. overnight in Luria broth (LB) medium containing 100 μg/ml ampicillin and 34 μg/ml chloramphenicol. Cells were diluted 1/10 in the same medium, and the cultures were grown to an OD600 of approximately 0.5. Isopropyl-thiogalactoside (IPTG) (Promega) was added to a final concentration of 1 mM and the culture was incubated at 37° C. for 3 hours. Cells from IPTG induced cultures were cooled on ice and sedimented by centrifugation at 4,000×g for 20 minutes at 4° C., and resuspended in 0.5 ml of cold phosphate-buffered saline (PBS). Cells were lysed by sonication, and cell debris were sedimented by centrifugation at 10,000×g for 20 minutes. The resulting pellet was analyzed for proteins by 10% SDS-PAGE, essentially as described in Harlow, E. and Lane, D. Eds. in Antibodies, a laboratory manual. CSH Laboratory press. New-York.

Experimental Results

Figure 1:
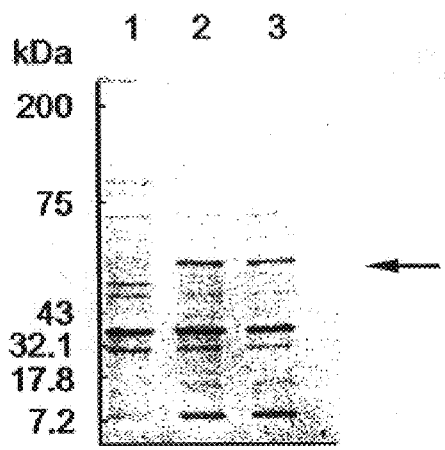
FIG. 1 demonstrates the expression of recombinant heparanase in E. coli BL21(DE3)pLysS cells. Insoluble fractions of induced E. coli cells containing expression constructs for heparanase were analyzed on 10% SDS-PAGE. Following electrophoresis the gel was stained with commassie blue. Lane 1—cells transformed with pRSET (negative control), lanes 2 and 3—cells transformed with pRSEThpaS1 (two different colonies). Molecular size in kDa is shown to the left (Prestained SDS-PAGE standards, Bio-Rad, California).

The expression of recombinant heparanase in E. coli BL21(DE3)pLysS cells containing the pRSEThpaS1 was analyzed by SDS-PAGE followed by commassie blue staining for proteins. Bacterial cells were fractionated and a protein of approximately 70 kDa, which is the expected size of the recombinant heparanase, was observed in the insoluble fraction (FIG. 1, lanes 2–3). That band did not appear when negative control cells transformed with pRSET were employed (FIG. 1, lane 1).

The identification of the recombinant heparanase expressed in E. coli was confirmed by a Western blot (data not shown) using a rabbit anti-heparanase polyclonal antibody (disclosed in U.S. patent application Ser. No. 09/071, 739), followed by ECL detection (Amersham, UK).

As compared to known quantities of co-size separated and stained BSA, the estimated yield of the heparanase recombinant protein under the conditions described was about 0.2 mg/ml of culture (not shown). The protein was found in the insoluble fraction (inclusion bodies) and had no enzymatic activity, as was determined by the soluble $^{35}$S-ECM degradation assay (not shown), however, the recombinant heparanase protein expressed in E. coli could provide a source for large quantities of heparanase.

It will be appreciated that solubillization and refolding of recombinant proteins expressed in E. coli are well known in the art (see, for example, for insulin, 70; others are reviewed in 71) and these procedures should be applied in order to obtain a functional protein having heparanase activity.

The expression of the recombinant heparanase in bacterial cells is thus demonstrated in this Example. It will be further appreciated that changes in protein length and/or amino acid composition might affect the efficiency of expression, correct folding and the potential yield of functional enzyme.

Example 2

Expression of Recombinant Human Heparanase in Yeast Experimental Methods

Construction of expression vectors for expression in yeast: Two expression vectors were constructed for the expression of hpa in *Pichia pastoris*. The first vector, designated pPIC3.5K-Sheparanase (FIG. 2) contains nucleotides 63–1694 of the hpa sequence (SEQ ID NO:1) cloned into the expression vector pPIC3.5K (Invitrogen, California) using a multistep procedure as follows.

A pair of primers: HPU-6641—5'-AGGAATTCACCATGCTGCT GCGCTCGAAGCCTGCG-3' (SEQ ID NO:6) and HPL-209 5'-GAGTAGCAATTGCTCCTGGTAG-3' (SEQ ID NO:7) were used in PCR amplification to introduce an EcoRI site just upstream to the predicted methionine. PCR conditions were: denaturation—94° C., 40 seconds; annealing—50° C., 80 seconds; and elongation—72° C., 180 seconds, total of 30 cycles.

Figure 2:
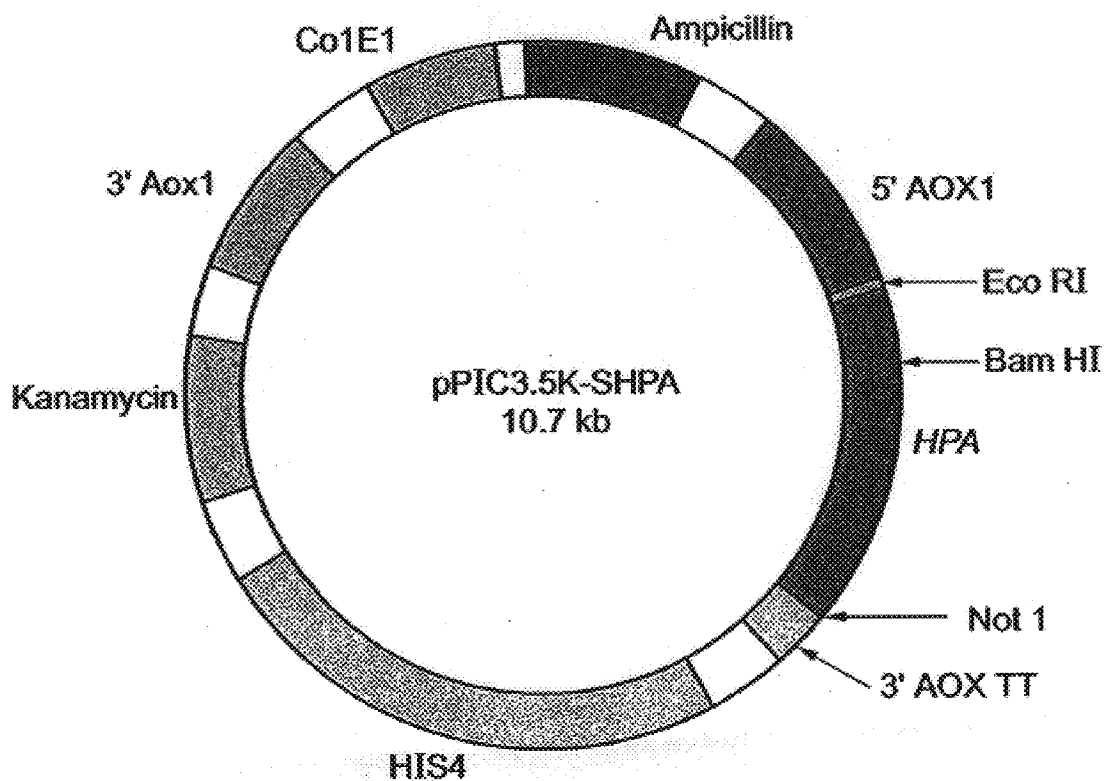
FIG. 2 is a schematic presentation of the expression vector pPIC3.5K-Sheparanase. Relative positions of some restriction enzymes and genes are indicated. For the construction and utilities of pPIC3.5K-Sheparanase, see Example 2 in the Examples section below.

The resulting PCR product was digested with EcoRI and BamHI and cloned into the EcoRI-BamHI sites of the vector phpa2 (described in U.S. patent application Ser. No. 08/922, 170). The hpa coding region was then removed as an EcoRI-NotI fragment and cloned into the EcoRI-NotI sites of the expression vector pPIC3.5K to generate the vector pPIC3.5K-Sheparanase (FIG. 2).

The second vector, designated pPIC9K-PP2 (FIG. 3), includes the hpa coding region except for the predicted signal sequence (N-terminal 36 amino acids, see SEQ ID NO:2). The hpa was cloned in-frame to the α-factor prepro secretion signal in the *Pichia pastoris* expression vector pPIC9K (Invitrogen, California). A pair of primers: HPU-559S, 5'-GTCTCGA GAAAAGACAGGACGTCGTGGACCTGGAC-3' (SEQ ID NO: 8) and HPL-209 (SEQ ID NO:7, described above) were used in PCR amplification under the conditions described above.

The resulting PCR product was digested with XhoI and BamHI and inserted into the XhoI-BamHI sites of the vector phpa2 (U.S. patent application Ser. No. 08/922,170).

Thereafter, the XhoI-NotI fragment containing the hpa sequence was removed and cloned into an intermediate vector harboring the SacI-NotI sites of pPIC9K.

Figure 3:
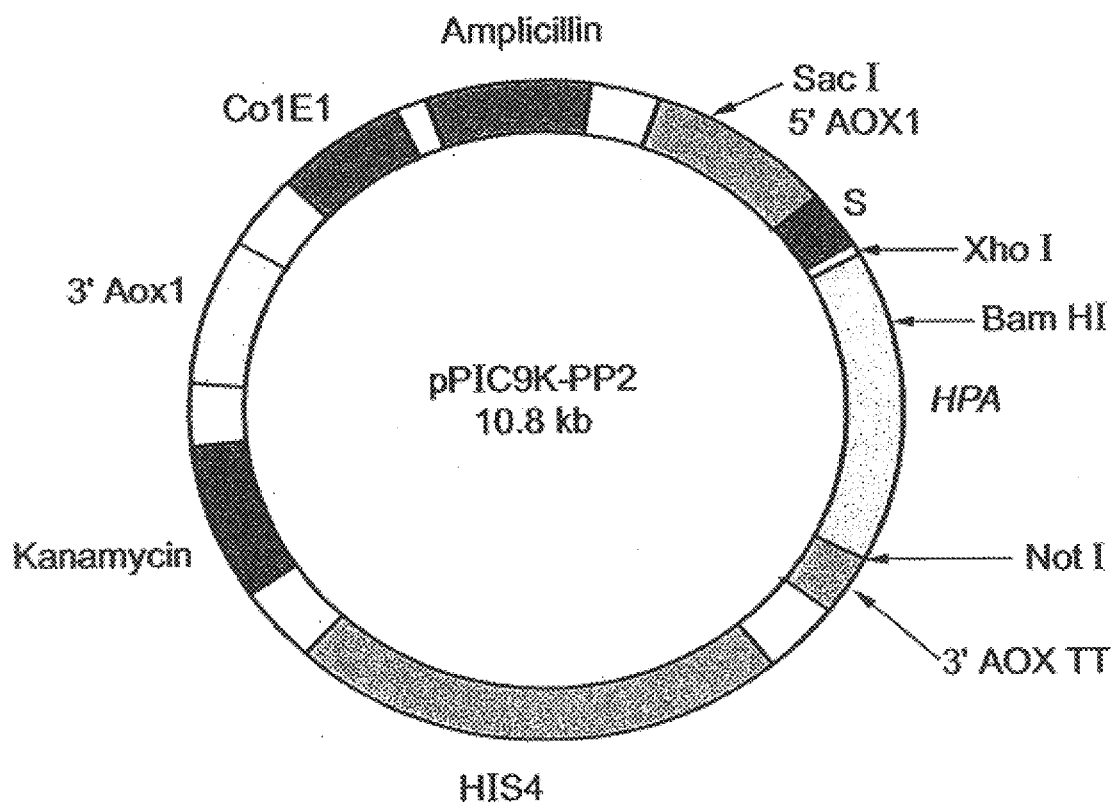
FIG. 3 is a schematic presentation of the expression vector pPIC9K-PP2. Positions of some restriction enzymes and genes are indicated. For the construction and utilities of pPIC3.5K-Sheparanase, see Example 2 in the Examples section below.

The hpa was removed from the later vector as a SalI-NotI fragment and cloned into the SalI-NotI sites of pPIC9K, thus creating the vector pPIC9K-PP2 (FIG. 3).

Transformation and screening: *Pichia pastoris* strain SMD1 168 (his3, pep4) (Invitrogen, California) was used as a host for transformation. Transformation and selection were carried out as described in the Pichia expression Kit protocol (Invitrogen, California). In all transformations the expression vectors were linearized with SalI prior to their introduction into the yeast cells.

Multiple copies integration clones were selected using G-418 (Boehringer Mannheim, Germany). Following transformation the top agar layer containing the yeast cells was removed and re-suspended in 10 ml of sterile water. Aliquots were removed and plated on YPD plates (1% yeast extract, 2% peptone, 2% glucose) containing increasing concentrations of G-418 (up to 4 mg/ml). Single isolates were picked and streaked on YPD plates. G-418 resistance was then further confirmed by streaking isolates on YPD-G-418 plates.

Expression experiments: Single colonies were inoculated into 6 ml BMGY—Buffered Glycerol-complex Medium (1% yeast extract, 2% peptone, 100 mM potassium phosphate pH 6.0, 1.34% yeast nitrogen base with ammonium sulfate without amino acids, $4\times10^5$ biotin and 1% glycerol) and incubated at 30° C. at 250 RPM for 24 hours. Cells were harvested using clinical centrifuge and re-suspended in 2.5 ml of BMMY—Buffered Methanol-complex Medium (The same as BMGY except that 0.5% methanol replaces the 1% glycerol). Cells were then incubated at 30° C. at 250 RPM agitation for 48 hour. Culture supernatants were separated on SDS-PAGE and electrophoretically transferred to a nitrocellulose membrane using the Hoeffer-Pharmacia apparatus, according to manufacturer protocol. A rabbit anti-heparanase polyclonal antibody (disclosed in U.S. patent application Ser. No. 09/071,739) was used as a primary antibody in detection of heparanase. Horseradish peroxidase-labeled anti-rabbit antibodies and ECL Western blotting detection reagents (Amersham, UK) were used in subsequent detection steps.

Experimental Results

Both pPIC3.5K-Sheparanase and pPIC9K-PP2 *Pichia pastoris* transformants secreted a protein with a similar molecular weight of about 70 kDa, as expected for heparanase. These results indicate that the heparanase contains a signal sequence which efficiently functions as a secretion signal in *Pichia pastoris*.

Figure 4:
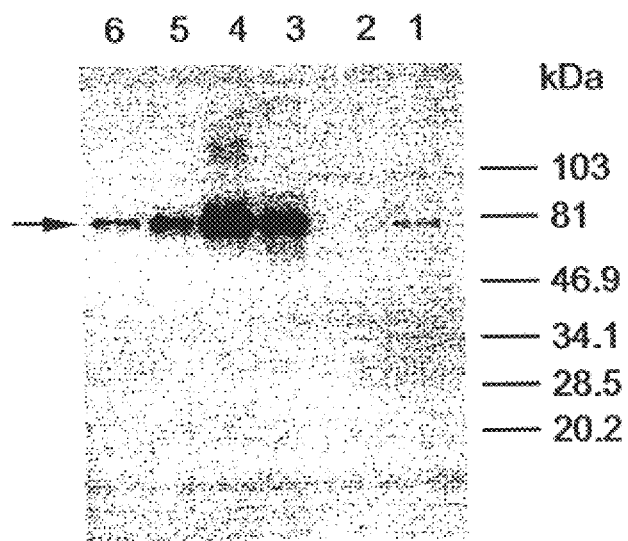
FIG. 4 demonstrates the secretion of human heparanase by transformed Pichia pastoris yeast cells. Western blot analysis using a rabbit anti-heparanase polyclonal antibody (disclosed in U.S. patent application Ser. No. 09/071,618, which is incorporated by reference as if fully set forth herein) was performed on culture supernatants of different transformants (with and without selection for G-418 resistance). Lane 1—pPIC3.5K-Sheparanase transformant, lane 2—pPIC3.5K transformant (negative control), lanes 3–6, transformants selected on 4 mg/ml of G-418. Molecular size is shown on the right as was determined using prestained SDS-PAGE standards, Bio-Rad, California.

G-418 resistance was used to select isolates characterized by multiple gene integration events. A faint heparanase band was observed in the supernatant of pPIC3.5K-Sheparanase transformant isolated without selection on G-418 (FIG. 4, lane 1), whereas no band was observed in the corresponding position in pPIC3.5K transformant, which served as negative control (FIG. 4, lane 2). A profound increase in the secretion of heparanase was observed in isolates resistance to 4 mg/ml of G-418 (FIG. 4, lanes 3–6).

Example 3

Expression and Secretion of Recombinant Human Heparanase in Mammalian Cells

Experimental Methods

Construction of hpa DNA expression vectors: A hpa gene fragment was cloned under the control of either SV40 early promoter (pShpa, FIG. 20a) or the CMV promoter (pChpa, FIG. 20e). One construct (pShpaCdhfr, FIG. 20b) also includes a selection marker, the mouse dhfr gene.

Specifically, a 1740 bp hpa gene fragment encoding for a 543 amino acid protein was introduced into pSI (Promega, USA) or pSI-Cdhfr vectors to yield vectors pShpa and pShpaCdhfr, respectively (FIGS. 5a and 5b and 20a and 20b). In both cases the gene was inserted under the SV40 early promoter regulation. pShpaCdhfr also carries an expression unit of mouse dhfr gene under the regulation of CMV promoter. Another plasmid, pCdhfr (FIG. 20f), included expression unit of mouse dhfr gene under the regulation of CMV promoter and served as control.

Figure 5A:
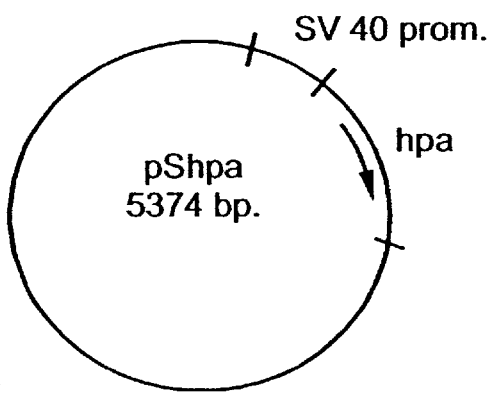
FIGS. 5a–e are schematic presentations of heparanase expression vectors adapted to direct heparanase expression in animal cells. hpa containing plasmids pShpa, pShpaCdhfr, pS1hpa, pS2hpa and pChpa are of 5374 bp, 7090 bp, 6868 bp, 6892 bp and 6540 bp, respectively. SV40 prom—SV40 early promoter, CMV prom—Citomegalovirus promoter, dhfr—mouse dihydrofolate reductase gene, PPT—preprotrypsin signal peptide, hpa—heparanase cDNA sequence, hpa' and hpa"—truncated hpa sequences.
Figure 5B:
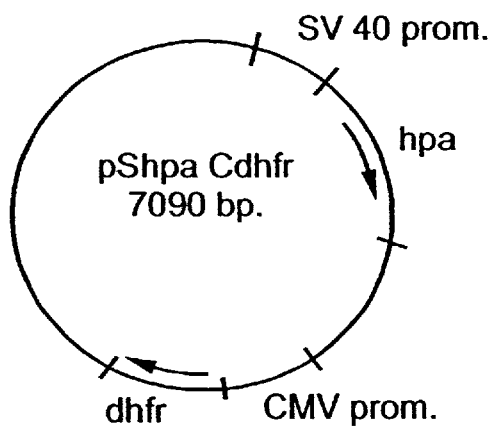
Figure 5C:
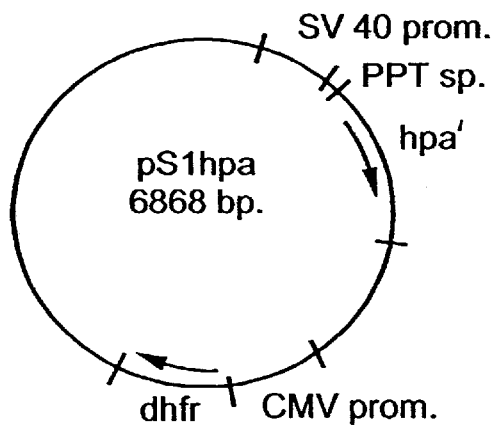

A vector designed pS1hpa (FIGS. 5c, 20c) was constructed by ligating a truncated hpa gene fragment (nucleotides 169–1721 of SEQ ID NO:1) to a heterologous signal peptide as follows. Preprotrypsin (PPT) signal peptide (72) was generated by chemically synthesizing two complementary oligonucleotides corresponding to the signal peptide encoding DNA sequence, the first having a sequence 5'-AATTCACCATGTCTGCACTTCTGATCCTAGCTC TTGTTGGAGCTGCAGTTGCTCAGGAC-3' (SEQ ID NO:9), whereas the second having a complementary sequence 5'-CCTGAGCAACTGCAGCTC CAACAAGAGCTAGGATCAGAAGTGCAGACATGGTG-3' (SEQ ID NO:10). Annealing of the complementary oligonucleotides produced the double strand sequence encoding to the PPT signal peptide flanked by a sticky end of an EcoRI restriction site on the 5' end thereof and a sticky end of an AatII restriction site on the 3' end thereof. Following restriction by EcoRI and AatII of the pfasthpa vector, a 145 bp fragment was removed, and replaced by the 52 bp PPT DNA sequence to yield plasmid pS1hpa. The insert thereof was cut out with EcoRI and DotI and ligated into the vector pSI.

A vector designed pS2hpa (FIGS. 5d and 20d) was constructed by ligating a truncated hpa gene fragment (nucleotides 144–1721) to the PPT signal peptide as follows. Preprotrypsin (PPT) signal peptide (72) was generated by chemically synthesizing two complementary oligonucleotides corresponding to the signal peptide encoding DNA sequence, the first having a sequence 5'-AATTCACCATGTCTGCACTTCTGA TCCT AGCTCTTGTTGGAGCTGAGTTGC-3' (SEQ ID NO:11), whereas the second having a complementary sequence 5'-CGGCAACTGCA GCTCCAACAA GAGCTA GGATCAGAAGTGCAGACATGGTG-3' (SEQ ID NO:12). Annealing of the complementary oligonucleotides produced the double strand sequence encoding to the PPT signal peptide flanked by a stick end of an EcoRI restriction site on the 5' end thereof and a sticky end of a NarI restriction site on the 3' end thereof.

Figure 5D:
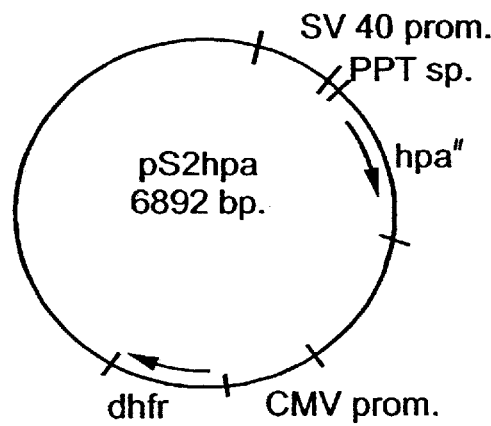

Following restriction by EcoRI and NarI of pS1hpa plasmid, a 112 bp fragment was removed therefrom and replaced by the PPT DNA sequence to give plasmid pS2hpa (FIGS. 5d, 20d).

Transfection of vectors into cells: DNA constructs were introduced into animal cells using the calcium-phosphate co-percipitaion technique essentially as described in (73).

Selection for dhfr expressing stable cellular clones: Following transfection, cells were incubated for 48 hours in a non-selective growth medium (F12 medium supplemented with 10% fetal calf serum). Then, the medium was changed to a selection medium (DMEM supplemented with 10% dialyzed calf serum) and cells were propagated to confluence at 37° C., under 8% $CO_2$ aeration. Methotrexate (MTX, 5000 nM) was added to the growth selection medium and resistant cellular clones were isolated. Alternatively, cells were transferred after transfection directly to a selection medium containing MTX (100–1000 nM).

SDS polyacrylamide gel electrophoresis and Western blot analysis: Denatured and reduced samples were loaded on ready made gradient (4–20%) gels (Novex, USA) and separated under standard gel running conditions (as described in Protein Electrophoresis Application Guide, Hoeffer, U.S.A.). Transfer of proteins onto a PVDF membrane was performed electrophoretically by a protein transfer apparatus (Hoeffer-Pharmacia). Detection of specific protein was accomplished by a rabbit anti-heparanase polyclonal antibody (disclosed in U.S. patent application Ser. No. 09/071, 739) (×2000 dilution), followed by ECL detection (Amersham, UK).

Determination of heparanase activity: ECM-derived soluble HSPG assay was performed by incubating cell extracts with solubillized $^{35}$S-labeled ECM (18 hours, 37° C.) in the presence of 20 mM phosphate buffer (pH 6.2), and size fractionation of the hydrolyzed fraction of the ECM by gel filtration on a Sepharose CL-6B column. Radiolabeling of degradation fragments eluted at 0.5<Kav<0.8 (peak II) was determined (61).

Alternatively, degradation of soluble high molecular weight heparan sulfate or heparin molecules to smaller fragments was detected by polyacrylamide gel electrophoresis analysis. Polyacrylamide gels (7.5%) were loaded with 2.5 mg heparin that was either untreated or incubated with heparanase containing cell extracts or media. Staining by methylen blue (74) enabled detection of the heparin molecules and its degradation products. The mobility of the molecules on the gel reflects their size. Therefore, activity of heparanase is reflected in a larger quantity of rapidly migrating heparin degradation products.

Induction of secretion: CHO stable clones and untransfected CHO cells were induced for secretion of proteins by either calcium ionophore calcimycin (A23187) (Sigma) or phorbol 12-myristate 13-acetate (PMA, Sigma), at different concentrations (0.01, 0.1 and 1.0 mg/ml), for various incubation times (2, 8, 24,48 hours). Induction was performed in the absence of serum. Conditioned medium was collected with 10% buffer citrate pH 5.6 and 200 KIU/ml aprotinin (Protosol, Rad Chemicals, Israel), centrifuged to remove floating cells, and kept at −200° C. The amount of secreted protein(s) was detected by Western blot analysis, and its activity was determined by $^{35}$S-ECM degradation assay and soluble heparan sulfate substrate hydrolysis assay. When necessary conditioned medium was concentrated by ultra-filtration through a 10 kDa filter (Millipore).

Large scale propagation of animal cells in a Spinner-Basket bioreactor: The structure and mode of operation of the bioreactor is described in detail in reference 75. A Spinner Basket bioreactor (500 ml, New Brunswick Scientific) embedded with 10 grams of Fibracel discs (Sterillin, U.K.) was inoculated with seeding inoculum of $1.5 \times 10^8$ cells of a stable clone of CHO cells designated $GGG_{11}$ that constitutively produces recombinant heparanase. Propagation of cells was performed in a medium containing 10% serum and cell proliferation was monitored by measurement of glucose consumption.

Then growth medium was replaced with medium without serum, suitable for the production of the recombinant protein. This medium served as a source for recombinant heparanase for later purification.

Experimental Results

Expression of hpa DNA in animal cells: Expression of recombinant hpa gene products was detected in a human kidney fibroblasts cell line (293), baby hamster kidney cells (BHK21) and Chinese hamster ovary (CHO dhfr-) cells, following transfection with the hpa gene (FIGS. 6a–b).

Figure 6A:
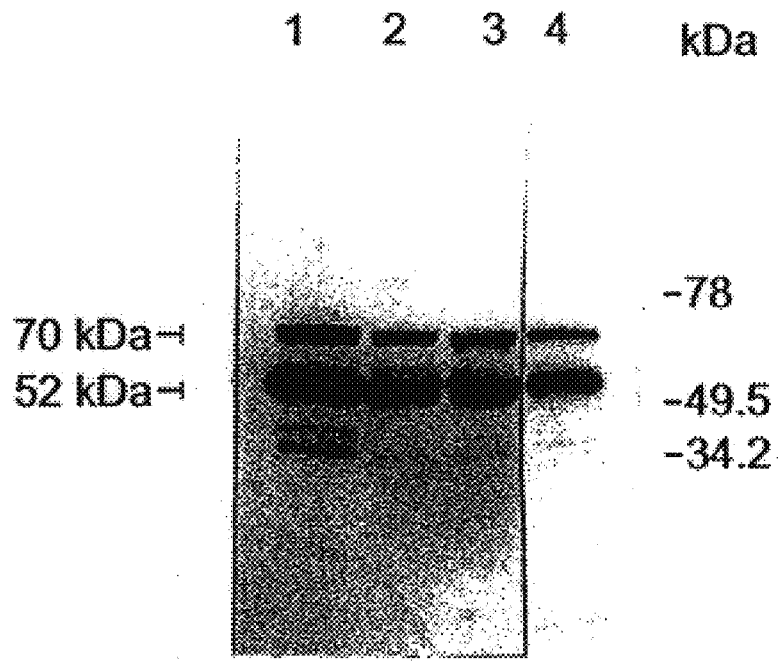
FIGS. 6a–b show Western blot analysis of hpa transfected cells. Cell extracts (40 μg of CHO cells or 8 μg of 293 cells) were separated on 4–20% gradient SDS-PAGE and transferred to PVDF membranes. Detection of hpa gene products was performed with a rabbit anti-heparanase polyclonal antibody (disclosed in U.S. patent application Ser. No. 09/071,739) followed by ECL detection (Amersham, UK).
Figure 6B:
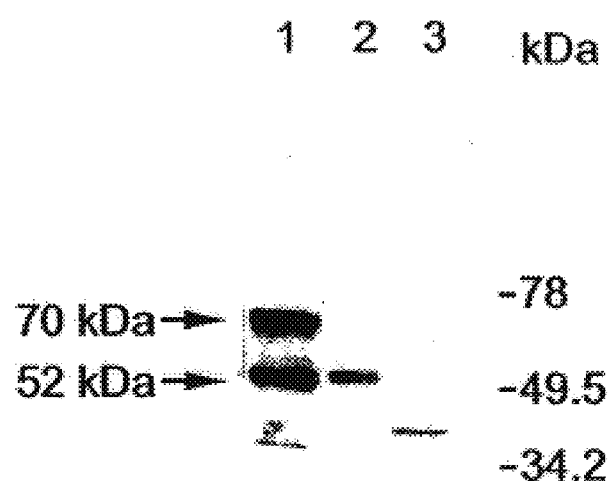

Analysis of recombinant heparanase by Western blotting revealed two distinct specific protein products: a large protein of about 70 kDa and a predominant protein of about 52 kDa (FIGS. 6a–b).

Transient expression of heparanase proteins was monitored 24–72 hours post transfection in various cell types.

Figure 5E:
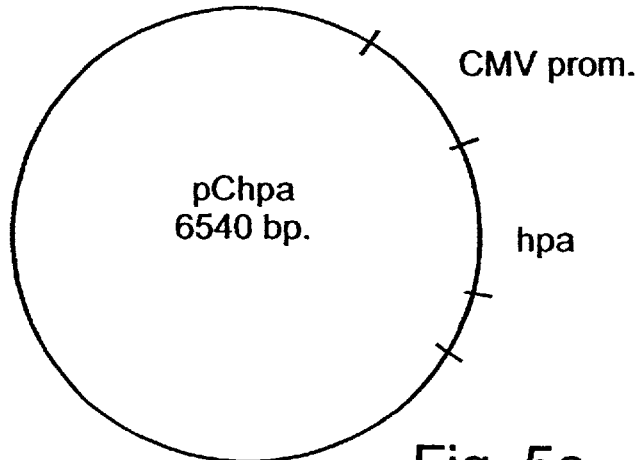

Human fibroblasts (293 cell line) transfected with pShpa (FIG. 5a) or pChpa constructs (FIG. 5e) exhibited heparanase activity (FIG. 6a, lane 4, Table 1 below).

Transfection of CHO cells with the expression vector pShpaCdhfr (FIG. 5b) and subsequent selection for MTX resistant clones resulted in the isolation of numerous clones. These cellular clones express hpa gene products in a constitutive and stable manner (FIG. 6a, lanes 1–3).

Several CHO cellular clones have been particularly productive in expressing hpa proteins, as determined by protein blot analysis and by activity assays (FIGS. 6a, FIG. 6b, lane 1, and Table 1). Although the hpa DNA encodes for a large 543 amino acids protein (expected molecular weight about 70 kDa) the results clearly demonstrate the existence of two proteins, one of about 70 kDa and another of about 52 kDa. These observations are similar to the results of the transient hpa gene expression in human 293 cells (FIG. 6a, lane 4). Transient expression of pShpaCdhfr in CHO cells revealed predominantly a 52 kDa heparanase protein (FIG. 6b, lane 2).

It has been previously shown that a 52 kDa protein with heparanase activity was isolated from placenta (61) and from platelets, (62). It is thus likely that the 70 kDa protein is naturally processed in the host cell to yield the 52 kDa protein.

Heparanase secretion into the growth medium: For large scale production and purification purposes, secretion of the recombinant protein into the growth medium is highly desirable. Therefore, expression vectors were constructed (pS1hpa and pS2hpa, FIGS. 5c–d) that would drive translation of heparanase attached to the PPT signal peptide.

Figure 7A:
FIGS. 7a–b demonstrate recombinant heparanase secretion induced by calcium ionophore and PMA. Cells of a stable CHO clone (2TT1) were induced with either calcium ionophore (FIG. 7a) or PMA (FIG. 7b). Condition media were collected and 20 ml loaded on SDS polyacrylamide gel followed by Western blot analysis with a rabbit anti-heparanase polyclonal antibody (disclosed in U.S. patent application Ser. No. 09/071,739) followed by ECL detection (Amersham, UK). Molecular size in kDa is shown on the right, as was determined using prestained SDS-PAGE standards, Bio-Rad, California.
Figure 7B:
Figure 7C:
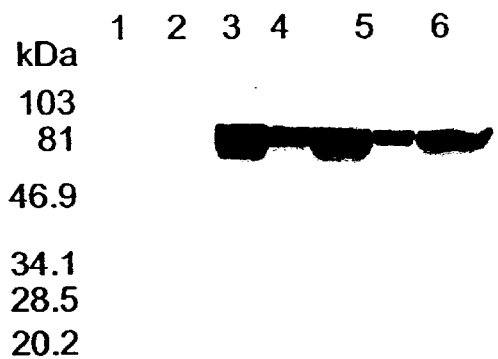
FIG. 7c demonstrates recombinant heparanase secretion by human 293 cells. Conditioned media of human 293 cells transfected with pS1hpa (lanes 3 and 4), pS2hpa (lanes 5 and 6) or control, untransfected cells (lanes 1 and 2), were loaded on a denaturative 4–20% polyacrylamide gel (lanes 1, 3 and 5), or 5 fold concentrated by 10 kDa ultrafiltration tube (Intersep U.K.) (lanes 4 and 6). Heparanase was detected by Western blot analysis with a rabbit anti-heparanase polyclonal antibody (disclosed in U.S. patent application Ser. No. 09/071,618) followed by ECL detection (Amersham, UK). Molecular size in kDa is shown on the left, as was determined using prestained SDS-PAGE standards, Bio-Rad, California.

Both pS1hpa and pS2hpa plasmids directed the expression of protein product with heparanase activity in human 293 or CHO cells (Table 1). The heparanase was not secreted to the medium in CHO cells. However, transient expression of heparanase encoded by pS1hpa and pS2hpa in human 293 cells resulted in the appearance of a single size (about 65 kDa) heparanase protein (FIG. 7c, lanes 3–6).

TABLE 1

Determination of Heparanase activity in transfected animal cells

| Cell type | transfected DNA | Heparanase Activity |
| --- | --- | --- |
| Human 293 cells | pChpa | + (a) |
| Human 293 cells | pShpa | + (b) |
| Human 293 cells | pS1hpa | + (b) |
| Human 293 cells | pS2hpa | + (b) |
| CHO | pShpaCdhfr | + (a) |

Cell extracts were assayed for heparanase activity using ECM-derived soluble HSPG assay (a) or direct hydrolysis of soluble substrate (b). Activity detected either in transiently expressing cells (293, CHO) or stable cellular clones (CHO).

Figure 8A:
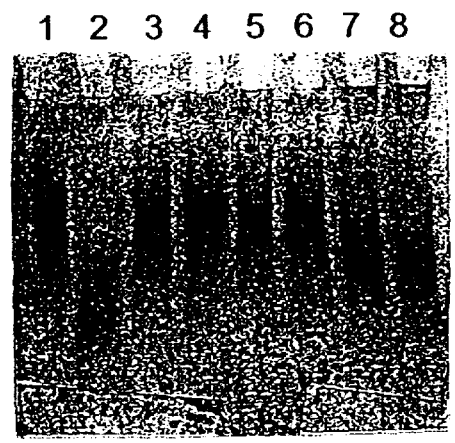
FIG. 8a demonstrates heparanase activity as expressed by the ability to degrade heparin. Following overnight incubation with 50 ml unconcentrated (lanes 3, 6), 20×concentrated (lanes 4 and 7) or 40×concentrated (lanes 5 and 8) conditioned media, from untreated (lanes 3–5) versus treated (lanes 6–8, 2 hours of incubation with 1 mg/ml calcium ionophore) stable clones, samples were electrophoretically separated on 7.5% polyacrylamide gel. Undegraded and degraded (by purified natural human heparanase) controls are shown in lanes 1 and 2 respectively.
Figure 8B:
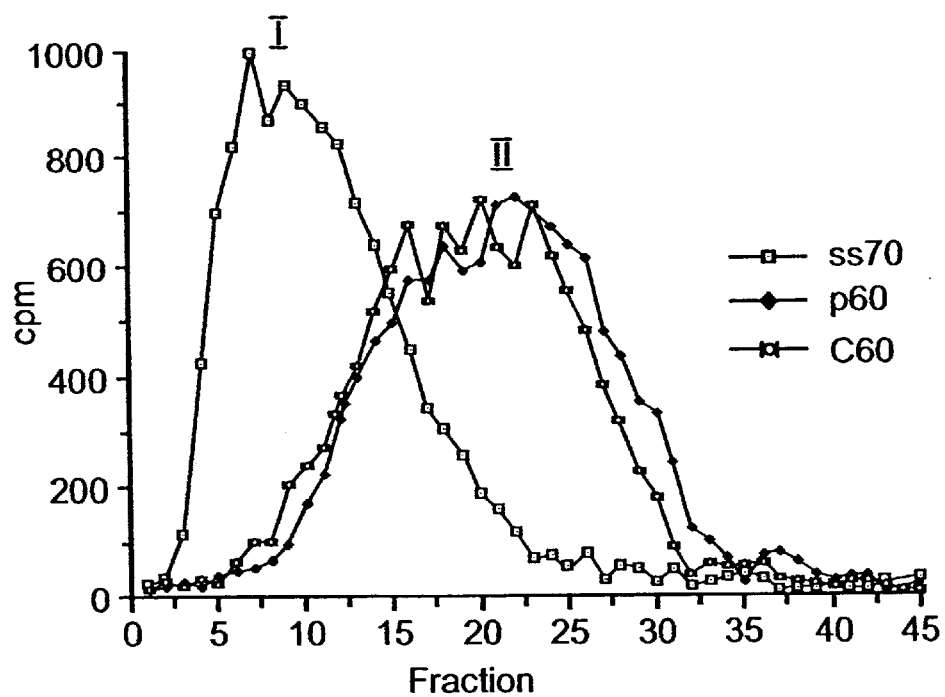
FIG. 8b–c demonstrate recombinant heparanase activity following secretion induced by calcium ionophore as determined by the soluble $^{35}$S-ECM degradation assay. 8b—the heparanase activity in one ml untreated conditioned media (c60), compared to one ml conditioned media treated with 100 ng/ml calcium ionophore for 24 hours (p70) from stable CHO clones was determined by the soluble $^{35}$S-ECM degradation assay. 8c—the heparanase activity in one ml untreated conditioned media (c45), compared to one ml conditioned media treated with 1 mg/ml calcium ionophore for two hours (p52) from stable CHO clones was determined by the soluble $^{35}$S-ECM degradation assay. Degraded substrates shift to the right.
Figure 8C:
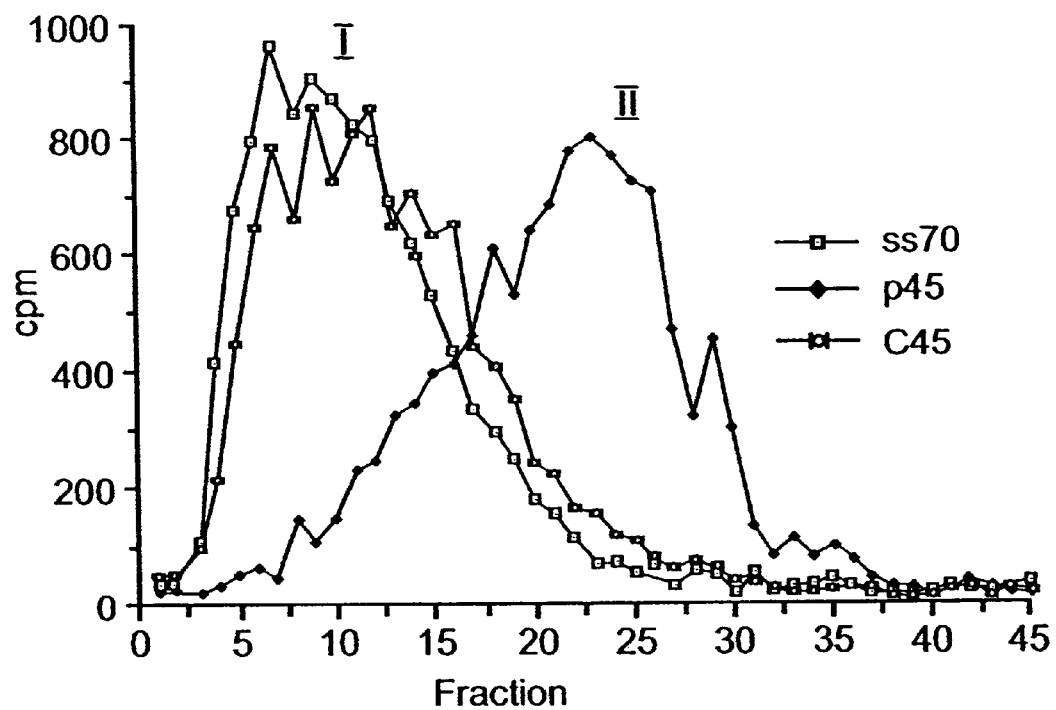
Figure 8D:
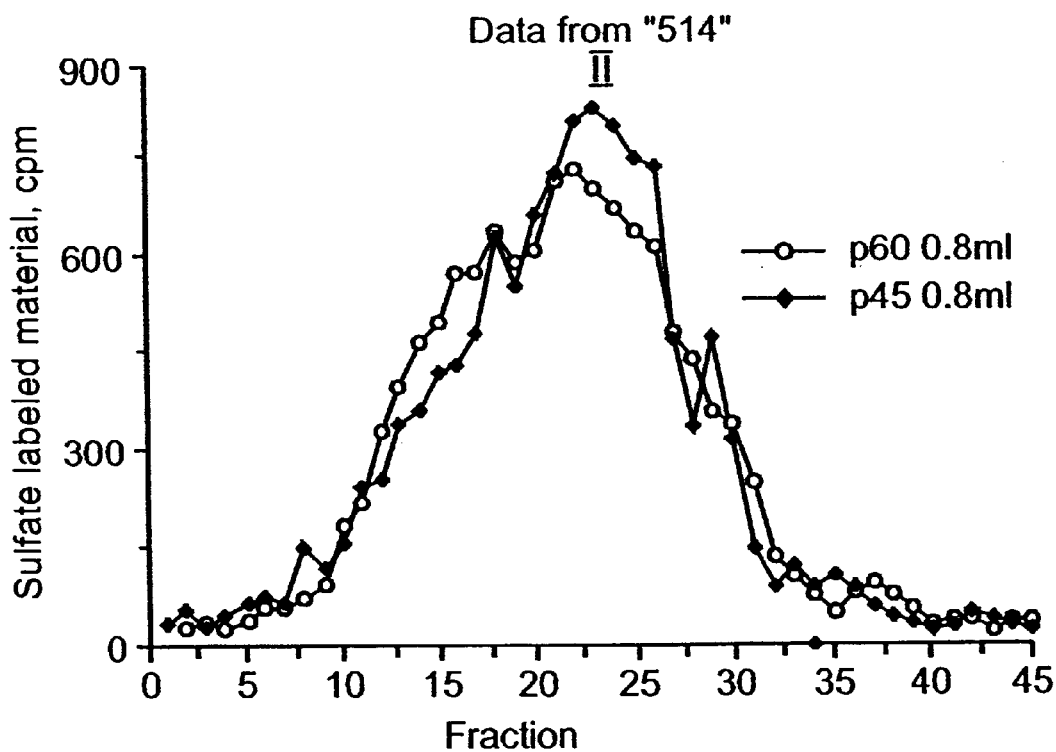
Figure 8E:
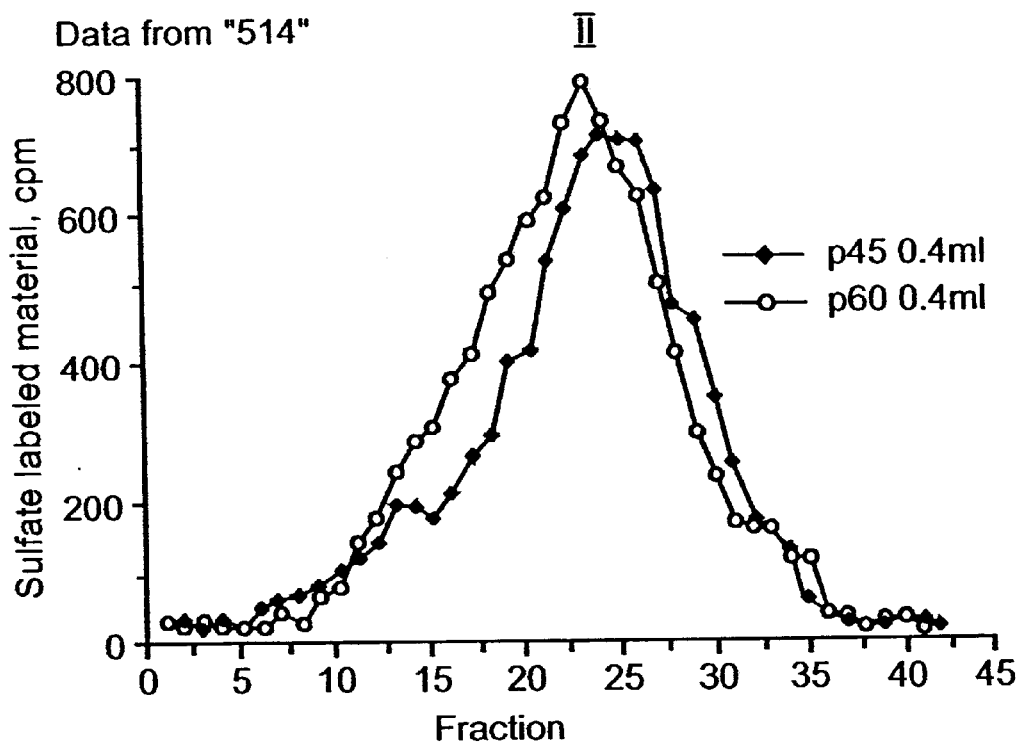
Figure 8F:
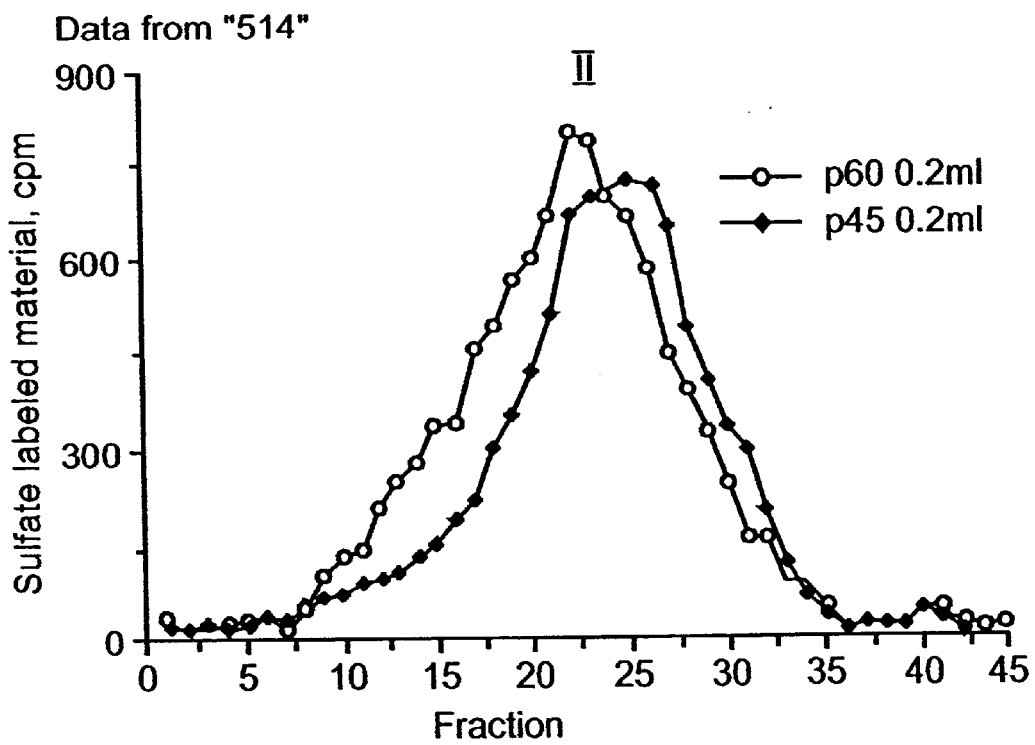
Figure 8G:
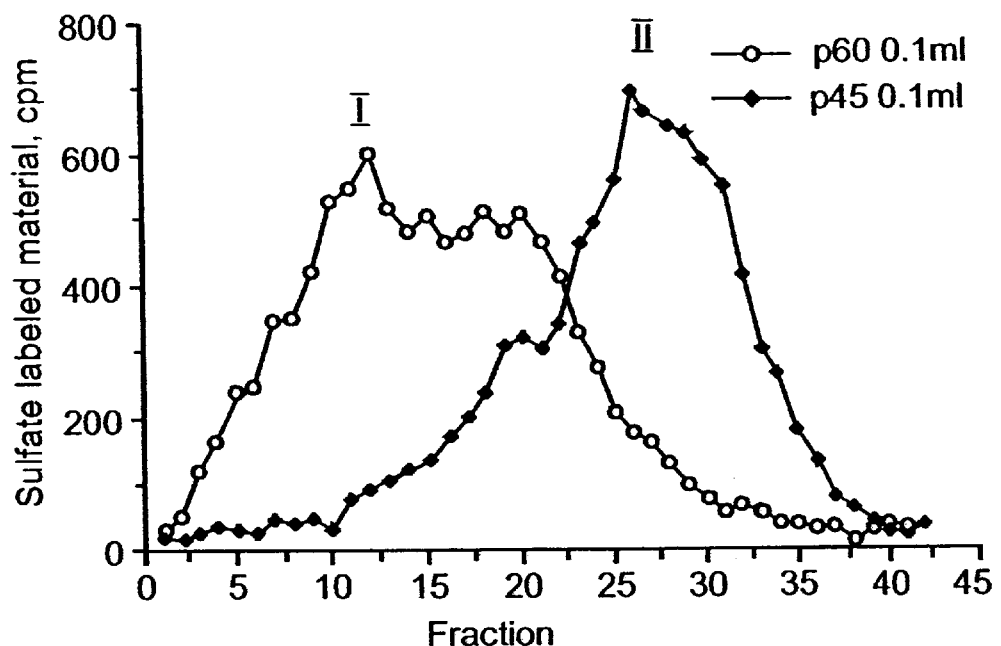

In order to induce secretion of the recombinant protein(s) into the medium, stable clones and untransfected CHO cells were induced with either calcium ionophore or PMA. The results show that induction with 1 mg/ml calcium ionophore for 2 hours stimulates the secretion of protein of about 52 kDa from stable clones but not from untransfected cells (data not shown) or untreated stable clones, while longer (24–48 hours) incubation time with 100 ng/ml of calcium ionophore induces predominantly the secretion of protein of about 70 kDa from stable clones (FIGS. 7a–b). The conditioned medium obtained from the treated stable clone, which exhibited the 52 kDa protein, had strong heparanase activity in ECM-derived soluble HSPG assay (FIGS. 8b–c), and in concentrated conditioned medium, in the gel shift assay (FIG. 8a). The heparanase activity in the conditioned medium from the treated stable clone, which exhibited the 70 kDa, is lower than that of the 52 kDa fraction (FIGS. 8d–g), since it was active when diluted eight fold while the 70 kDa protein failed to show activity in this dilution. It is thus possible that the 52 kDa protein is the active form of a less active pre heparanase of 70 kDa, which is naturally processed to yield the mature-active 52 kDa heparanase.

Figure 9:
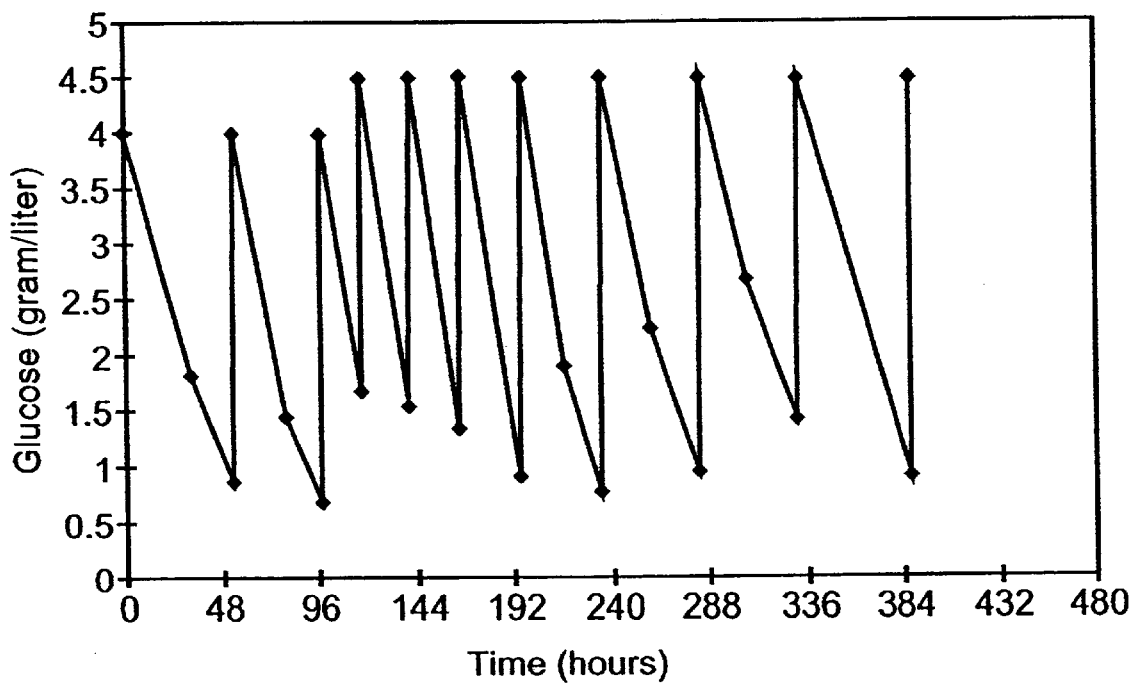
FIG. 9 demonstrates glucose consumption record of heparanase producing cells in a large scale, 0.5 liters, Spinner-Basket bioreactor.

Large scale production of heparanase: Large scale propagation of heparanase expressing cells was set up in a 500 ml volume Spinner-Basket bioreactor to demonstrate the ability to obtain a dense adherent cell culture for large scale production of heparanase. Heparanase constitutively producing cell line was propagated in the Spinner-Basket bioreactor and at the end of the proliferation phase the medium was replaced with production medium which has the same composition as the growth medium but without serum. Cell proliferation and viability were constantly monitored by daily measurements of glucose concentration in the medium. Level of glucose was also the parameter used to determine the frequency of medium refreshment in the bioreactor, as described in reference 76. Results of a typical "batch run" that includes proliferation and maintenance of heparanase producing cells in a 500 ml Spinner-Basket are shown in FIG. 9.

A "batch run" in a Spinner-Basket bioreactor can last about four weeks, when serum is omitted from the culture medium. The apparatus can be linearly enlarged to bioreactors of 5, 7 or 35 liters. Accordingly, larger amounts of Fibracel can be packed in those vessels and accommodate, proportionally, larger numbers of cells. The bioreactors can support cell growth for weeks, or even months, depending on the nature of the cell line and the composition of medium.

Example 4

Expression of Recombinant Heparanase in Virus Infected Insect Cells

Experimental Methods

Cells: High five and Sf21 insect cell lines were maintained as monolayer cultures in SF900II-SFM medium (GibcoBRL).

Recombinant Baculovirus: Recombinant virus containing the hpa gene was constructed using the Bac to Bac system (GibcoBRL). The transfer vector pFastBac (see U.S. patent application Ser. No. 08/922,180) was digested with SalI and NotI and ligated with a 1.7 kb fragment of phpa2 digested with XhoI and NotI. The resulting plasmid was designated pFasthpa2. An identical plasmid designated pFasthpa4 was prepared as a duplicate and both independently served for further experimentations. Recombinant bacmid was generated according to the instructions of the manufacturer with pFasthpa2, pFasthpa4 and with pFastBac. The latter served as a negative control. Recombinant bacmid DNAs were transfected into Sf21 insect cells. Five days after transfection recombinant viruses were harvested and used to infect High five insect cells, $3\times10^6$ cells in T-25 flasks. Cells were harvested 2–3 days after infection. $4\times10^6$ cells were centrifuged and resuspended in a reaction buffer containing 20 mM phosphate citrate buffer, 50 mM NaCl. Cells underwent three cycles of freeze and thaw and lysates were stored at $-80°$ C. Conditioned medium was stored at 4° C.

Experimental Results

Degradation of soluble ECM-derived HSPG: Monolayer cultures of High five cells were infected (72 h, 28° C.) with recombinant bacoluvirus containing the pFasthpa plasmid or with control virus containing an insert free plasmid. The cells were harvested and lysed in heparanase reaction buffer by three cycles of freezing and thawing. The cell lysates were then incubated (18 h, 37° C.) with sulfate labeled, ECM-derived HSPG (peak I), followed by gel filtration analysis (Sepharose 6B) of the reaction mixture.

Figure 10:
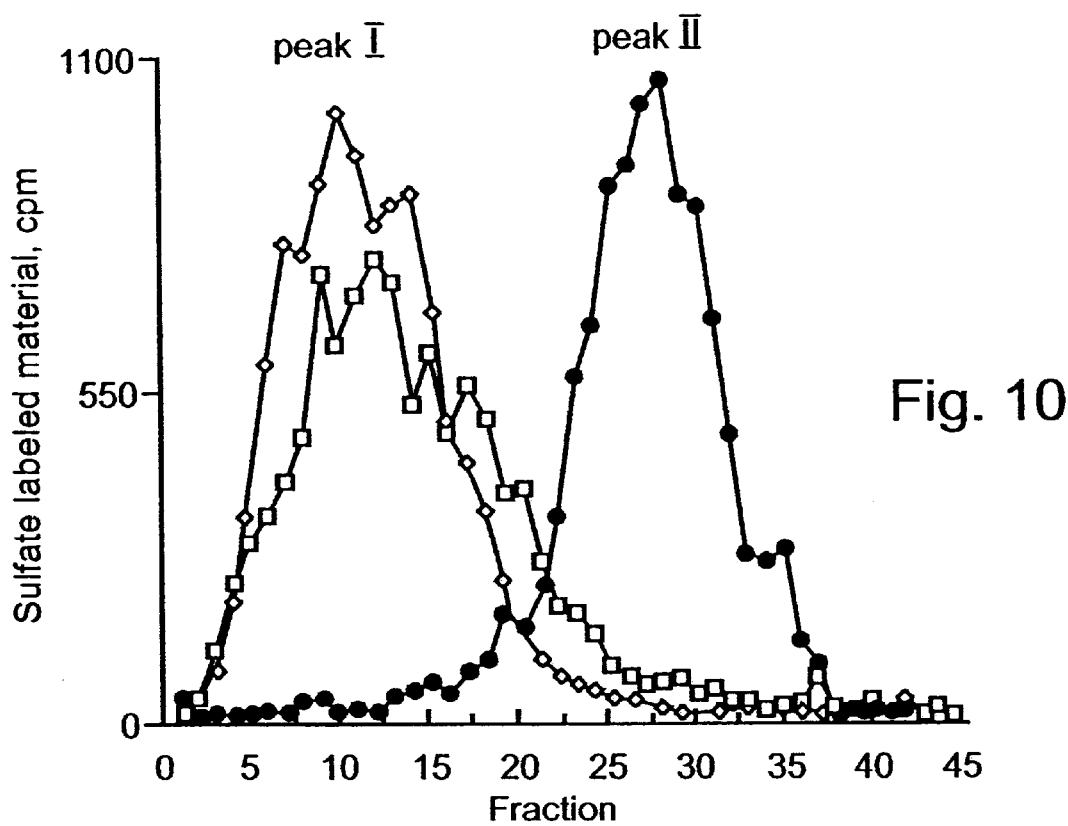
FIG. 10 demonstrates degradation of soluble sulfate labeled HSPG substrate by lysates of High five cells infected with pFhpa2 virus. Lysates of High five cells that were infected with pFhpa2 virus (●) or control pF2 virus (□) were incubated (18 h, 37° C.) with sulfate labeled ECM-derived soluble HSPG (peak I). The incubation medium was then subjected to gel filtration on Sepharose 6B. Low molecular weight HS degradation fragments (peak II) were produced only during incubation with the pFhpa2 infected cells, but there was no degradation of the HSPG substrate (◊) by lysates of pF2 infected cells.

As shown in FIG. 10, the substrate alone included almost entirely high molecular weight (Mr) material eluted next to $V_o$ (peak I, fractions 5–20, Kav<0.35). A similar elution pattern was obtained when the HSPG substrate was incubated with lysates of cells that were infected with control virus. In contrast, incubation of the HSPG substrate with lysates of cells infected with the hpa containing virus resulted in a complete conversion of the high Mr substrate into low Mr labeled degradation fragments (peak II, fractions 22–35, 0.5<Kav<0.75).

Fragments eluted in peak II were shown to be degradation products of heparan sulfate, as they were (i) 5- to 6-fold smaller than intact heparan sulfate side chains (Kav approx. 0.33) released from ECM by treatment with either alkaline borohydride or papain; and (ii) resistant to further digestion with papain or chondroitinase ABC, and susceptible to deamination by nitrous acid. Similar results (not shown) were obtained with Sf21 cells. Again, heparanase activity was detected in cells infected with the hpa containing virus (pFhpa), but not with control virus (pF). This result was obtained with two independently generated recombinant viruses. Lysates of control not infected High five cells failed to degrade the HSPG substrate.

In subsequent experiments, the labeled HSPG substrate was incubated with medium conditioned by infected High five or Sf21 cells.

Figure 11A:
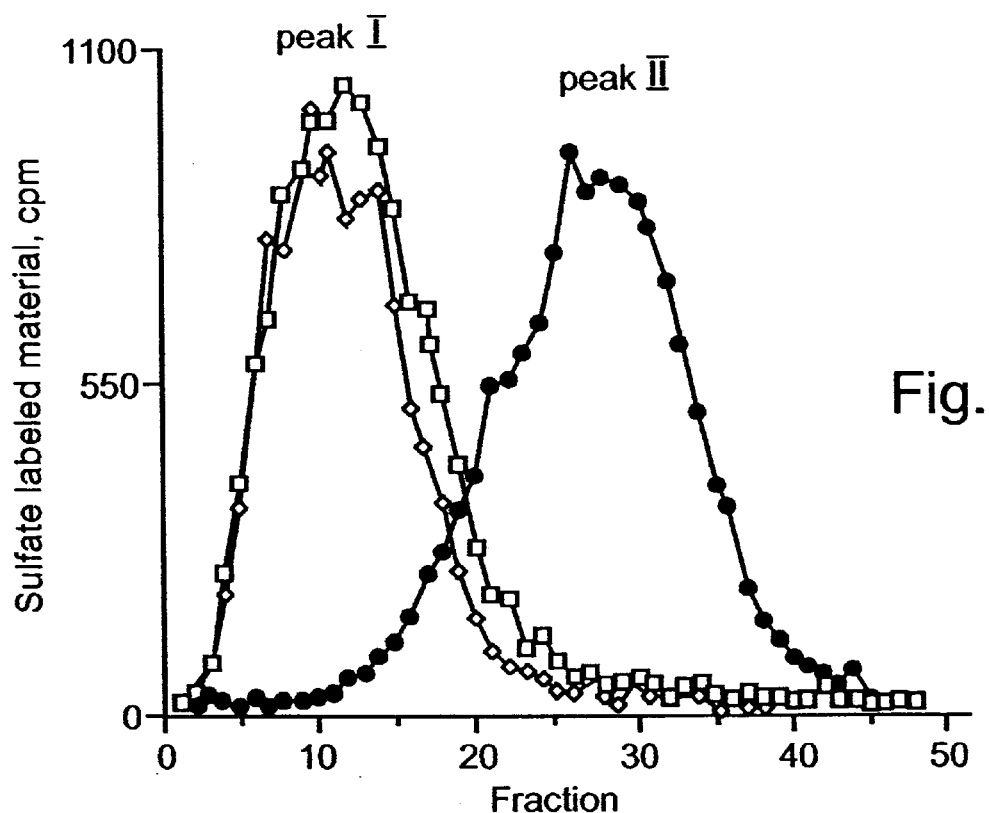
FIGS. 11a–b demonstrate degradation of soluble sulfate labeled HSPG substrate by the growth medium of pFhpa2 and pFhpa4 infected cells. Culture media of High five cells infected with pFhpa2 (11a) or pFhpa4 (11b) viruses (●), or with control viruses (□) were incubated (18 h, 37° C.) with sulfate labeled ECM-derived soluble HSPG (peak I, ◇). The incubation media were then subjected to gel filtration on Sepharose 6B. Low molecular weight HS degradation fragments (peak II) were produced only during incubation with the hpa gene containing viruses. There was no degradation of the HSPG substrate by the growth medium of cells infected with control viruses.
Figure 11B:
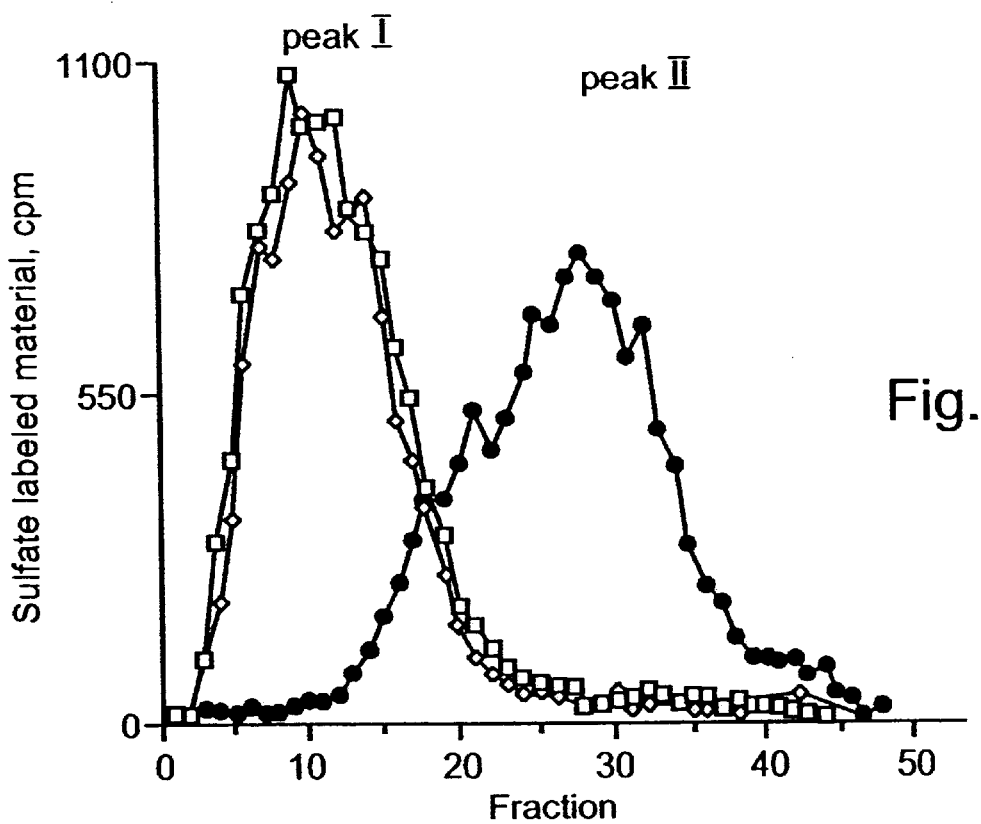

As shown in FIGS. 11a–b, heparanase activity, reflected by the conversion of the high Mr peak I substrate into the low Mr peak II which represents HS degradation fragments, was found in the growth medium of cells infected with the pFhpa2 or pFhpa4 viruses, but not with the control pF1 or pF2 viruses. No heparanase activity was detected in the growth medium of control non-infected High five or Sf21 cells.

The medium of cells infected with the pFhpa4 virus was passed through a 50 kDa cut off membrane to obtain a crude estimation of the molecular weight of the recombinant heparanase enzyme. As demonstrated in FIG. 12, all the enzymatic activity was retained in the upper compartment and there was no activity in the flow through (<50 kDa) material. This result is consistent with the expected molecular weight of the hpa gene product.

In order to further characterize the hpa product the competition effect of heparin, additional substrate of heparanase was examined.

As demonstrated in FIGS. 13a–b, conversion of the peak I substrate into peak II HS degradation fragments was completely abolished in the presence of heparin.

Altogether, these results indicate that the heparanase enzyme is expressed in an active form by insect cells infected with Baculovirus containing the newly identified human hpa gene.

Degradation of HSPG in intact ECM: Next, the ability of intact infected insect cells to degrade HS in intact, naturally produced ECM was investigated. For this purpose, High five or Sf21 cells were seeded on metabolically sulfate labeled ECM followed by infection (48 h, 28° C.) with either the pFhpa4 or control pF2 viruses. The pH of the medium was then adjusted to pH 6.2–6.4 and the cells further incubated with the labeled ECM for another 48 h at 28° C. or 24 h at 37° C. Sulfate labeled material released into the incubation medium was analyzed by gel filtration on Sepharose 6B.

As shown in FIGS. 14a–b and 15a–b, incubation of the ECM with cells infected with the control pF2 virus resulted in a constant release of labeled material that consisted almost entirely (>90%) of high Mr fragments (peak I) eluted with or next to $V_o$. It was previously shown that a proteolytic activity residing in the ECM itself and/or expressed by cells is responsible for release of the high Mr material. This nearly intact HSPG provides a soluble substrate for subsequent degradation by heparanase, as also indicated by the relatively large amount of peak I material accumulating when the heparanase enzyme is inhibited by heparin (FIG. 17). On the other hand, incubation of the labeled ECM with cells infected with the pFhpa4 virus resulted in release of 60–70% of the ECM-associated radioactivity in the form of low Mr sulfate-labeled fragments (peak II, 0.5<Kav<0.75), regardless of whether the infected cells were incubated with the ECM at 28° C. or 37° C. Control intact non-infected Sf21 or High five cells failed to degrade the ECM HS side chains.

In subsequent experiments, as demonstrated in FIGS. 16a–b, High five and Sf21 cells were infected (96 h, 28° C.) with pFhpa4 or control pF1 viruses and the growth medium incubated with sulfate-labeled ECM. Low Mr HS degradation fragments were released from the ECM only upon incubation with medium conditioned by pFhpa4 infected cells. As shown in FIG. 17, production of these fragments was abolished in the presence of heparin, due to its competitory nature. No heparanase activity was detected in the growth medium of control, non-infected cells. These results indicate that the heparanase enzyme expressed by cells infected with the pFhpa4 virus is capable of degrading HS when complexed to other macromolecular constituents (i.e. fibronectin, laminin, collagen) of a naturally produced intact ECM, in a manner similar to that reported for highly metastatic tumor cells or activated cells of the immune system.

Thus, insect cells of several origins (such as Sf21 from *Spodoptera frugiperda* and High five from *Trichoplusia ni*) may be infected productively with baculovirus. Insect cells are infected with recombinant baculovirus in which viral DNA sequences have been replaced with DNA sequences coding for a protein of interest. The protein of interest is expressed during the very late phase of infection. A major advantage of the baculovirus expression system is that it can be used for expressing large amounts of recombinant protein compared to other popular expression systems in eukaryotes (e.g., expression in CHO cells). Another advantage of the system is that insect cells have most of the protein processing capabilities of higher eukaryotic cells. Thus, proteins produced in the recombinant baculovirus-infected cells can undergo co-and post translational processing yielding proteins which are similar to the natural protein.

Scaling up the process of culturing and infecting insect cells with baculovirus is required for the production of recombinant protein of choice, in milligram and up to gram quantities. These quantities may be required for both research or commercial use. Scaling up the process involves a variety of fields, such as medium development, metabolic studies, protein purification and quantification.

Several problems are inherent to this system and effect the process of scaling up. Upon infection, insect cells become increasingly fragile and sensitive to the physiochemical environment of the culture. One of the primary goals of the bioengineer is to oxygenate large scale, high-density culture sufficiently, at low shearing rates. Although oxygen uptake rates of insect cells are similar to mammalian cell lines, it was found that after infection oxygen uptake rates doubles. An optimization process, aimed for setting-up of bioreactor parameters is required, for supplying oxygen to the cells without damaging them.

The spinner Bellco, Cat. 1965-56001 was used for scaling up as described. This is a double-wall type spinner. Temperature was controlled by water circulated from a 12 liter water bath (Fried Electric, Model TEP1) equipped with a heater and a thermostat. The spinner was aerated with both air, using an aquarium pump (Rena 301) and oxygen. An oxygen cylinder (medical grade) was connected to the spinner through a two stage regulator set to a pressure of 2 psi. Both air and oxygen were connected to the spinner through a T-connector equipped with valves that enabled a control over the flow rates of air and of oxygen. A tubing for delivering air mixed with oxygen was connected to the sparger of the spinner through a 0.2μ-size filter. The sparger used was of an open type, releasing air-oxygen mixture through an orifice of 3 mm inner diameter. The stirring function was provided by a low-RPM magnetic stirrer (LH, type 20, LH fermentation Co.), placed beneath the spinner.

High five and Sf21 cells were used alternatively for large scale production of heparanase. Cell culture was gradually built up to $1.2 \times 10^{10}$ cells. Eight shake flasks of 500 ml-size were used for culturing cells to $3 \times 10^6$ cells/ml. Cells were cultured with protein-free medium (Insect-Xpress, Bio Whittaker). 1.5 liters of the above culture was used for seeding a 6 liters-size spinner. At the time of seeding, culture was diluted to 3 liters with fresh medium. Air was sparged into the culture at 0.5 liters/min. Stirring rate was 50 RPM and temperature was set to 28° C. Two days after seeding, culture volume was doubled again, from 3 liters to 6 liters. Cell density was adjusted at that time to $1 \times 10^6$ cells/ml. At that time pure oxygen was sparged at 1.5 liters/min in addition to the sparging of air (at 0.5 liters/minute).

Infection of the culture took place one day after doubling the culture volume from 3 liters to 6 liters, as described. Cells were counted and infected with the heparanase-coding recombinant virus pFhpa2 at a multiplicity of infection (MOI) of 0.1 or 1.0. The infected culture was maintained for approximately 72 hours under conditions set for 6 liters-size culture: Oxygen 1.5 liters/min, air 0.5 liters/min, temperature 28° C., agitation at 50 RPM.

Viability of cells in culture was tested every 4 hours, starting from 62 hours after virus infection and on. Viability of cells was determined by staining cells with Trypan Blue dye. The culture was harvested when viability reached 70–80%. Cells and cell debris were removed by centrifugation (IEC B-22M, Rotor Cat. 878, 20 min. at 4° C. at 7,000 RPM). Supernatants were filtered through 0.2μ size cartridge (Millipore, Cat. KV0304HB3). Virus and small-size debris were removed with a 300 kda-size cross-flow cartridge (Millipore, Cat. CDUF006LM). Heparanase was concentrated from filtrate obtained from the 300 kda-size cartridge with 10 kDa size cross-flow cartridge (Millipore, Cat. SK1P003W4). The final concentrated solution had a volume of between 0.5 liters and 1 liters. Heparanase was purified from the concentrated solution on HPLC. Table 2 below summarizes the results of two large scale heparanase production by insect cells experiments.

TABLE 2

| Batch No. | Cells used | MOI used | Volume of culture (L) | Harvest time post infection (hours) | Cell viability at harvest (%) | heparanase in harvest (mg/ml) |
|---|---|---|---|---|---|---|
| 30 | Sf21 | 0.1 | 4.5 | 78 | 76 | 0.44 |
| 31 | Hi-5 | 0.1 | 6.0 | 75 | 76 | 0.16 |

Example 5

Purification of Recombinant Heparanase

Experimental Methods and Results

Methods and Results: Baculovirus infected insect cells (1 or 5 liter of High five cell suspension) were harvested by centrifugation. The supernatant was passed through 0.2 micron filter (Millipore), then filtered through 300K cartridge (Millipore). The <300 kDa retentate (about 300 ml) was washed by further filtration with 2 volumes of phosphate buffered saline (PBS). The <300 kDa filtrate was then concentrated by 10K cellulose cartridge (Millipore). The >10 kDa retentate was diluted three fold with 10 mM phosphate buffer pH 6.8 to prepare for applying the crude enzyme preparation onto a Source-S column (Pharmacia).

The diluted >10 kDa retentate was subjected to a Source-S column (2.5×10 cm) pre equilibrated with 10 mM phosphate buffer pH 6.8, 50 mM NaCl). Most of the contaminating proteins did not bind to the column while heparanase bound tightly. Heparanase activity was eluted by a linear gradient of 0.05 M NaCl–1 M NaCl in phosphate buffer pH 6.8 and fractions of 5 ml were collected.

The fractions having the highest activity in degrading sulfate labeled ECM were combined. The 0.4 M NaCl fractions were about 90% pure and exhibited the highest activity (FIG. 18, lane 9). A rabbit anti-heparanase polyclonal antibody detected the purified enzyme in Western blot—ECL analysis (FIG. 19, lane 9).

These results demonstrate a powerful single step purification of recombinant heparanase from culture supernatants. Obviously, other purification methods, such as affinity purification using, for example, solid support bound heparanase substrates, heparanase inhibitors or anti-heparanase antibodies, size exclusion, hydrophobic interactions, etc. can be additionally employed.

Example 6

Purification of Heparanase and Production of Highly Active Heparanase Species by Proteolytic Processing Experimental Methods Construction of hpa DNA expression vectors, transfection thereof into cells, selection for dhfr expressing stable cellular clones, induction of secretion and SDS polyacrylamide gel electrophoresis and Western blot analyses were all performed as described hereinabove under Example 3.

Heparanase activity using DMB assay: For each sample, 100 μl heparin sepharose (50% suspension in 1×buffer A—containing 20 mM Phosphate citrate buffer pH 5.4, 1 mM $CaCl_2$ and 1 mM NaCl) were incubated in 0.5 ml eppendorf tube for 17 hours with a tested enzyme preparation. At the end of the incubation period, samples were centrifuged for 2 minutes at 1000 rpm and the supernatants were analyzed for sulfated polyanions (heparin) using the colorimetric dimethylmethylene blue assay as follows.

Supernatants (100 μl) were transferred to plastic cuvettes and diluted to 0.5 ml with PBS supplemented with 1% BSA. 1,9-Dimethylmethylene blue (32 mg dissolved in 5 ml ethanol and diluted to 1 liter with formate buffer) (0.5 ml) was added to each cuvette. Absorbency at 530 nm was determined using a spectrophotometer (Cary 100, Varian). For each sample a control, to which the enzyme was added at the end of the incubation period, was included. For further details, see U.S. patent application Ser. No. 09/113,168, which is incorporated by reference as if fully set forth herein.

Heparanase activity using the tetrazolium assay: Heparanase activity was determined in reactions containing buffer A and 50 μg heparan sulfate in a final volume of 100 μl. Reactions were performed in a 96 well microtiterplate at 37°

C. for 17 hours. Reaction were thereafter stopped by the addition of 100 μl tetrazolium blue reagent (0.1% tetrazolium blue in 0.1 M NaOH) to each well. Color was developed following incubation at 60° C. for 40 minutes. Color intensity was quantitatively determined at 580 nm using a microtiterplate reader (Dynatech). For each sample a control, to which the enzyme was added at the end of the incubation period, was included. A glucose standard curve of 1–15 μg glucose was included in each assay. Heparanase activity was calculated as ΔO.D. of the sample containing the substrate minus the O.D of the control sample. The result was converted to μg glucose equivalent. One unit is defined as μg glucose equivalent produced per minute. For further details, see U.S. patent application Ser. No. 09/113,168, which is incorporated by reference as if fully set forth herein.

Production of rabbit anti-native heparanase polyclonal antibodies: Rabbits were immunized in three two weeks intervals with 200 mg of purified human recombinant heparanase protein produced in baculovirus infected Sf21 insect cells (see Examples 4–5 above) emulsified with an equal volume of complete Freund's adjuvant. Ten days after the third immunization rabbits were bled and serum was examined for reactivity with recombinant heparanase. Four weeks after bleeding another boost was injected and 10 days later blood was collected.

Purification of heparanase from mammalian cell extract using ion exchange chromatography: 2TT1 CHO cells ($2\times10^8$ cells stably transfected with pShpaCdhfr, FIG. 20b) were extracted in 2.5 ml of 10 mM phosphate citrate buffer, pH 5.4. The extract was centrifuged at 2,750×g for 5 minutes and the supernatant was collected for heparanase enzyme purification using cation exchange chromatography as follows. An HPLC column (mono-S HR 5/5, Pharmacia Biotech) was equilibrated with 20 mM sodium phosphate buffer, pH 6.8, and the supernatant was loaded thereon. Proteins were eluted from the column using a linear gradient of 0 to 1 M sodium chloride in 20 mM sodium phosphate buffer, pH 6.8. The gradient was carried out in 20 column volumes at a flow rate of one ml per minute. Elution of proteins was monitored at 214 nm (FIG. 23a) and fractions of 1 ml each were collected. An aliquot from each fraction was analyzed for heparanase activity using the DMB assay and for immunoreactivity using a mouse anti-heparanase monoclonal antibody (see U.S. patent application Ser. No. 09/071,739, which is incorporated herein by reference). Most of the heparanase was eluted in fractions 19–20.

Preparation of an affinity column with anti-native heparanase antibodies: An affinity column was prepared using the Immunopure Protein G IgG Orientation Kit (Pierce). To this end, 17 mg of the above described rabbit anti-native heparanase polyclonal antibody, purified on protein G sepharose, were bound to a column containing 2 ml Immunopure immobilized protein G. The antibody was cross linked to the protein G with DMP. Unreacted imidate groups were blocked and the column was equilibrated with 20 mM phosphate buffer, pH 6.8.

Purification of heparanase using the affinity column: $0.5\times10^8$ 2TT1 CHO cells were suspended in 2.5 ml of 20 mM phosphate citrate buffer, pH 5.4. Cells were frozen in liquid nitrogen and subsequently thawed at 37° C. Freezing and thawing were repeated two more times. The extract was then centrifuged for 15 minutes at 4000 g and the resulting supernatant was loaded onto the affinity column and was incubated, to allow binding of the enzyme to the column, at 4° C. for 17 hours under head-over-tail shaking. Thereafter, unbound proteins were washed until absorbency at 280 nm reached zero. Proteins were eluted from the column with 0.1 M glycine HCI buffer, pH 3.5. 900 μl fractions were collected into eppendorf tubes each containing 100 μl of 1 M phosphate buffer, pH 8. The presence of heparanase in the eluted fractions was determined by Western blotting following gradient 4–20% SDS-PAGE of 20 μl samples using anti-heparanase monoclonal antibody (see U.S. patent application Ser. No. 09/071,739). Heparanase activity was determined in 30 μl samples using the above described DMB assay.

Construction of heparanase expression vectors with a unique protease cleavage sequence: Expression vectors for the production of a heparanase protein species carrying a unique proteolytic cleavage site were designed and constructed. Two independent sites, just upstream of amino acids 120 or 158 (SEQ ID NO:2), both are peaking on the hydropathy plot, as calculated by the Kyte-Doolittle method for calculating hydrophilicity, using the Wisconsin University GCG DNA analysis software (FIG. 29a), were selected for insertion of either one of two protease recognition and cleavage sequences within the hpa cDNA sequence to yield two heparanase species designated herein as pre-p56' and pre-p52', which, following digestion with their respective protease, yield truncated proteins designated herein p52' and p56', respectively. A first sequence included 4 amino acids (Ile-Glu-Gly-Arg↓, SEQ ID NO:13) which constitute a factor Xa recognition and cleavage sequence. An alternative, second, sequence included 5 amino acids (Asp-Asp-Asp-Asp-Lys↓, SEQ ID NO:14) which constitute a enterokinase recognition and cleavage sequence. These sequences do not appear in the natural enzyme (SEQ ID NO:2).

To this end, the following PCR primers were constructed: 52-Xa—5'-CCATCGATAGAAGGACGAAAAAAG TTCAAGAACAGCACCTAC-3' (SEQ ID NO:15); 52x-Cla—5'-GGATCGATTGGTAGTGTTCTCGGAGTAG-3' (SEQ ID NO:16); 56-Xa—5'-GGATCGATA GAAGGACGATCTCAAGTCAACCAGGATATT-3' (SEQ ID NO:17); 56x-Cla—5'-CCATCGAT GCCCAGTAACTTCTCTCTTCAAAG-3' (SEQ ID NO:18); hp1 967—5'-TCAGATGC AAGCAGCAACTTTGGC-3' (SEQ ID NO:19); hpu 685—5'-GAGCAGCCA GGTGAGCCCAAGAT-3' (SEQ ID NO:20); 52-EK 5'-CCATCGATGA CGACGACAAGAAAAAGTTCAAGAACAGCACCTAC-3' (SEQ ID NO:21); 52e-Cla—5'-GGATCGATCTGG TAGTGTTCTCGGAGTAG-3' (SEQ ID NO:22); 56-EK—5'-GGATCGATGACG ACGACAAGTCTCAAGTCAACCAGGATATTTG-3' (SEQ ID NO:23); and 56e-Cla—5'-CCATCGATTTGGGAGTAACTTCTCTCTTCAAAG-3' (SEQ ID NO:24).

The following constructs were prepared (FIG. 29b):

(i) Construction of pre-p52'-Xa hpa in pFast: A first PCR reaction was performed with a pFasthpa2 template and with primers 52-Xa and hpl 967. The resulted 1180 bp fragment was digested with ClaI and AflII and a 220 bp fragment was isolated. A second PCR reaction was performed with a pFasthpa2 template and with primers 52x-Cla and hpu 685. The resulting 500 bp fragment was digested with ClaI and AatII and a 370 bp fragment was isolated. The ClaI-AflII 220 bp and the ClaI-AatII 370 bp fragments were ligated to a 5,900 AatII-AflII fragment of the pFasthpa2 plasmid.

(ii) Construction of pre-p56'-Xa hpa in pFast: A first PCR reaction was performed with a pFasthpa2 template and with primers 56-Xa and hpl 967. The resulted 1290 bp fragment was digested with ClaI and AflII and a 340 bp fragment was isolated. A second PCR reaction was performed with a pFasthpa2 template and with primers 56x-Cla and hpu 685. The resulting 380 bp fragment was digested with ClaI and AatII and a 250 bp fragment was isolated. The ClaI-AflII 340 bp and the ClaI-AatII 250 bp fragments were ligated to a 5,900 AatII-AflII fragment of the pFasthpa2 plasmid.

(iii) Construction of pre-p52'-Enterokinase hpa in pFast: A first PCR reaction was performed with a pFasthpa2 template and with primers 52-EK and hpl 967. The resulted 1180 bp fragment was digested with ClaI and AflII and a 220 bp fragment was isolated. A second PCR reaction was performed with a pFasthpa2 template and with primers 52e-Cla and hpu 685. The resulting 500 bp fragment was digested with ClaI and AatII and a 370 bp fragment was isolated. The ClaI-AflII 220 bp and the ClaI-AatII 370 bp fragments were ligated to a 5,900 AatII-AflII fragment of the pFasthpa2 plasmid.

(iv) Construction of pre-p56'-Enterokinase hpa in pFast: A first PCR reaction was performed with a pFasthpa2 template and with primers 56-EK and hpl 967. The resulted 1290 bp fragment was digested with ClaI and AflII and a 340 bp fragment was isolated. A second PCR reaction was performed with a pFasthpa2 template and with primers 56e-Cla and hpu 685. The resulting 380 bp fragment was digested with ClaI and AatII and a 250 bp fragment was isolated. The ClaI-AflII 340 bp and the ClaI-AatII 250 bp fragments were ligated to a 5,900 AatII-AflII fragment of the pFasthpa2 plasmid.

Construction of plasmids for expression of heparanase with protease digestion sequence: Each one of the four constructs (i to iv) described hereinabove includes an AatII-AflII fragment which includes a factor Xa or enterokinase recognition and cleavage sequence positioned at one of the described alternative sites, i.e., upstream amino acids 120 or 158 (SEQ ID NO:2). The hpa constructs described in FIGS. 5a–e and 20a–e, as well as the pFasthpa constructs, each includes a single AatII site and a single AflII site within the hpa cDNA sequence, thus enabling the insertion by replacement of the 220 or 340 AatII-AflII fragments as desired.

Experimental Results

Expression of hpa DNA in animal cells: As already shown and discussed under Example 3 above, in order to drive transient or stable expression of the hpa gene in animal cells, the hpa gene was cloned into expression vectors, where transcription is regulated by promoters of viral origin (SV40, CMV) to ensure efficient transcription (FIGS. 5a–e). All vectors were suitable for transient expression of hpa in animal cells, but only vectors that include an expression cassette for the mouse dhfr gene (FIGS. 5b and 20f, the latter serves as a negative control) could be subjected to selection by mrthotrexate (MTX). Selection enables the establishment of cell lines that constitutively produce high levels of recombinant heparanase.

Cell lines of different origins have been transfected and expressed human heparanase gene: Transient expression of recombinant heparanase was detected in a human kidney fibroblasts cell line 293 (FIG. 6a), baby hamster kidney cells (BHK21; FIG. 21a) and Chinese hamster ovary cells (CHO; FIG. 6b). Stable expression of heparanase in CHO cells is shown in FIGS. 6a–b.

Transfection of CHO cells with the expression vector pShpaCdhfr (FIG. 5b) or co-transfection with pS1hpa and pCdhfr (FIGS. 5c and 20f), followed by selection for MTX resistant clones resulted in the isolation of numerous clones. These cellular clones express hpa gene products in a constitutive and stable manner (FIG. 6a, lanes 1–3).

Analysis of expression of recombinant heparanase in mammalian cells revealed two distinct specific protein products: a large protein of about 70 kDa (which is referred to herein as p70) and a predominant protein of about 50 kDa, which is referred to herein as p52 (FIGS. 6a, 21a).

Although the hpa DNA encodes a large 543 amino acids protein (expected molecular weight about 61 kDa), the results clearly demonstrate the existence of two proteins. These observations are similar to the results of the transient hpa gene expression in human 293 cells (FIG. 6a, lane 4). BHK21 cells, transiently transfected with pS1hpa (FIG. 5c) express predominantly the p52 form of recombinant heparanase (FIG. 21a, lane 1 marked by an arrow). Stable CHO clones express predominantly the p52 protein (FIG. 6b, lane 2).

The presence of both p70 and p52 heparanase was detected in all cells that expressed the hpa gene, although the relative concentrations of the proteins varied between different cell types.

Cells transfected with pS1hpa (FIG. 5c) expressed p52 (FIG. 21a) indicating that the replacement of the putative heparanase signal peptide by the PPT signal sequence did not affect the expression and processing of the protein.

All cell extracts exhibited high heparanase activity following the introduction of the hpa gene. Human. 293 cells transfected with pShpa (FIG. 5e) exhibited high heparanase activity (FIG. 21b).

It has been previously shown that a 52 kDa protein with heparanase activity was isolated from placenta (61) an platelets (62).

It is thus concluded that the p70 protein is a preheparanase that is naturally processed in the host cell to yield the p52 protein.

Heparanase secretion into the growth medium: For large scale production and purification purposes, secretion of the recombinant protein into the growth medium is highly desirable. Therefore, expression vectors were constructed (pS1hpa and pS2hpa, FIGS. 5c–d) to direct translation of heparanase attached to the PPT signal peptide, a secretion signal peptide.

Both pS1hpa and pS2hpa plasmids directed the expression of protein product with heparanase activity in human 293 or CHO cells (FIGS. 7c, 22a–b). Transient expression of heparanase from pS1hpa and pS2hpa resulted in the appearance of a single size (about 70 kDa) heparanase protein in the medium (FIG. 7c, lanes 3–6), similar to the larger form of recombinant heparanase detected in the cells.

CHO cells, stably transfected with either pShpaCdhfr (2TT1 clones) or pS1hpa (S1PPT clones) were further subcloned to yield stable clones which maintain their genetic and cellular characteristics stability in the absence of MTX selection. To this end, the limiting dilution procedure was employed, in which cells were cloned under non-selective conditions and clones exhibiting the above stability were selected for further analysis.

2TT1 and S1PPT clones under (clones 2TT1 and SlPPT-p) or after (clones 2TT1-2, 2TT1-8, S1PPT-4 and S1PPT-8) selection with high MTX yielded stable clones exhibiting moderate (clones 2TT1 (FIG. 22b), 2TT1-2, 2TT1-8) or high (clones S1PPT-p, S1PPT-4, S1PPT-8 (FIG. 22a)) constitutive secretion of heparanase into the growth medium. The secreted protein was of about 70 kDa, similar to p70, the larger heparanase form found within the cells (FIGS. 22a–b). Only when a large amount of p70 protein are found in the medium, a residual amount of the smaller heparanase form, p52, could be detected (FIG. 22a, lane 4).

In the conditioned medium containing heparanase, some heparanase activity could be detected, although not as high as the activity measured in the respective cell extracts which, as determined immunologically, have comparable heparanase concentrations. Some improvement in secretion could be detected by calcium ionophore treatment, but the effect was transient (FIG. 22a, lane 4).

The purification of recombinant heparanase from 2TT1 CHO cells by ion exchange chromatography: Clone 2TT1-8 was used for large scale production of heparanase. In this cell line, the p52 form of heparanase is predominantly expressed within the cells. The cells are grown adherent to the tissue culture flask surface and were harvested when the cell culture reaches confluency.

Purification of a non-abundant protein from cells is a challenging task, where only an carefully designed and accurately discriminating protocol enables purification. See U.S. Pat. No. 5,362,641 and references 61 and 62 describing the purification of heparanase from placenta and platelets.

Here, a cation exchange chromatography procedure was selected for purification based on successful use thereof in the purification of insect cells produced recombinant heparanase, as described in Example 5 hereinabove.

Separation of the total protein content of 2TT1-8 cell extract on a mono-S cation exchange column is shown in FIG. 23a. The vast majority of cellular proteins were eluted from the column prior to the elution of heparanase (FIG. 23b). It is important to note that the p52 and the p70 were co-eluted under these conditions. Furthermore, a tight correlation was found between the presence of heparanase, as detected immunologically (FIG. 23b), and its activity, as measured by the DMB (FIG. 23c) and the tetrazolium (FIG. 23d) activity assays.

Thus, using the above described purification protocol, one obtains ample amounts of highly active and purified heparanase which is highly suitable for use in a high throughput screening assay for heparanase activity, e.g., in the presence of candidate heparanase inhibitors, for example, combinatorial inhibitor libraries. Further details relating to a heparanase high throughput assay are provided in U.S. patent application Ser. No. 09/113,168, which is incorporated herein by reference.

The purification of heparanase by an anti-heparanase affinity column: Partially purified, active recombinant heparanse produced in SF21 insect cells infected with a baculovirus containing the hpa cDNA, was used to immunize rabbits for the production of polyclonal antibodies against the native recombinant heparanase protein. This antibody was thereafter purified and was used to construct a heparanase affinity column.

Cellular extract of CHO 2TT1-8 cells was loaded on the column for affinity separation. FIGS. 24a–b clearly show that heparanase was specifically and efficiently bound to the affinity column. Moreover, high salt elution of the bound heparanase from the column was efficient and the activity of the eluted heparanase (FIG. 24b) was tightly correlated with the presence of the recombinant enzyme (FIG. 24a). Thus, using an affinity column as herein described, one can obtain a highly purified and highly active recombinant or natural heparanase in single step purification, which can be used in pharmaceutical applications. Furthermore, combining the Mono-S and affinity columns into a two step purification procedure, will ensure even better results in terms of both purification and yield.

In addition, the tetrazolium assay is based on the detection of free reducing sugar ends. As such it requires heparanase preparations devoid of such reducing ends. Heparanase purified using the above described affinity column is devoid of such reducing ends, and is therefore highly applicable for the tetrazolium activity assay.

Proteolytic processing of heparanase by protease from insect cells: Production of human recombinant heparanase in insect cells (Sf21), via baculovirus infection, and the subsequent purification of that protein are described in U.S. patent application Ser. Nos. 08/922,170; 09/071,618; 09/109,386; and in PCT/US98/17954, all of which are incorporated herein by reference.

Briefly, conditioned medium of Sf21 cells that were infected with recombinant baculovirus, secrete heparanase to the medium. This heparanase is a glycosylated protein with an apparent molecular weight of 70 kDa. The size of that protein is similar to the p70 produced by mammalian cells, and it possesses limited heparanase activity. This heparanase protein is referred to herein as p70-bac heparanase.

Purification of p70-bac heparanase from insect cells conditioned medium involved sequential filtration steps and a cation exchange column (Source-S). Fractions that contain predominantly p70-bac heparanase protein are collected. This purification protocol and results are described hereinabove.

The effect of different pH values on the activity and intactness of p70-bac heparanase was examined in an attempt to establish a pH optimum for heparanase activity. It was found that exposure of p70-bac heparanase to pH 4.0 for one week at 4° C. resulted in significant (seven fold) increase in activity (FIG. 25b). This activation was protease dependent as is evident form the inhibition of activation caused by a protease inhibitors cocktail (FIG. 25b).

The fate of the p70-bac heparanase following exposure to acidic pH was uncovered by Western-blot analysis (FIG. 25a). Following exposure to pH 4, p70-bac heparanase was converted into a lower molecular weight form, of about 56 kDa, which is referred to herein as p56 (FIG. 25a, lane C). Proteolysis was inhibited in the presence of protease inhibitors (FIG. 25a, lane B).

This is the first record demonstrating (i) in vitro proteolytic processing of recombinant heparanase, (ii) associated with a significant increase in heparanase activity.

To further characterize the protease(s) involved in processing and activation of p70-bac heparanase, a collection of individual protease inhibitors was employed (FIGS. 25c–d). The inhibitors antipain, E-64, leupeptin and chemostatin were most effective in preventing the activation of p70-bac heparanase at low pH. The effect was due to inhibition of the proteolytic processing of the p70-bac heparanase as is evident from the Western blot analysis of FIG. 25c. Antipain and leupeptin are known to inhibit serine and cysteine proteases, while E-64 inhibits only cysteine proteases. These results therefore indicate that a cysteine protease(s) present in the conditioned medium of insect cells are responsible for the activation of p70-bac heparanase, by processing the enzyme into a lower and more active p56 molecular weight form.

N-terminal sequencing of gel separated and PVDF transferred p56 heparanase revealed the sequence Ser-Gln-Val-Asn-Gln (SEQ ID NO:25), which corresponds to a new heparanase species that starts at Ser 120 of the full length enzyme (SEQ ID NO:2).

Proteolytic processing of heparanase by trypsin and cathepsin L: The activation of p70-bac heparanase by protease(s) from insect cells conditioned medium could be reproduced by mild digestion with trypsin (FIGS. 26a–b). Trypsin, 1.5 to 500 units per 10 μg p70-bac heparanase, gradually activated the protein, reaching maximal activation of five-fold lo already at 15 units trypsin (FIG. 26a). Activation of p70-bac heparanase correlated with the expected cleavage of a portion of the p70-bac heparanase into smaller heparanase species, of about 56 kDa (FIG. 26b). Smaller fragments of heparanase were also obtained by trypsinization (FIG. 26b, lanes 2–3).

Similarly, recombinant heparanase processing and activation occurred when mild trypsin digestion was employed on a crude conditioned medium of CHO cells that secrete mammalian p70 heparanase (FIG. 27).

Activation was dose dependent.

Processing and activation of recombinant CHO produced and secreted heparanase (p70) was also obtained by mild treatment with Cathepsin L, which is a known cysteine protease (FIGS. 28a–b). Processing by this protease resulted in several digestion products, of about 56, 34 and 21 kDa (FIG. 28b, lane 2).

It is shown herein that proteolytic digestion of recombinant heparanase from a variety of sources and by a variety of proteases results in (i) processing of the enzyme into a lower molecular weigh species; and (ii) increased catalytic activity. Processing and activation of heparanase in a similar fashion is anticipated to take place in vivo as well and therefore in vivo inhibition of proteases can be used to indirectly inhibit heparanase processing and activation.

Design of expression vectors to express heparanase precursor species adapted for in vitro activation by proteases: The p52 heparanase protein (as characterized in CHO, 293 and BHK21 cells, placental and platelets heparanase) and the p56 heparanase protein (as characterized after processing of the p70-bac heparanase) are presently the forms of heparanase that exhibit the highest enzymatic activity. It is shown herein that these heparanase species are the result of proteolytic cleavages of heparanase. As was determined by solid phase microsequencing the cleavage site of p70-bac heparanase is effected between amino acids 119 and 120 (SEQ ID NO:2, see above) within the first peak of hydrophilicity (FIG. 29a, peak I). The second peak of hydrophilicity (FIG. 29a, peak II) is expected to contain the cleavage site yielding the p52 heparanase species. This is not surprising, considering the fact that these regions, are positioned at the surface of the heparanase molecule and are thus susceptible to proteolysis.

FIG. 29c demonstrates the steps undertaken in constructing four basic nucleic acid constructs harboring a unique protease recognition and cleavage sequence of factor Xa—Ile-Glu-Gly-Arg↓ (SEQ ID NO:13)— or of enterokinase—Asp-Asp-Asp-Asp-Lys↓ (SEQ ID NO:14) downstream amino acids 119 or 157. AatII-AflII restriction fragments derived from these four basic constructs can be used to replace a corresponding region in any of the hpa constructs described herein (FIGS. 5a–e) and for that effect, any other construct harboring a hpa derived sequence. FIG. 29b shows the modified heparanase species (pre-p56' and pre-p52') that contain these unique protease recognition and cleavage sequences (shaded regions) which enable proteolytic processing by the respective proteases to obtain homogeneously processed and highly active heparanase species (p56' and p52', respectively).

The above described constructs are highly suitable for expression of heparanase in any expression system which is characterized by secretion of the recombinant heparanase to the growth medium. Such a precursor enzyme can be readily and precisely processed into a mature active form of heparanase—p56' or p52'.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES:

1. Jackson et al 1991, Pysiol Rev 71: 481–539.
2. Bemfield et al 1992 Annu Rev Cell Biol 8: 365–393).
3. Wight, T. N., Kinsella, M. G., and Qwarnstromn, E. E. (1992). The role of proteoglycans in cell adhesion, migration and proliferation. Curr. Opin. Cell Biol., 4,793–801.
4. Jackson, R. L., Busch, S. J., and Cardin, A. L. (1991). Glycosaminoglycans: Molecular properties, protein interactions and role in physiological processes. Physiol. Rev., 71, 481–539.
5. Wight, T. N. (1989). Cell biology of arterial proteoglycans.
   Arteriosclerosis, 9, 1–20.
6. Kjellen, L., and Lindahl, U. (1991). Proteoglycans: structures and interactions. Annu. Rev. Biochem., 60,443–475.
7. Ruoslahti, E., and Yamaguchi, Y. (1991). Proteoglycans as modulators of growth factor activities. Cell, 64, 867–869.
8. Vlodavsky, I., Bar-Shavit, R., Komer, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
9. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
10. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127.
11. Nakajima, M., Irimura, T., and Nicolson, G. L. (1988). Heparanase and tumor metastasis. J. Cell. Biochem., 36, 157–167.
12. Vlodavsky, I. et al. Invasion Metastasis 1995, 14:290–302.
13. Nakagima, M. et al J. Cell. Biochem. 1988, 36:157–167.
14. Vlodavsky, I. et al. Cancer res. 1983, 43:2704–2711.
15. Vlodavsky, I. et al. J. Med 1988, 24:464–470.
16. Vlodavsky, I. et al. Invasion and Metastasis 12:112–127.
17. Gilat, D. et al. J. Exp. Med. 1995, 181:1929–1934.
18. Matzner et al. 1985, J. Clin. Invest. 10:1306–1313.
19. Mollinedo, F. et al. Biochem. J. 1997, 327:917–923.
20. Murphy, G. et al. Biochem. J. 1990, 192:517–525.
21. Nakajima, M. et al. J. Cell. Biochem. 1988, 36(2):157–167.
22. Ishai-Michaeli R. wt al. Cell Reg. 1990, 1:833–842.
23. Cardon-Cardo C. et al. Lab. Inrest. 1990, 63:832–840.
24. Nicolson, G. L. (1988). Organ specificity of tumor metastasis: Role of preferential adhesion, invasion and growth of malignant cells at specific secondary sites. Cancer Met. Rev., 7, 143–188.
25. Liotta, L. A., Rao, C. N., and Barsky, S. H. (1983). Tumor invasion and the extracellular matrix. Lab. Invest., 49, 639–649.
26. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711.
27. Vlodavsky, I., Ishai-Michaeli, R., Bar-Ner, M., Fridman, R., Horowitz, A. T., Fuks,Z. and Biran, S. (1988). Involvement of heparanase in tumor metastasis and angiogenesis. Is. J. Med., 24, 46–470.
28. Parish, C. R., Coombe, D. R., Jakobsen, K. B., and Underwood, P. A. (1987). Evidence that sulphated polysaccharides inhibit tumor metastasis by blocking tumor cell-derived heparanase. Int. J. Cancer, 40,511–517.
29. Burgess, W. H., and Maciag, T. (1989). The heparin-binding (fibroblast) growth factor family of proteins. Annu. Rev. Biochem., 58, 575–606.
30. Folkman, J., and Klagsbrun, M. (1987). Angiogenic factors. Science, 235,442–447.
31. Vlodavsky, I., Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. Proc. Natl. Acad. Sci. USA, 84, 2292–2296.
32. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. Am. J. Pathol., 130, 393–400.
33. Bashkin, P., Doctrow, S., Klagsbrun, M., Svahn, C. M., Folkman, J., and Vlodavsky, I. (1989). Basic fibroblast growth factor binds to subendothelial extracellular matrix and is released by heparitinase and heparin-like molecules. Biochemistry, 28, 1737–1743.
34. Ishai-Michaeli, R., Svahn, C.-M., Chajek-Shaul, T., Korner, G., Ekre, H.-P., and Vlodavsky, I. (1992). Importance of size and sulfation of heparin in release of basic fibroblast factor from the vascular endothelium and extracellular matrix. Biochemistry, 31, 2080–2088.
35. Ishai-Michaeli, R., Eldor, A., and Vlodavsky, I. (1990). Heparanase activity expressed by platelets, neutrophils and lymphoma cells releases active fibroblast growth factor from extracellular matrix. Cell Reg., 1, 833–842.
36. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271.
37. Vlodavsky, I., Bar-Shavit, R., Komer, G., and Fuks, Z. (1993). Extracellular matrix-bound growth factors, enzymes and plasma proteins. In Basement membranes: Cellular and molecular aspects (eds. D. H. Rohrbach and R. Timpl), pp327–343. Academic press Inc., Orlando, Fla.
38. Yayon, A., Klagsbrun, M., Esko, J. D., Leder, P., and Ornitz, D. M. (1991). Cell surface, heparin-like molecules are required for binding of basic fibroblast growth factor to its high affinity receptor. Cell, 64, 841–848.
39. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerization, activation, and cell proliferation. Cell, 79, 1015–1024.
40. Ornitz, D. M., Herr, A. B., Nilsson, M., West, a., J., Svahn, C.-M., and Waksman, G. (1995). FGF binding and FGF receptor activation by synthetic heparan-derived di- and trisaccharides. Science, 268, 432–436.
41. Gitay-Goren, H., Soker, S., Vlodavsky, I., and Neufeld, G. (1992). Cell surface associated heparin-like molecules are required for the binding of vascular endothelial growth factor (VEGF) to its cell surface receptors. J. Biol. Chem., 267, 6093–6098.
42. Campbell, K. H., Rennick, R. E., Kalevich, S. G., and Campbell, G. R. (1992) Exp. Cell Res. 200,156–167.
43. Lider, O., Baharav, E., Mekori, Y., Miller, T., Naparstek, Y., Vlodavsky, I. and Cohen, I. R. Suppression of experimental autoimmune diseases and prolongation of allograft survival by treatment of animals with heparinoid inhibitors of T lymphocyte heparanase. J. Clin. Invest. 83:752–756, 1989.
44. Rapraeger, A., Krufka, A., and Olwin, B. R. (1991). Requirement of heparan sulfate for bFGF-mediated fibroblast growth and myoblast differentiation. Science, 252, 1705–1708.
45. Shieh, M-T., Wundunn, D., Montgomery, R. I., Esko, J. D., and Spear, P. G. J. (1992). Cell surface receptors for herpes simplex virus are heparan sulfate proteoglycans. J Cell Biol., 116, 1273–1281.
46. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. Nature Medicine 3, 866–871.
47. Putnak, J. R., Kanesa-Thasan, N., and Innis, B. L. (1997). A putative cellular receptor for dengue viruses. Nature Medicine 3, 828–829.
48. Narindrasorasak, S., Lowery, D., Gonzalez-DeWhitt, P., Poorman, R. A., Greenberg, B., Kisilevsky, R. (1991). High affinity interactions between the Alzheimer's beta-amyloid precursor protein and the basement membrane form of theparan sulfate proteoglycan. J. Biol. Chem., 266, 12878–83.
49. Eisenberg, S., Sehayek, E., Olivecrona, T., and Vlodavsky, I. (1992). Lipoprotein lipase enhances binding of lipoproteins to heparan sulfate on cell surfaces and extracellular matrix. J. Clin. Invest., 90, 2013–2021.
50. Ross, R. (1993). The pathogenesis of atherosclerosis: a perspective for the 1990s. Nature (Lond.)., 362:801–809.
51. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. J. Biol. Chem., 268, 10160–10167.
52. Yan, S., Sameni, M. and Sloane, B. F. (1998) Cathepsin B and human tumor progression. Biol Chem 379: 113–123.
53. Sloane B F 1990, Cathepsin B and cystatins: evidence for a role in cancer progression. Sem Cancer Biol 1: 137–152.
54. Buck, M. R., Karustis, D. G., Day, N. A., Honn, K. V., and Sloane, B. F. (1992) Degradation of extracellular matrix proteins by human cathepsin B from normal and tumor tissues. Biochem J 282: 273–278.
55. Kobayashi H, Schmitt M, Goretzki L, Chucholowski N, Calvete J, Kramer M, Gunzler W A, Janicke F, Graeff H 1991 cathepsin B efficiently activates the soluble and the tumor cell receptor bound form of the proenzyme urokinase type plasminogen activator (pro-uPA). J Biol Chem 266: 5147–5152.

56. Machledit, W., Assfalg-Machledit, I., Jochum, M., Janick, F. and Schmitt, M. (1992) Lysosomal cysteine proteinases as mediators of inflammation and tumor spread: control of their extracellular activity Fibrinolysis 6: 125–129.
57. Schwart, J. D., Shamamian, P., Monea, S., Whiting, D., Marcus, S. G., Galloway, A. C. and Mignatti, P. (1998) Activation of tumor cell matrix metalloproteinase-2 by neutrophil proteinases requires expression of membrane type 1 matrix methalloproteinase Surgery 124:232–238.
58. Kleiner D E, Stetler-Stevenson W G, 1993 Structural biochemistry and activation of matrix metalloproteinases. Curr Opin Cell Biol 5:891–7
59. Mignatti P, Rifkin D B, 1993 Biology and biochemistry of proteinases in tumor invasion Physiol Rev 73: 161–95.
60. Bellott E. M., Bondaryk R. and Luther A. L. Closing the loop in combinatorial chemistry. European Pharmaceutical Contractor: Aug. 1–6, 1997.
61. Goshen R. et al. Molec. Human Reprod. 1996, 2:679–684.
62. Freeman C. and Parish C. R. Biochem. J., 1998, 336:1341–1350.
63. Harlow and Lane, 1988 Antibody, Cold Spring Harbor.
64. Morrison et al., 1984, Proc. Natl. Acad. Sci. USA 81:6851.
65. Neuberger et al., 1984, Nature 312:604–8.
66. Goding in, Monoclonal Antibodies: Principles and Practice, 2nd ed., pp. 104–126, 1986, Orlando, Fla., Academic Press.
67. Kane, S. in Genetic Engineering 13:167–182, Setlow, J. K. Ed. Plenum Press, New-York.
68. Makrides, S. C. et al. 1996, Microbiological Rev. 60:512–538.
69. Romanos, M. Curr. Opinion. Biotech. 1995, 6:527–533.
70. Williams, D. C., et al. Science 1982, 215:687–689.
71. Cleland, J. L. and Wang D. I. C. in Bioprocessing, Vol. 3, Stephanopoulos, G. N. Ed. VCH publishers, Germany, 1993.
72. Chubat et al. Biotechniques 1996, 20:136–141.
73. Molecular Cloning (1989) Sambrook, J., Frisch, E. F., and Maniatis T. Eds. CSH laboratory press.
74. De Vouge et al. 1994, Int. J. Cancer 56:286–294.
75. Kaduri et al. Colloids and Surfaces B: Biointerfaces 1994, 2: 265–272.
76. Freshey, R. I. Animal cell culture, IRL press, U.K., 1992.

What is claimed is:

1. A method of activating a mammalian heparanase protein, the method comprising digesting the mammalian heparanase protein with a protease capable of cleaving said mammalian heparanase protein at a region containing its most hydrophilic sites present within the first 170 N terminal amino acids of said mammalian heparanase protein, as determined using the Kyte-Doolittle method for calculating hydrophilicity, using the Wisconsin University GCG DNA analysis software, so as to release a catalytically active portion of said mammalian heparanase.

2. The method of claim 1, wherein said protease is selected from the group consisting of a cysteine protease, an aspartyl protease, a serine protease and a metalloproteinase.

3. The method of claim 1, wherein said step of digesting the mammalian heparanase protein by said protease is effected at a pH in which said protease is active.

4. The method of claim 1, wherein said step of digesting the mammalian heparanase protein by said protease is effected at a pH in which said protease has an optimal protease activity.

5. A method of activating a modified mammalian heparanase protein, wherein the modified mammalian heparanase protein comprises an introduced protease cleavage recognition sequence at a region containing the most hydrophilic sites present within the first 170 N terminal amino acids of a natural mammalian heparanase protein as determined using the Kyte-Doolittle method for calculating hydrophilicity, using the Wisconsin University GCG DNA analysis software, the method comprising digesting the modified mammalian heparanase protein with a matching protease being capable of cleaving said introduced protease cleavage recognition sequence.

6. The method of claim 5, wherein said protease is selected from the group consisting of a cysteine protease, an aspartyl protease, a serine protease and a metalloproteinase.

7. The method of claim 5, wherein digesting the modified mammalian heparanase protein by said matching protease is effected at a pH in which said protease is active.

8. The method of claim 5, wherein digesting the modified mammalian heparanase protein by said matching protease is effected at a pH in which said protease has an optimal protease activity.

\* \* \* \* \*

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 1721
        (B) TYPE: nucleic acid
        (C) STRANDEDNESS: double
        (D) TOPOLOGY: linear (xi) SEQUENCE DESCRIPTION: SEQ ID NO: 1:

```
CTAGAGCTTT CGACTCTCCG CTGCGCGGCA GCTGGCGGGG GGAGCAGCCA GGTGAGCCCA      60

AGATGCTGCT GCGCTCGAAG CCTGCGCTGC CGCCGCCGCT GATGCTGCTG CTCCTGGGGC     120

CGCTGGGTCC CCTCTCCCCT GGCGCCCTGC CCCGACCTGC GCAAGCACAG GACGTCGTGG     180

ACCTGGACTT CTTCACCCAG GAGCCGCTGC ACCTGGTGAG CCCCTCGTTC CTGTCCGTCA     240

CCATTGACGC CAACCTGGCC ACGGACCCGC GGTTCCTCAT CCTCCTGGGT TCTCCAAAGC     300

TTCGTACCTT GGCCAGAGGC TTGTCTCCTG CGTACCTGAG GTTTGGTGGC ACCAAGACAG     360

ACTTCCTAAT TTTCGATCCC AAGAAGGAAT CAACCTTTGA AGAGAAGT TACTGGCAAT       420

CTCAAGTCAA CCAGGATATT TGCAAATATG GATCCATCCC TCCTGATGTG GAGGAGAAGT     480

TACGGTTGGA ATGGCCCTAC CAGGAGCAAT TGCTACTCCG AGAACACTAC CAGAAAAAGT     540

TCAAGAACAG CACCTACTCA AGAAGCTCTG TAGATGTGCT ATACACTTTT GCAAACTGCT     600

CAGGACTGGA CTTGATCTTT GGCCTAAATG CGTTATTAAG AACAGCAGAT TTGCAGTGGA     660

ACAGTTCTAA TGCTCAGTTG CTCCTGGACT ACTGCTCTTC CAAGGGGTAT AACATTTCTT     720

GGGAACTAGG CAATGAACCT AACAGTTTCC TTAAGAAGGC TGATATTTTC ATCAATGGGT     780

CGCAGTTAGG AGAAGATTAT ATTCAATTGC ATAAACTTCT AAGAAAGTCC ACCTTCAAAA     840

ATGCAAAACT CTATGGTCCT GATGTTGGTC AGCCTCGAAG AAAGACGGCT AAGATGCTGA     900

AGAGCTTCCT GAAGGCTGGT GGAGAAGTGA TTGATTCAGT TACATGGCAT CACTACTATT     960
```

```
TGAATGGACG GACTGCTACC AGGGAAGATT TTCTAAACCC TGATGTATTG GACATTTTTA   1020

TTTCATCTGT GCAAAAAGTT TTCCAGGTGG TTGAGAGCAC CAGGCCTGGC AAGAAGGTCT   1080

GGTTAGGAGA AACAAGCTCT GCATATGGAG GCGGAGCGCC CTTGCTATCC GACACCTTTG   1140

CAGCTGGCTT TATGTGGCTG GATAAATTGG GCCTGTCAGC CCGAATGGGA ATAGAAGTGG   1200

TGATGAGGCA AGTATTCTTT GGAGCAGGAA ACTACCATTT AGTGGATGAA AACTTCGATC   1260

CTTTACCTGA TTATTGGCTA TCTCTTCTGT TCAAGAAATT GGTGGGCACC AAGGTGTTAA   1320

TGGCAAGCGT GCAAGGTTCA AAGAGAAGGA AGCTTCGAGT ATACCTTCAT TGCACAAACA   1380

CTGACAATCC AAGGTATAAA GAAGGAGATT TAACTCTGTA TGCCATAAAC CTCCATAACG   1440

TCACCAAGTA CTTGCGGTTA CCCTATCCTT TTTCTAACAA GCAAGTGGAT AAATACCTTC   1500

TAAGACCTTT GGGACCTCAT GGATTACTTT CCAAATCTGT CCAACTCAAT GGTCTAACTC   1560

TAAAGATGGT GGATGATCAA ACCTTGCCAC CTTTAATGGA AAAACCTCTC CGGCCAGGAA   1620

GTTCACTGGG CTTGCCAGCT TTCTCATATA GTTTTTTTGT GATAAGAAAT GCCAAAGTTG   1680

CTGCTTGCAT CTGAAAATAA AATATACTAG TCCTGACACT G                       1721

(2) INFORMATION FOR SEQ ID NO: 2:

(i) SEQUENCE CHARACTERISTICS:
        (A) LENGTH: 543
        (B) TYPE: amino acid
        (C) STRANDEDNESS: single
        (D) TOPOLOGY: linear (xi) SEQUENCE DESCRIPTION: SEQ ID NO: 2:

Met Leu Leu Arg Ser Lys Pro Ala Leu Pro Pro Leu Met Leu Leu
                  5                  10                  15

Leu Leu Gly Pro Leu Gly Pro Leu Ser Pro Gly Ala Leu Pro Arg Pro
             20                  25                  30

Ala Gln Ala Gln Asp Val Val Asp Leu Asp Phe Phe Thr Gln Glu Pro
         35                  40                  45

Leu His Leu Val Ser Pro Ser Phe Leu Ser Val Thr Ile Asp Ala Asn
     50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220
```

```
Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
            245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
435                 440                 445

Asp Leu Thr Leu Tyr Ala Ile Asn Leu His Asn Val Thr Lys Tyr Leu
450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
            485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
530                 535                 540         543

(2) INFORMATION FOR SEQ ID NO: 3:

(i) SEQUENCE CHARACTERISTICS:
        (A) LENGTH: 1721
        (B) TYPE: nucleic acid
        (C) STRANDEDNESS: Double
        (D) TOPOLOGY: linear (xi) SEQUENCE DESCRIPTION: SEQ ID NO: 3:

CT AGA GCT TTC GAC      14

TCT CCG CTG CGC GGC AGC TGG CGG GGG GAG CAG CCA GGT GAG CCC AAG     62

ATG CTG CTG CGC TCG AAG CCT GCG CTG CCG CCG CCG CTG ATG CTG CTG    110
Met Leu Leu Arg Ser Lys Pro Ala Leu Pro Pro Pro Leu Met Leu Leu
                5                   10                  15
```

```
CTC CTG GGG CCG CTG GGT CCC CTC TCC CCT GGC GCC CTG CCC CGA CCT    158
Leu Leu Gly Pro Leu Gly Pro Leu Ser Pro Gly Ala Leu Pro Arg Pro
            20                  25                  30

GCG CAA GCA CAG GAC GTC GTG GAC CTG GAC TTC TTC ACC CAG GAG CCG    206
Ala Gln Ala Gln Asp Val Val Asp Leu Asp Phe Phe Thr Gln Glu Pro
        35                  40                  45

CTG CAC CTG GTG AGC CCC TCG TTC CTG TCC GTC ACC ATT GAC GCC AAC    254
Leu His Leu Val Ser Pro Ser Phe Leu Ser Val Thr Ile Asp Ala Asn
    50                  55                  60

CTG GCC ACG GAC CCG CGG TTC CTC ATC CTC CTG GGT TCT CCA AAG CTT    302
Leu Ala Thr Asp Pro Arg Phe Leu Ile Leu Leu Gly Ser Pro Lys Leu
65                  70                  75                  80

CGT ACC TTG GCC AGA GGC TTG TCT CCT GCG TAC CTG AGG TTT GGT GGC    350
Arg Thr Leu Ala Arg Gly Leu Ser Pro Ala Tyr Leu Arg Phe Gly Gly
                85                  90                  95

ACC AAG ACA GAC TTC CTA ATT TTC GAT CCC AAG AAG GAA TCA ACC TTT    398
Thr Lys Thr Asp Phe Leu Ile Phe Asp Pro Lys Lys Glu Ser Thr Phe
            100                 105                 110

GAA GAG AGA AGT TAC TGG CAA TCT CAA GTC AAC CAG GAT ATT TGC AAA    446
Glu Glu Arg Ser Tyr Trp Gln Ser Gln Val Asn Gln Asp Ile Cys Lys
        115                 120                 125

TAT GGA TCC ATC CCT CCT GAT GTG GAG GAG AAG TTA CGG TTG GAA TGG    494
Tyr Gly Ser Ile Pro Pro Asp Val Glu Glu Lys Leu Arg Leu Glu Trp
    130                 135                 140

CCC TAC CAG GAG CAA TTG CTA CTC CGA GAA CAC TAC CAG AAA AAG TTC    542
Pro Tyr Gln Glu Gln Leu Leu Leu Arg Glu His Tyr Gln Lys Lys Phe
145                 150                 155                 160

AAG AAC AGC ACC TAC TCA AGA AGC TCT GTA GAT GTG CTA TAC ACT TTT    590
Lys Asn Ser Thr Tyr Ser Arg Ser Ser Val Asp Val Leu Tyr Thr Phe
                165                 170                 175

GCA AAC TGC TCA GGA CTG GAC TTG ATC TTT GGC CTA AAT GCG TTA TTA    638
Ala Asn Cys Ser Gly Leu Asp Leu Ile Phe Gly Leu Asn Ala Leu Leu
            180                 185                 190

AGA ACA GCA GAT TTG CAG TGG AAC AGT TCT AAT GCT CAG TTG CTC CTG    686
Arg Thr Ala Asp Leu Gln Trp Asn Ser Ser Asn Ala Gln Leu Leu Leu
        195                 200                 205

GAC TAC TGC TCT TCC AAG GGG TAT AAC ATT TCT TGG GAA CTA GGC AAT    734
Asp Tyr Cys Ser Ser Lys Gly Tyr Asn Ile Ser Trp Glu Leu Gly Asn
    210                 215                 220

GAA CCT AAC AGT TTC CTT AAG AAG GCT GAT ATT TTC ATC AAT GGG TCG    782
Glu Pro Asn Ser Phe Leu Lys Lys Ala Asp Ile Phe Ile Asn Gly Ser
225                 230                 235                 240

CAG TTA GGA GAA GAT TAT ATT CAA TTG CAT AAA CTT CTA AGA AAG TCC    830
Gln Leu Gly Glu Asp Tyr Ile Gln Leu His Lys Leu Leu Arg Lys Ser
                245                 250                 255

ACC TTC AAA AAT GCA AAA CTC TAT GGT CCT GAT GTT GGT CAG CCT CGA    878
Thr Phe Lys Asn Ala Lys Leu Tyr Gly Pro Asp Val Gly Gln Pro Arg
            260                 265                 270

AGA AAG ACG GCT AAG ATG CTG AAG AGC TTC CTG AAG GCT GGT GGA GAA    926
Arg Lys Thr Ala Lys Met Leu Lys Ser Phe Leu Lys Ala Gly Gly Glu
        275                 280                 285

GTG ATT GAT TCA GTT ACA TGG CAT CAC TAC TAT TTG AAT GGA CGG ACT    974
Val Ile Asp Ser Val Thr Trp His His Tyr Tyr Leu Asn Gly Arg Thr
    290                 295                 300

GCT ACC AGG GAA GAT TTT CTA AAC CCT GAT GTA TTG GAC ATT TTT ATT   1022
Ala Thr Arg Glu Asp Phe Leu Asn Pro Asp Val Leu Asp Ile Phe Ile
305                 310                 315                 320

TCA TCT GTG CAA AAA GTT TTC CAG GTG GTT GAG AGC ACC AGG CCT GGC   1070
Ser Ser Val Gln Lys Val Phe Gln Val Val Glu Ser Thr Arg Pro Gly
```

```
               325                 330                 335
AAG AAG GTC TGG TTA GGA GAA ACA AGC TCT GCA TAT GGA GGC GGA GCG     1118
Lys Lys Val Trp Leu Gly Glu Thr Ser Ser Ala Tyr Gly Gly Gly Ala
            340                 345                 350

CCC TTG CTA TCC GAC ACC TTT GCA GCT GGC TTT ATG TGG CTG GAT AAA     1166
Pro Leu Leu Ser Asp Thr Phe Ala Ala Gly Phe Met Trp Leu Asp Lys
            355                 360                 365

TTG GGC CTG TCA GCC CGA ATG GGA ATA GAA GTG GTG ATG AGG CAA GTA     1214
Leu Gly Leu Ser Ala Arg Met Gly Ile Glu Val Val Met Arg Gln Val
            370                 375                 380

TTC TTT GGA GCA GGA AAC TAC CAT TTA GTG GAT GAA AAC TTC GAT CCT     1262
Phe Phe Gly Ala Gly Asn Tyr His Leu Val Asp Glu Asn Phe Asp Pro
385                 390                 395                 400

TTA CCT GAT TAT TGG CTA TCT CTT CTG TTC AAG AAA TTG GTG GGC ACC     1310
Leu Pro Asp Tyr Trp Leu Ser Leu Leu Phe Lys Lys Leu Val Gly Thr
            405                 410                 415

AAG GTG TTA ATG GCA AGC GTG CAA GGT TCA AAG AGA AGG AAG CTT CGA     1358
Lys Val Leu Met Ala Ser Val Gln Gly Ser Lys Arg Arg Lys Leu Arg
            420                 425                 430

GTA TAC CTT CAT TGC ACA AAC ACT GAC AAT CCA AGG TAT AAA GAA GGA     1406
Val Tyr Leu His Cys Thr Asn Thr Asp Asn Pro Arg Tyr Lys Glu Gly
            435                 440                 445

GAT TTA ACT CTG TAT GCC ATA AAC CTC CAT AAC GTC ACC AAG TAC TTG     1454
Asp Leu Thr Leu Tyr Ala Ile Asn Leu His Asn Val Thr Lys Tyr Leu
            450                 455                 460

CGG TTA CCC TAT CCT TTT TCT AAC AAG CAA GTG GAT AAA TAC CTT CTA     1502
Arg Leu Pro Tyr Pro Phe Ser Asn Lys Gln Val Asp Lys Tyr Leu Leu
465                 470                 475                 480

AGA CCT TTG GGA CCT CAT GGA TTA CTT TCC AAA TCT GTC CAA CTC AAT     1550
Arg Pro Leu Gly Pro His Gly Leu Leu Ser Lys Ser Val Gln Leu Asn
            485                 490                 495

GGT CTA ACT CTA AAG ATG GTG GAT GAT CAA ACC TTG CCA CCT TTA ATG     1598
Gly Leu Thr Leu Lys Met Val Asp Asp Gln Thr Leu Pro Pro Leu Met
            500                 505                 510

GAA AAA CCT CTC CGG CCA GGA AGT TCA CTG GGC TTG CCA GCT TTC TCA     1646
Glu Lys Pro Leu Arg Pro Gly Ser Ser Leu Gly Leu Pro Ala Phe Ser
            515                 520                 525

TAT AGT TTT TTT GTG ATA AGA AAT GCC AAA GTT GCT GCT TGC ATC TGA     1694
Tyr Ser Phe Phe Val Ile Arg Asn Ala Lys Val Ala Ala Cys Ile
            530                 535                 540     543

AAA TAA AAT ATA CTA GTC CTG ACA CTG                                  1721
```

(2) INFORMATION FOR SEQ ID NO: 4:

(i) SEQUENCE CHARACTERISTICS:
        (A) LENGTH: 26
        (B) TYPE: nucleic acid
        (C) STRANDEDNESS: single
        (D) TOPOLOGY: linear (xi) SEQUENCE DESCRIPTION: SEQ ID NO: 4:

CGCATATGCA GGACGTCGTG GACCTG                                     26

(2) INFORMATION FOR SEQ ID NO: 5:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 5:

TATGATCCTC TAGTACTTCT CGAC                                    24

(2) INFORMATION FOR SEQ ID NO: 6:

(i) SEQUENCE CHARACTERISTICS:
        (A) LENGTH: 35
        (B) TYPE: nucleic acid
        (C) STRANDEDNESS: single
        (D) TOPOLOGY: linear (xi) SEQUENCE DESCRIPTION: SEQ ID NO: 6:

AGGAATTCAC CATGCTGCTG CGCTCGAAGC CTGCG                         35

(2) INFORMATION FOR SEQ ID NO: 7:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO: 7:

GAGTAGCAAT TGCTCCTGGT AG                                      22

(2) INFORMATION FOR SEQ ID NO: 8:

(i) SEQUENCE CHARACTERISTICS:
        (A) LENGTH: 35
        (B) TYPE: nucleic acid
        (C) STRANDEDNESS: single
        (D) TOPOLOGY: linear (xi) SEQUENCE DESCRIPTION: SEQ ID NO: 8:

GTCTCGAGAA AAGACAGGAC GTCGTGGACC TGGAC                         35

(2) INFORMATION FOR SEQ ID NO: 9:

(i) SEQUENCE CHARACTERISTICS:
        (A) LENGTH: 59
        (B) TYPE: nucleic acid
        (C) STRANDEDNESS: single
        (D) TOPOLOGY: linear (xi) SEQUENCE DESCRIPTION: SEQ ID NO: 9:

AATTCACCAT GTCTGCACTT CTGATCCTAG CTCTTGTTGG AGCTGCAGTT         50

GCTCAGGAC                                                     59

(2) INFORMATION FOR SEQ ID NO: 10:

(i) SEQUENCE CHARACTERISTICS:
        (A) LENGTH: 53
        (B) TYPE: nucleic acid
        (C) STRANDEDNESS: single
        (D) TOPOLOGY: linear (xi) SEQUENCE DESCRIPTION: SEQ ID NO: 10:

CCTGAGCAAC TGCAGCTCCA ACAAGAGCTA GGATCAGAAG TGCAGACATG GTG     53

(2) INFORMATION FOR SEQ ID NO: 11:

(i) SEQUENCE CHARACTERISTICS:
        (A) LENGTH: 52
        (B) TYPE: nucleic acid
        (C) STRANDEDNESS: single
        (D) TOPOLOGY: linear (xi) SEQUENCE DESCRIPTION: SEQ ID NO: 11:

AATTCACCAT GTCTGCACTT CTGATCCTAG CTCTTGTTGG AGCTGCAGTT GC          52

(2) INFORMATION FOR SEQ ID NO: 12:

(i) SEQUENCE CHARACTERISTICS:
        (A) LENGTH: 50
        (B) TYPE: nucleic acid
        (C) STRANDEDNESS: single
        (D) TOPOLOGY: linear (xi) SEQUENCE DESCRIPTION: SEQ ID NO: 12:

CGGCAACTGC AGCTCCAACA AGAGCTAGGA TCAGAAGTGC AGACATGGTG             50

(2) INFORMATION FOR SEQ ID NO: 13:

(i) SEQUENCE CHARACTERISTICS:
        (A) LENGTH: 4
        (B) TYPE: amino acid
        (C) STRANDEDNESS: single
        (D) TOPOLOGY: linear (xi) SEQUENCE DESCRIPTION: SEQ ID NO: 13:

Ile Glu Gly Arg
            4

(2) INFORMATION FOR SEQ ID NO: 14:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO: 14:

Asp Asp Asp Asp Lys
                 5

(2) INFORMATION FOR SEQ ID NO: 15:

(i) SEQUENCE CHARACTERISTICS:
        (A) LENGTH: 42
        (B) TYPE: nucleic acid
        (C) STRANDEDNESS: single
        (D) TOPOLOGY: linear (xi) SEQUENCE DESCRIPTION: SEQ ID NO: 15:

CCATCGATAG AAGGACGAAA AAAGTTCAAG AACAGCACCT AC                     42

(2) INFORMATION FOR SEQ ID NO: 16:

(i) SEQUENCE CHARACTERISTICS:
        (A) LENGTH: 28
        (B) TYPE: nucleic acid
        (C) STRANDEDNESS: single
        (D) TOPOLOGY: linear (xi) SEQUENCE DESCRIPTION: SEQ ID NO: 16:

GGATCGATTG GTAGTGTTCT CGGAGTAG                                     28

(2) INFORMATION FOR SEQ ID NO: 17:

(i) SEQUENCE CHARACTERISTICS:
        (A) LENGTH: 39
        (B) TYPE: nucleic acid
        (C) STRANDEDNESS: single
        (D) TOPOLOGY: linear (xi) SEQUENCE DESCRIPTION: SEQ ID NO: 17:

GGATCGATAG AAGGACGATC TCAAGTCAAC CAGGATATT                          39

(2) INFORMATION FOR SEQ ID NO: 18:

(i) SEQUENCE CHARACTERISTICS:
       (A) LENGTH: 32
       (B) TYPE: nucleic acid
       (C) STRANDEDNESS: single
       (D) TOPOLOGY: linear (xi) SEQUENCE DESCRIPTION: SEQ ID NO: 18:

CCATCGATGC CCAGTAACTT CTCTCTTCAA AG                                 32

(2) INFORMATION FOR SEQ ID NO: 19:

(i) SEQUENCE CHARACTERISTICS:
       (A) LENGTH: 24
       (B) TYPE: nucleic acid
       (C) STRANDEDNESS: single
       (D) TOPOLOGY: linear (xi) SEQUENCE DESCRIPTION: SEQ ID NO: 19:

TCAGATGCAA GCAGCAACTT TGGC                                          24

(2) INFORMATION FOR SEQ ID NO: 20:

(i) SEQUENCE CHARACTERISTICS:
       (A) LENGTH: 23
       (B) TYPE: nucleic acid
       (C) STRANDEDNESS: single
       (D) TOPOLOGY: linear (xi) SEQUENCE DESCRIPTION: SEQ ID NO: 20:

GAGCAGCCAG GTGAGCCCAA GAT                                           23

(2) INFORMATION FOR SEQ ID NO: 21:

(i) SEQUENCE CHARACTERISTICS:
       (A) LENGTH: 44
       (B) TYPE: nucleic acid
       (C) STRANDEDNESS: single
       (D) TOPOLOGY: linear (xi) SEQUENCE DESCRIPTION: SEQ ID NO: 21:

CCATCGATGA CGACGACAAG AAAAAGTTCA AGAACAGCAC CTAC                    44

(2) INFORMATION FOR SEQ ID NO: 22:

(i) SEQUENCE CHARACTERISTICS:
       (A) LENGTH: 29
       (B) TYPE: nucleic acid
       (C) STRANDEDNESS: single
       (D) TOPOLOGY: linear (xi) SEQUENCE DESCRIPTION: SEQ ID NO: 22:

GGATCGATCT GGTAGTGTTC TCGGAGTAG                                     29

(2) INFORMATION FOR SEQ ID NO: 23:

(i) SEQUENCE CHARACTERISTICS:
       (A) LENGTH: 43
       (B) TYPE: nucleic acid
       (C) STRANDEDNESS: single
       (D) TOPOLOGY: linear -continued (xi) SEQUENCE DESCRIPTION: SEQ ID NO: 23:

GGATCGATGA CGACGACAAG TCTCAAGTCA ACCAGGATAT TTG        43

(2) INFORMATION FOR SEQ ID NO: 24:

(i) SEQUENCE CHARACTERISTICS:
        (A) LENGTH: 33
        (B) TYPE: nucleic acid
        (C) STRANDEDNESS: single
        (D) TOPOLOGY: linear (xi) SEQUENCE DESCRIPTION: SEQ ID NO: 24:

CCATCGATTT GGGAGTAACT TCTCTCTTCA AAG        33

(2) INFORMATION FOR SEQ ID NO: 25:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO: 25:

Ser Gln Val Asn Gln
               5